(12) United States Patent
Eritja et al.

(10) Patent No.: US 6,831,072 B2
(45) Date of Patent: Dec. 14, 2004

(54) COMPOSITIONS AND METHODS OF SYNTHESIS AND USE OF NOVEL NUCLEIC ACID STRUCTURES

(75) Inventors: Ramón Eritja, Barcelona (ES); Ramón Güimil García, Heidelberg (DE)

(73) Assignee: Cygene, Inc., Coral Springs, FL (US)

( * ) Notice: Subject to any disclaimer, the term of this patent is extended or adjusted under 35 U.S.C. 154(b) by 350 days.

(21) Appl. No.: 10/055,732

(22) Filed: Jan. 22, 2002

(65) Prior Publication Data

US 2003/0135040 A1 Jul. 17, 2003

Related U.S. Application Data

(63) Continuation-in-part of application No. 09/702,066, filed on Oct. 30, 2000, now abandoned.
(60) Provisional application No. 60/197,559, filed on Apr. 17, 2000, and provisional application No. 60/162,627, filed on Oct. 29, 1999.

(51) Int. Cl.$^7$ .................. A01N 43/04; A61K 31/70; C07H 19/20; C07H 19/167
(52) U.S. Cl. ............... 514/46; 536/26.13; 536/27.6
(58) Field of Search ................ 536/26.13, 27.6; 514/46

(56) References Cited

PUBLICATIONS

Tumey, B. J. et al., Stability of Phosphorothioate Oligonucleotides in Aqueous Ammonia in Presence of Stainless Steel, Nucleosides & Nucleotides, 1999 18(1), 89–93.
Hattori, M., et al., The Structure of Triple–Stranded G–2C Polynucleotide Helices, Biopolymers, 1976; 15: 523–531.
Rao, T. S. et al., Synthesis of Oligonucleotides Containing 7–(2–Deoxy–β–D–erythro–peniofuranosly)guanine and 8–Amino–2'–deoxyguanosine, J. Heteracyclic Chem., 1994; 31:935–940.
Tester, J. et al., Synthesis and Characterization of DNA Oligomers and Duplexes Containing Covalently Attached Molecular Labels, J. Am. Chem. Soc., 1989; 111:6966–6976.
Holmes, R.E. and Robins, R.K. Purine Nucleotides, IX. The Sythesis of 9–β–D–Ribofuranosyl Uric Acid and Other Related 8–Subsituted Purine Ribonucleosides, J. Am. Chem. Soc. 1965;87: 1772–1776.
Long, R.A. et al., The Synthesis of 8–Amino– and 8–Substituted Aminopurine Nucleosides, J. Org. Chem. 1967; 32: 2751–2756.

Horne, D.A. and Dervan, P.B., Recognition of Mixed–Sequence Duplex DNA by Alternate–Strand Triple–Helix Formation J. Am. Chem. Soc. 1990; 112: 2435–2437.
Froehler, B.C. et al., Triple–Helix Formation and Cooperative Binding by Oligodeoxynucleotides with a 3'–3' Internucleotide Junction, Biochem. 1992; 31: 1603–1609.
Kandimalla, E.R. and Agrawal, S., Hoogsteen DNA Duplexes of 3'–3'– and 5'–5'–Linked Oligonucleotides and Triplex Formation with RNA and DNA Pyrimidine Single Strands, Biochem., 1996; 35: 15332–15339.
Shields, G.C. et al., Molecular Dynamics Simulations of the d(T•A•T) Triple Helix, J. Am. Chem. Soc. 1997; 119: 7463–7469.
Holmes, R.E. and Robins, R.K. Purine Nucleotides, IX. The Sythesis of 9–βD–Ribofuranosyl Uric Acid and Other Related 8–Subsituted Purine Ribonucleosides, J. Am. Chem. Soc. 1965;87: 1772–1776.
Massoit, g. et al., Phosphite Coupling Procedure for Generating Internucleotide Links, J. Am. Chem. Soc. 1975; 97: 3278–3279.
Durand, M. et al., Triple–Helix Formation by an Oligonucleotide Containing One $(dA)_{12}$ and Two $(dT)_{12}$ Sequences Bridged by Two Hexaethylene Glycol Chains, Biochem. 1992; 31: 9197–9204.
Kawai, K. and Saito, I., Stabilization of Hoogsteen Base Pairing by Introduction of $NH_2$ Group at the C8 Position of Adenine, Tetra. Let., 1998; 39: 5221–5224.
Garcia, R.G., et al, Theoretical calculations, synthesis and base pairing properties of oligoneucleotides containing 8–amino–2'–deoxyadenosine, Nac. Acids Res. 1999; 27: 1991–1998.
Garcia, R.G. et al., Triple Helix Stabilization Properties of Oligonucleotides Containing 8–Amino–2'–Deoxyguanosine, Bioorg. & Med. Chem. Lets., 1998; 8: 3011–3016.
Solvia, R. et al., DNA–tiplex stabilizing properties of 8–aminoguanine, Nuc. Acids Res., 2000; 28: 4531–4539.
Loakes, D. et al, 3–Nitropyrrole and 5–nitroindole as universal bases in primers for DNA sequencing, Nuc. Acids Res., 1995; 23: 2361–2366.
Rippe, K. and Jovin, T.M., Parallel–Stranded Duplex DNA, Meth. in Enzymology, 1993; 211: 199–220.

*Primary Examiner*—Janet L. Epps-Ford
(74) *Attorney, Agent, or Firm*—Buchanan Ingersoll PC

(57) ABSTRACT

The present invention is directed to a method to produce 8-amino-2'deoxyadenosine by treating 8-azido-2'deoxyadenosine with an aqueous solution of methylamine or dimethylamine.

8 Claims, 38 Drawing Sheets

R-NH$_2$ = 40% aq. CH$_3$NH$_2$, 1M aq. NH$_2$-(CH$_2$)$_6$-NH$_2$,
1M aq. NH$_2$-[(CH$_2$)$_2$-O]$_2$-(CH$_2$)$_2$-NH$_2$, 1M aq. NH$_2$-(CH$_2$)$_2$-S-S-(CH$_2$)$_2$-NH$_2$

RR'-NH$_2$ = 40% (CH$_3$)$_2$NH, 1M aq. piperidine (dA is defined as 2'deoxyadenosine.)

(dA is defined as 2'deoxyadenosine.)

COMPOSITIONS AND METHODS OF SYNTHESIS AND USE OF NOVEL NUCLEIC ACID STRUCTURES

RELATED APPLICATIONS

The present application is a continuation-in-part of prior application 09/702,066, filed Oct. 30, 2000, now abandoned, which claims priority of U.S. Provisional Patent Application No. 60/162,627, filed Oct. 29, 1999 and U.S. Provisional Application No. 60/197,559 filed Apr. 17, 2000, all of which are incorporated herein in their entirety by reference.

TECHNICAL FIELD

The invention relates to novel oligomer analogs and to oligonucleotide-based diagnostics by binding of the oligomers to single and double-stratided nucleic acids target sequences. More specifically, the invention concerns oligomers containing 8-aminopurine base residues and their triple-helix stabilization properties.

BACKGROUND OF THE INVENTION

It has been shown that oligonucleotides could bind to homopurine-homopyrimidine sequences of double stranded DNA by forming triple helices. The formation of nucleic acid triple helices offers the possibility of designing sequence-specific DNA binding molecules, which may have important uses as diagnostic tools as well as therapeutic treatments. For example, triple helices are used for the extraction and purification of specific nucleotide sequences, control of gene expression, mapping genomic DNA, detection of mutations in homopurine DNA sequences, site-directed mutagenesis, triplex-mediated inhibition of viral DNA integration, nonenzymatic ligation of double-helical DNA and quantitation of polymerase chain reactions (for reviews see references 1–3).

One of the problems for the development of applications based on triple helix formation is the low stability of triple helices especially at neutral pH. Another problem associated with the use of triplex forming oligonucleotides (TFO) is the presence of interruptions in the homopurine-homopyrimidine tracks. In order to overcome this problem a lot of effort has been put into the design and preparation of modified oligonucleotides in order to enhance triple helix stability. See references 39 and 40. One of the most successful modifications is to replace natural bases with some modified bases such as 5-methylcytidine, 5-bromouracil, 5-aminouracil, $N^4$-spermnine-5-methylcytidine, or 5-methyl-2,6(1H,3H)-pyrimidinedione.

The most studied type of triple helix formation is the so-called purine: pyrimidine: pyrimidine motif. (FIG. 1). In this motif, the purine: pyrimidine strands correspond to the target double-stranded DNA sequence (known as the Watson-Crick purine and pyrimidine strands) and the Hoogsteen strand is a pyrimidine strand used for the specific recognition of the double-stranded DNA. See U.S. Pat. Nos. 5,422,251 and 5,693,471. For these reasons, most of the base analogues studied for triple helix stabilization are modified pyrimidines located at the Hoogsteen strand, though there are some recent disclosures of purine analogs. For example, see U.S. Pat. Nos. 5,739,308; 5,645,985; and 5,594,121.

In order to obtain a triplex, in some occasions, purine residues are concentrated on one chain and are linked to a pyrimidine chain of inverted polarity. By "inverted polarity" is meant that the oligomer contains tandem sequences which have opposite polarity, i.e. one segment or region of sequences having polarity 5'-→3', followed by another with polarity 3'-→5' or vice versa. This implies that these sequences are joined by linkages which can be thought as a 3'-3' or a 5'-5' internucleotide junction. Such oligomers named "parallel-stranded DNA" have been synthesized See References 34, 42 and 43.

Recent results have shown that the introduction of an amino group at position 8 of adenine increases the stability of triple helix due to the combined effect of the gain in one Hoogsteen purine-pyrimidine H-bond, (see references 4–6) and the ability of the amino group to be integrated into the "spine of hydration" located in the minor-Major groove of the triplex structure (FIG. 2). (See references 4–7). A similar behavior has been observed with 8-amino-2-deoxyguanosine and 8-amino-2'-deoxyinosine (FIG. 2). (See reference 11). The preparation and the characterization of the binding properties of oligonucleotides containing 8-aminopurines has been described, but these oligonucleotides can not be directly used for the specific recognition of double-stranded DNA sequences because the modified bases are purines that are in the target sequence and not in the Hoogsteen strand used for the specific recognition of double-stranded DNA.

Synthetic oligonucleotides probes have been proven very useful in the detection of cloned DNA sequences. When a partial protein sequence is available, a mixture of oligonucleotides presenting all possible DNA sequences can be successfully used as a probe or as PCR or sequencing primers for screening of cloned DNA (or amplification of DNA. See reference 44. The mixed probe approach may have two principal drawbacks when the complexity of the mixture is very high. First, the oligonucleotide probes must, for reasons of practicality, be synthesized together on the same support. Thus, the products of the synthesis can never be adequately characterized. Second, since the exact coding sequence is not known, it is difficult to set appropriate stringent conditions for the hybridisation and subsequent washings. A universal baseone that could base pair equally well with any of the four natural basesould resolve these two difficulties. A number of compounds have been tested as possible universal bases, with being 2'-deoxyinosine one of the most successfully used. See references 45–50.

Other molecular biological techniques, such as selective restriction of nucleic acids and target detection, can be improved. Though current techniques are adequate, there are inherent problems in the amplification steps. The PCR system will amplify any DNA added to the mixture, regardless of whether it contains the correct target sequence. If DNA fragments are selected based only on the size of the fragment that is created by the restriction enzymes, then the target sequence may be missed entirely. Additionally, if the restriction enzymes become contaminated, there is no assurance that the correct sequences are being restricted and that the target sequence is being selected. Obtaining and maintaining purified nucleases is often problematic in laboratory settings and is even more of a problem in automated systems.

Thus, methods and compositions are needed that are capable of specifically selecting target nucleic acid sequences that do not require amplification or that can be used with amplification techniques but provide for more target specific amplification. Additionally, what is needed are compositions and methods that require less use of enzymes.

Though several techniques are currently available for modification of nucleic acid structures, what is needed are compositions and methods for binding to specific target regions of DNA or RNA sequences. Specifically what is needed are triplex structures that are stabile at neutral pHs and modified oligonucletides that can bind to specific sequences in a target nucleic acid to form triple helix structures. Modified oligonucleotides that can be used for synthesis of oligonucleotides in the 5' to 3' direction, reverse of the normal 3' to 5' synthesis direction are also needed.

What is also needed are spacer arms that can link oligonucleotides in 5' to 5' orientation or 3' to 3' orientation. Particularly needed are simple and economic methods for the synthesis of such spacer arms and such paired oligonucleotide structures.

Compositions and methods for incorporation of modified nucleic acid bases are also needed. What is particularly needed are methods and compositions comprising a base labeled with active compounds, such as intercalating agents, photoreactive agents and cleavage agents that are attached to the base through a linker arm.

SUMMARY OF THE INVENTION

The present invention is directed to methods and compositions of nucleic acid structures that are used for detection of specific nucleic acid sequences. One of the embodiments of the present invention comprises compositions and methods for the preparation of oligonucleotides carrying modified nucleic acids, such as 8-aminoadenine, 8-aminoguanine and 8-aminohypoxanthine, that are connected 3' to 3' or 5' to 5' (head-to-head or tail-to-tail) to a Hoogsteen pyrimidine strand. For example, see FIG. 3. These modified oligonucleotides allow the specific recognition of double-stranded, and single-stranded nucleic acids by binding to the Watson-Crick pyrimidine strand via a triple helix. Additionally, the present invention comprises a universal base oligonucleotide that forms stable base pairs with the four natural bases.

Preferred methods of the present invention comprise binding or capturing a predetermined sequence on DNA or RNA by forming a triple helix that will be stable at neutral pH. The stability of the triple helix at neutral pH allows the use of these modified oligonucleotides in conjunction with enzymatic reactions in order to enhance the discriminatory power of the modified oligonucleotides and the direct use of these oligonucleotides under physiological conditions.

The methods and compositions of the present invention comprise use of hairpin structures to form triplex structures. The present invention also provides methods and compositions for detecting a specific nucleic acid target. A preferred embodiment comprises methods involving hybridization of hairpin probes that comprise a 5' to 3' purine sequence, followed by a loop sequence, followed by a 3' to 5' pyrimidine sequence that is complementary to the purine sequence. These self-annealing probes comprise a region, the loop, that will not hybridize to any of the probe's sequence. The loop sequence comprises any sequence that will not hybridize to itself. At least one of the hairpin probes can be complexed with a magnetic bead or a molecule that is effective for capture or detection of the structure formed with the hairpin.

The present invention also comprises compositions and methods for making spacer arms that allow the synthesis of paired parallel stranded oligonucleotides using either 3' phosphoramidite chemistry or 5' phosphoramidite chemistry. Additionally, the oligonucleotide member of the pair an comprise any number of nucleotides.

The present invention further comprises compositions and methods for synthesis of nucleosides with linker arms for attachment of active compounds. Preferably, the active compounds include, but are not limited to, intercalation agents, photoreactive compounds and agents capable of cleaving nucleic acids. More preferably, the present invention comprises compositions and methods of synthesis and use of pyrimidine nucleosides with linker arms at the $N^4$ of 2'-deoxycytidine wherein the active compound is a protected fluorescent label and a cleavage agent, such as 5-bromouracil.

Additionally, the present invention further comprises a method to produce 8-amino-2'deoxyadenosine. In accordance with the present invention, 8-amino-2'deoxyadenosine is produced by treating 8-azido-2'deoxyadenosine with an aqueous amine solution, such as methylamine solution or a dimethylamine solution.

DETAILED DESCRIPTION OF THE INVENTION

Figure 1:
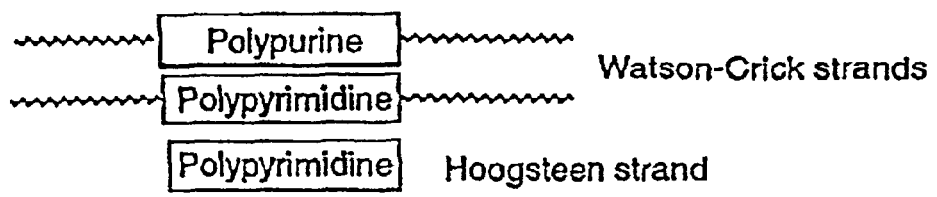
FIG. 1 is a drawing of a triple helix with the purine: pyrimidine: pyrimidine motif. Base-pairing scheme of the triads A: T: T and G: C: C+.
Figure 1:
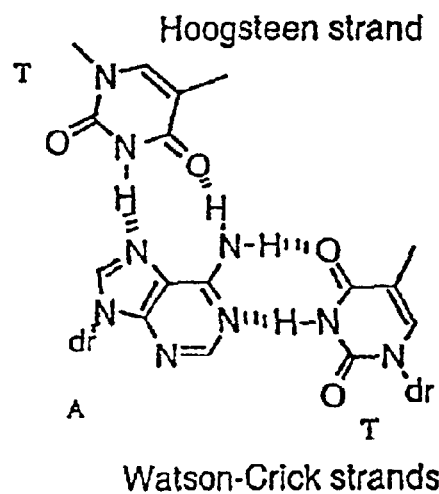
Figure 1:
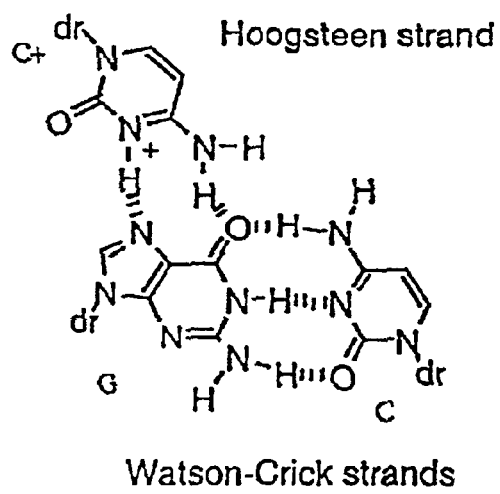

The present invention is directed to compositions of nucleic acid structures that can be used in molecular biological techniques. Additionally, the present invention is directed to methods of making such nucleic acid structures and to methods of using such nucleic acid structures. These compositions and methods can be used in such molecular biological techniques including, but not limited to, diagnostic tests involving triplex and duplex formations, signal amplification systems, nucleic acid synthesis and others.

Preferred compositions of the present invention comprise parallel-stranded oligomers having at least one 8-aminopurine in the purine strand of general formula: $^{3'}$purine strand having 8-aminopurines$^{5'}$—linker—$^{5'}$pyrimidine strand$^{3'}$ or $^{5'}$purine strand having 8-aminopurines$^{3'}$—linker—$^{3'}$pyrimidine strand$^{5'}$ where —linker— comprises any method of coupling nucleotide sequences of opposite polarity. The 8-amino purines on the purine strand have the general formula indicated below.

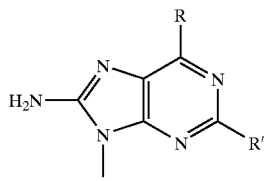

R = OH, NH$_2$
R' = H, OH, NH$_2$

The present invention also comprises compositions and methods for the preparation of oligonucleotide derivatives constituted by a polypyrimidine part linked head-to-head with a polypurine sequence carrying several 8-aminopurines such as 8-aminoadenine, 8-aminoguanine and 8-aminohypoxanthine. Methods of use of these derivatives comprise binding specifically to a predetermined target sequence, preferably a polypyrimidine target sequence, by forming a very stable triple helix that can be observed even at neutral pH. The high degree of stabilization obtained by the addition of several 8-aminopurines is especially relevant to the development of new applications based on triple helix formation such as structural studies, DNA-based diagnostic tools, and antigene therapy.

An embodiment of the present invention comprises oligonucleotide derivatives comprising two parts: a polypyrimidine part connected head-to-head to a complementary purine part carrying one or more 8-aminopurines such as 8-aminoadenine, 8-aminoguanine and 8-aminohypoxanthine. A linker molecule is located between both parts in such a way that both parts can form a double stranded structure in parallel sense. These oligonucleotide derivatives bind polypyrimidine sequences complementary (in the antiparallel sense) to the purine part by triple helix formation. DNA triple helical structures are normally observed at acidic pH. However, when oligonucleotides carrying 8-aminopurines were used, very stable triple helical structures were observed even at neutral pH. Applications based on triple helix formation will benefit from the use of these oligonucleotide derivatives.

In another embodiment of the present invention, a polypyrimidine part is connected tail-to-tail to a complementary purine part carrying one or more 8-aminopurines.

Structure of the Oligonucleotides Derivatives

The preparation of oligonucleotide derivative sequences and binding properties of oligonucleotide derivatives carrying 8-aminoadenine, 8-aminoguanine and 8-aminohypoxanthine connected head-to-head or tail-to-tail to the Hoogsteen pyrimidine strand is taught herein. Some embodiments of the sequences of the oligonucleotides of the present invention are shown in Table 1.

TABLE 1

| Name | Sequence |
|---|---|
| R-22 | $^{5'}$GAAGGAGGAGA$^{3'}$-(EG)$_6$-$^{3'}$TCTCCTCCTTC$^{5'}$ |
|  | SEQ ID NO:1              SEQ ID NO:2 |
| R-22A | $^{5'}$GAAGGA$^{N}$GGA$^{N}$GA$^{3'}$-(EG)$_6$-$^{3'}$TCTCCTCCTTC$^{5'}$ |
|  | SEQ ID NO:3              SEQ ID NO:2 |
| R-22G | $^{5'}$GAAGG$^{N}$AGG$^{N}$AGA$^{3'}$-(EG)$_6$-$^{3'}$TCTCCTCCTTC$^{5'}$ |
|  | SEQ ID NO:4              SEQ ID NO:2 |
| R-22I | $^{5'}$GAAGI$^{N}$AGI$^{N}$AGA$^{3'}$-(EG)$_6$-$^{3'}$TCTCCTCCTTC$^{5'}$ |
|  | SEQ ID NO:5              SEQ ID NO:2 |
| B-22 | $^{3'}$AGAGGAGGAAG$^{5'}$-(EG)$_6$-$^{5'}$CTTCCTCCTCT$^{3'}$ |
|  | SEQ ID NO:1              SEQ ID NO:2 |
| B-22A | $^{3'}$AGA$^{N}$GGA$^{N}$GGAAG$^{5'}$-(EG)$_6$-$^{5'}$CTTCCTCCTCT$^{3'}$ |
|  | SEQ ID NO:3              SEQ ID NO:2 |
| B-22G | $^{3'}$AGAG$^{N}$GAG$^{N}$GAAG$^{5'}$-(EG)$_6$-$^{5'}$CTTCCTCCTCT$^{3'}$ |
|  | SEQ ID NO:4              SEQ ID NO:2 |
| B-22AG | $^{3'}$AGA$^{N}$G$^{N}$GA$^{N}$G$^{N}$GAAG$^{5'}$-(EG)$_6$-$^{5'}$CTTCCTCCTCT$^{3'}$ |
|  | SEQ ID NO:6              SEQ ID NO:2 |
| B-22A control | $^{3'}$AGA$^{N}$GGA$^{N}$GGAAG$^{5'}$-(EG)$_6$-$^{5'}$TTTTTCCCCCC$^{3'}$ |
|  | SEQ ID NO:3              SEQ ID NO:7 |
| B-22AMMT | $^{3'}$AGA$^{N}$GGA$^{N}$CGAAG$^{5'}$-(EG)$_6$-$^{5'}$CTTCTTCCTCT$^{3'}$ |
|  | SEQ ID NO:8              SEQ ID NO:9 |
| B-22AMMC | $^{3'}$AGA$^{N}$GGA$^{N}$CGAAG$^{5'}$-(EG)$_6$-$^{5'}$CTTCCTCCTCT$^{3'}$ |
|  | SEQ ID NO:8              SEQ ID NO:2 |
| B-22AMMG | $^{3'}$AGA$^{N}$GGA$^{N}$CGAAG$^{5'}$-(EG)$_6$-$^{5'}$CTTCGTCCTCT$^{3'}$ |
|  | SEQ ID NO:8              SEQ ID NO:20 |
| B-22AMMA | $^{3'}$AGA$^{N}$GGA$^{N}$CGAAG$^{5'}$-(EG)$_6$-$^{5'}$CTTCATCCTCT$^{3'}$ |
|  | SEQ ID NO:8              SEQ ID NO:21 |
| B-22AMMpd | $^{3'}$AGA$^{N}$GGA$^{N}$CGAAG$^{5'}$-(EG)$_6$-$^{5'}$CTTCpdTCCTCT$^{3'}$ |
|  | SEQ ID NO:8              SEQ ID NO:22 |
| B-22AMMCA | $^{3'}$AGA$^{N}$GGA$^{N}$TGAAG$^{5'}$-(EG)$_6$-$^{5'}$CTTCCTCCTCT$^{3'}$ |
|  | SEQ ID NO:19              SEQ ID NO:2 |
| B-22AMMTA | $^{3'}$AGA$^{N}$GGA$^{N}$TGAAG$^{5'}$-(EG)$_6$-$^{5'}$CTTCTTCCTCT$^{3'}$ |
|  | SEQ ID NO:19              SEQ ID NO:9 |
| B-22AMMGA | $^{3'}$AGA$^{N}$GGA$^{N}$TGAAG$^{5'}$-(EG)$_6$-$^{5'}$CTTCGTCCTCT$^{3'}$ |
|  | SEQ ID NO:19              SEQ ID NO:20 |
| B-22AMMAA | $^{3'}$AGA$^{N}$GGA$^{N}$TGAAG$^{5'}$-(EG)$_6$-$^{5'}$CTTCATCCTCT$^{3'}$ |
|  | SEQ ID NO:19              SEQ ID NO:21 |
| B-22AMM pdA | $^{3'}$AGA$^{N}$GGA$^{N}$TGAAG$^{5'}$-(EG)$_6$-$^{5'}$CTTCpdTCCTCT$^{3'}$ |
|  | SEQ ID NO:19              SEQ ID NO:22 |
| B-22ALT1 | $^{3'}$AGA$^{N}$GGA$^{N}$GGAAG$^{5'}$-$^{5'}$TTTT-CTTCCTCCTCT$^{3'}$ |
|  | SEQ ID NO:3              SEQ ID NO:10 |

TABLE 1-continued

| Name | Sequence |
|---|---|
| B-22ALT2 | 3'AGA<sup>N</sup>GGA<sup>N</sup>GGAAG-TTTT<sup>5'</sup>-<sup>5'</sup>CTTCCTCCTCT<br>SEQ ID NO:11 SEQ ID NO:2 |
| B-22ALTGA | 3'AGA<sup>N</sup>GGA<sup>N</sup>GGAAG-GGAGG<sup>5'</sup>-<sup>5'</sup>CTTCCTCCTCT<sup>3'</sup><br>SEQ ID NO:12 SEQ ID NO:2 |

*pd = propanediol

Oligonucleotide derivatives (R-22, R-22A, R-22G, R-22I) contain 22 bases divided in two different parts and connected with a hexaethyleneglycol linker [(EG)$_6$]. One half corresponds to a polypyrimidine sequence, that will be similar to the target polypyrinudine sequence but with the inverted orientation. This sequence will be the Hoogsteen strand in the triple helix. The other half corresponds to a polypurine sequence that will be complementary to the target polypyrimidine in which two purines are substituted by the corresponding 8-aminopurine. In the oligonucleotide R-22A, two adenines are substituted by two 8-atninoguanines (A$^N$). In the oligonucleotide R22G, two guanines are substituted by two 8-aminoguanines (G$^N$) and in the oligonucleotide R-22I, two guanines are substituted by two 8-aminohypoxanthines (I$^N$) The control oligonucleotide (R-22) contains only the natural bases without modification.

The second group of oligomers (B-22, B-22A, B-22G) are similar in composition to the previous oligomers but the polypurine and the polypyrimidine parts are connected through their 5' ends with an hexaethyleneglycol linker [(EG)$_6$]. In addition an oligomer having two 8-aminoguanines and two 8-aminoadenines was prepared (B-22AG) to test whether the stabilizing properties both 8-aminopurines are additive. Also, a control oligonucleotide (B-22Acontrol) having the same oligonucleotide sequence in the polypurine part than B-22A but a non-sense polypyrimidine sequence was prepared. Finally, the oligomers B-22AMMT, B-22AMMC, B-22AMMG, B-22AMMA, B-22AMMpd, B-22AMMCA, B-22AMMTA, B-22AMMGA, B-22AMMAA and B-22AMMpdA were prepared to test the influence of interruptions on the stability of the triple helix. In the oligomer B-22AMMT there are two adenines substituted by two 8-aminoadenines. In the middle of the purine part there is a pyrimidine (C) and in the corresponding position at the Hoogsteen strand there is a T.

Figure 3:
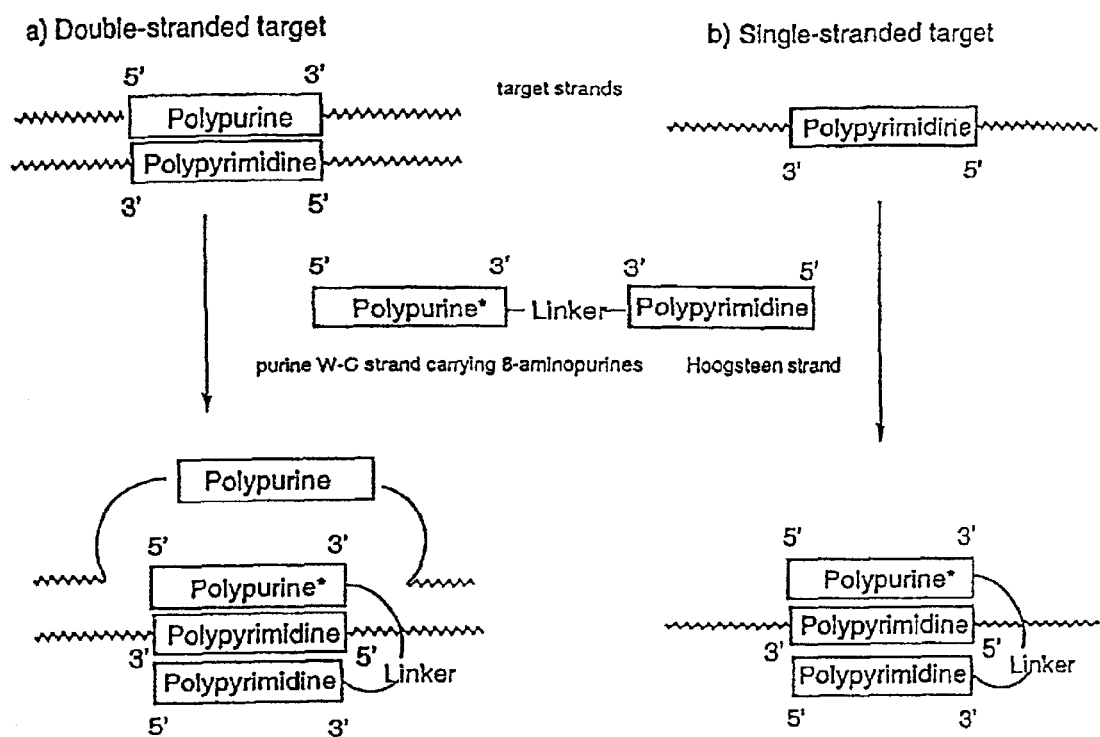
FIG. 3 is a drawing of a double- or single-stranded nucleic acid (RNA or DNA) binding with oligonucleotide derivatives of the present invention.

A third group of oligomers (B-22ALT1, B-22ALT2, B-22ALGA) have the same nucleotide sequence than B-22A but the loop between the polypurine and polypyrimidines parts are made out of nucleotides (-TTTT-(SEQ ID NO: 13) and -GGAGG-(SEQ ID NO:14)) instead of the hexaethyleneglycol bridge. FIG. 3 is a general representation of the binding of the oligonucleotides of the present invention with single or double-stranded nucleic acids.

Oligonucleotide Synthesis

Figure 4:
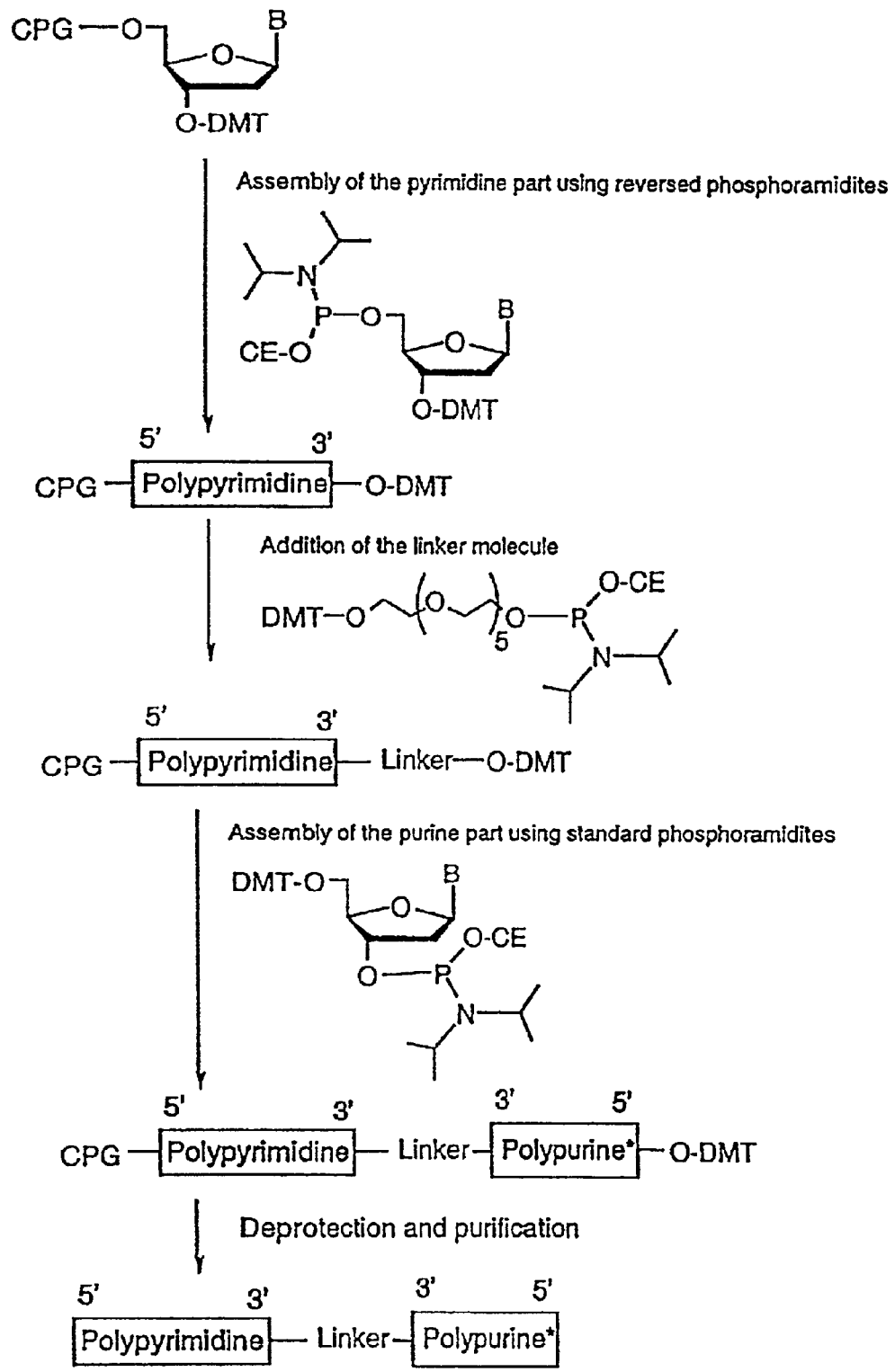
FIG. 4 shows a method for making oligonucleotide sequences containing 8-aminopurines using phosphoramidite chemistry.

A preferred method for synthesizing the oligonucleotides of the present invention comprises use of phosphoramidite chemistry. It is to be understood that the synthesis of the oligonucleotides herein described, or their equivalents, can be synthesized by any methods known to those skilled in the art. See References 34, 41 and 42. In a preferred method, oligonucleotide sequences containing 8-aminopurines were prepared using phosphoramidite chemistry on an automatic DNA synthesizer (see FIG. 4). For the preparation of the pyrimidine part, reversed C and T phosphoramidites and reversed C-support (linked to the support through the 5' end) were used. After the assembly of the pyrimidine part, an hexaethyleneglycol linker was added using a commercially available phosphoramidite. Finally, the purine part carrying the modified 8-aminopurines was assembled using standard phosphoramidites for the natural bases and the 8-aminopurine phosphoramidites prepared as described. See references 4, 5, 10–13. 8-Amino-2'-deoxyadenosine was prepared as follows: bromination of 2'-deoxyadenosine with bromine as described in Wood, et al., *Nucleic Acids Res.*, 20: 6023–6032 (1992), to produce 8-bromo-2'-deoxyadenosine, followed by azide displacement as described by Long, R. A., et al., *J. Org. Chem.* (1967) 32, 2751 (reference 36) by reacting 8-bromo-2'-deoxyadenosine with sodium azide to produce 8-azido-2'deoxyadenosine. Finally, the catalytic hydrogenation described in Long, R. A., et al. (reference 36) was replaced by an overnight (less than 5 hours) treatment of 8-azido-2'deoxyadenosine with 40% aqueous solution methylamine at 55° C. It was observed that the treatment with methylamine converted the 8-azido-2'-deoxyadenosine to 8-amino-2'-deoxyadenosine in excellent yields avoiding the use of hydrogenation. Further, a reaction of 3 ml aliquots of 8-azido-2'deoxyadenosine with 30% aqueous solution of dimethylamine gave about 60% conversion to 8-amino-2'-deoxyadenosine after about 16 hours treatment at 55° C.

The phosphoramidite of 8-aminohypoxanthine was prepared as follows. 8-Amino-2'-deoxyadenosine was deaminated by the action of the enzyme adenosine deaminase (Adenosine aminohydrolase, EC 3.5.4.4), yielding 8-amino-2'-deoxyinosine. Protection of the 8-amino group was performed by addition of the phenoxyacetyl group. See reference 50. The resulting N$^8$-phenoxyacetyl derivative was not soluble and was reacted with isobutyryl chloride. The resulting N$^8$-phenoxyacetyl-N$^8$-isobutyryl derivative was reacted with dimethoxytrityl chloride in pyridine yielding 8-amino-2'-deoxy-5'-O-dimethoxytrityl-N$^8$-isobutyryl-inosine. During the introduction of the dimethoxytrityl group, the phenoxyacetyl group was removed due to the lability of this group. Direct introduction of the isobutyryl group at N$^8$ position is possible but yields are lower than the route with the phenoxyacetyl group. The phosphoramidite group was introduced in position 3' using chloro-O-2-cyanoethoxy-N, N-diisopropylamino-phosphine as described. See reference 51.

After the assembly of the sequences, supports were treated with concentrated ammonia. Oligonucleotides carrying 8-aminoguanine were treated with 0.1 M 2-mercaptoethanol in concentrated ammonia See reference 13. After deprotection, the products were purified by reverse-phase HPLC using the DMT-on and DMT-off protocols. In all cases a major peak was obtained and collected. The purified oligonucleotides were analyzed by enzyme digestion followed by HPLC analysis of the resulting nucleosides. In all cases the purified oligonucleotides were obtained in good yields and had the correct nucleoside composition.

Binding Properties

Methods for detecting formation of triplexes are contemplated by the present invention. One of the embodiments of these methods used for the detection of the formation of the triple helix structure comprise the measurement of the triplex fusion temperature, which comprises incubating the samples at increasing temperatures vs. time, and collecting hyperchromicity data. Hyperchromicity is the amount by which the UV absorbance of a nucleic acid sample increases when going, for example, from a double stranded structure to a single strand structure as it melts in response to increasing temperature.

A preferred embodiment of the assay is described below:

1. A single stranded template, 11 bases long, of constant sequence, in most cases, consisting exclusively of a pyrimidine stretch (WC-11mer).
2. The hairpin probes described above, of the same length, where the two strands are joined by a loop consisting of 6 ethylene glycol members or the sequences TTTT (SEQ ID NO: 13) or GGAGG (SEQ ID NO:14); and the purine stretch contain modified bases (i.e., 8-amino A and/or 8-amino G, or 8-amino-I).

The relative stability of triple helices formed by the R-22 oligonucleotide derivatives and the polypyrimidine target sequence (WC-11mer) were measured spectrophotometrically at different pHs (pH 5.5–7.0). In the examples shown herein, one single transition was observed with an hyperchromicity around 25% that was assigned to the melting of the triple helix. Replacement of A and G by 8-aminoadenine ($A^N$) and 8-aminoguanine ($G^N$) in triple helix results in a high stabilization of triple helix (10–18° C. in the range from pH 5.5 to pH 7.0, see Table 2). Replacement of guanine by 8-aminohypoxanthine ($I^N$) gave only a small increase of triple helix stability at acidic pH but the triplex containing $I^N$ maintained their stability at neutral pH while the unmodified triplex decreases very fast.

TABLE 2

Melting temperatures* (° C.) for the triplex formed by R-22 derivatives and WC-11 mer.

| | | | | |
|---|---|---|---|---|
| WC-11mer | 3'CTTCCTCCTCT5' | | | |
| | SEQ ID NO:15 | | | |
| R-22 | 5'GAAGGAGAGA3'-(EG)$_6$-3'TCTCCTCCTTC5' | | | |
| | SEQ ID NO:1 | | SEQ ID NO:2 | |
| R-22A | 5'GAAGGA$^N$GGA$^N$GA3'-(EG)$_6$-3'TCTCCTCCTTC5' | | | |
| | SEQ ID NO:3 | | SEQ ID NO:2 | |
| R-22G | 5'GAAGG$^N$AGG$^N$AGA3'-(EG)$_6$-3'TCTCCTCCTTC5' | | | |
| | SEQ ID NO:4 | | SEQ ID NO:2 | |
| R-22I | 5'GAAGI$^N$AGI$^N$AGA3'-(EG)$_6$-3'TCTCCTCCTTC5' | | | |
| | SEQ ID NO:5 | | SEQ ID NO:2 | |

| Hairpin | Target | pH 5.5 | pH 6.0 | pH 6.5 | pH 7.0 |
|---|---|---|---|---|---|
| R-22 | WC-11mer | 56 | 47 | 35 | 32 |
| R-22A | WC-11mer | 62 | 56 | 48 | 46 |
| R-22G | WC-11mer | 67 | 60 | 53 | 51 |
| R-22I | WC-11mer | 54 | 47 | 40 | 38 |

*1 M NaCl, 100 mM sodium phosphate/citric acid buffer.

The relative stability of triple helices formed by the B-22 oligonucleotide derivatives and the polypyrimidine target sequence (WC-11mer) were measured. In this case the purine and pyrimidine strands are connected by their 5' ends. As before, one single transition was observed with an hyperchromicity around 25% that was assigned to the melting of the triple helix. Replacement of A by 8-aminoadenine (AN) and guanine by 8-aminoguanine (GN) in triple helix results in a high stabilization of triple helix (see Table 3) as observed previously.

TABLE 3

Melting temperatures* (° C.) for the triplex formed by B-22 derivatives and WC-11mer.

| | | | | |
|---|---|---|---|---|
| WC-11mer | 3'CTTCCTCCTCT5' | | | |
| | SEQ ID NO:2 | | | |
| R-22 | 3'TCTCCTCCTTC5'-(EG)$_6$-5'GAAGGAGGAGA3' | | | |
| | SEQ ID NO:2 | | SEQ ID NO:1 | |

TABLE 3-continued

Melting temperatures* (° C.) for the triplex formed by B-22 derivatives and WC-11mer.

| | | | | |
|---|---|---|---|---|
| R-22A | 3'TCTCCTCCTTC5'-(EG)$_6$-5'GAAGGA$^N$GGA$^N$GA3' | | | |
| | SEQ ID NO:2 | | SEQ ID NO:3 | |
| R-22G | 3'TCTCCTCCTTC5'-(EG)$_6$-5'GAAGG$^N$AGG$^N$AGA3' | | | |
| | SEQ ID NO:2 | | SEQ ID NO:4 | |

| Hairpin | Target | pH 5.5 | pH 6.0 | pH 6.5 | pH 7.0 |
|---|---|---|---|---|---|
| B-22 | WC-11mer | 54 | 45 | 33 | 20 |
| B-22A | WC-11mer | 57 | 51 | 43 | 34 |
| B-22G | WC-11mer | 69 | 59 | 50 | 40 |

*1M NaCl, 100 mM sodium phosphate/citric acid buffer

In order to check that the transition was due to triple helix formation, melting curves were performed with hairpins (R-22, R-22A, R-22G, R-22I, B-22, B-22A, B-22G) alone without the presence of the polypyrimidine target sequence (WC-11mer). In this case, a single transition was also observed but at lower temperature and with a hyperchromicity around 10–15%, indicating that the transition observed with WC-11mer (triple helix) is different from the transition observed without WC-11mer (parallel-stranded double helix). Melting temperatures are shown in Table 3.

TABLE 4

Melting temperatures* (° C.) for the R-22 and B-22 derivatives alone.

| Hairpin | pH 5.5 | pH 6.0 | pH 6.5 | pH 7.0 |
|---|---|---|---|---|
| R-22 | 34 | 25 | — | — |
| R-22A | 50 | 43 | 28 | 28 |
| R-22G | 55 | 50 | 40 | 40 |
| R-22I | 42 | 34 | 25 | 23 |
| B-22 | 35 | 25 | — | — |
| B-22A | 47 | 38 | — | — |
| B-22G | 54 | 44 | 30 | — |

*1 M NaCl, 100 mM sodium phosphate/citric acid buffer.

Figure 2:
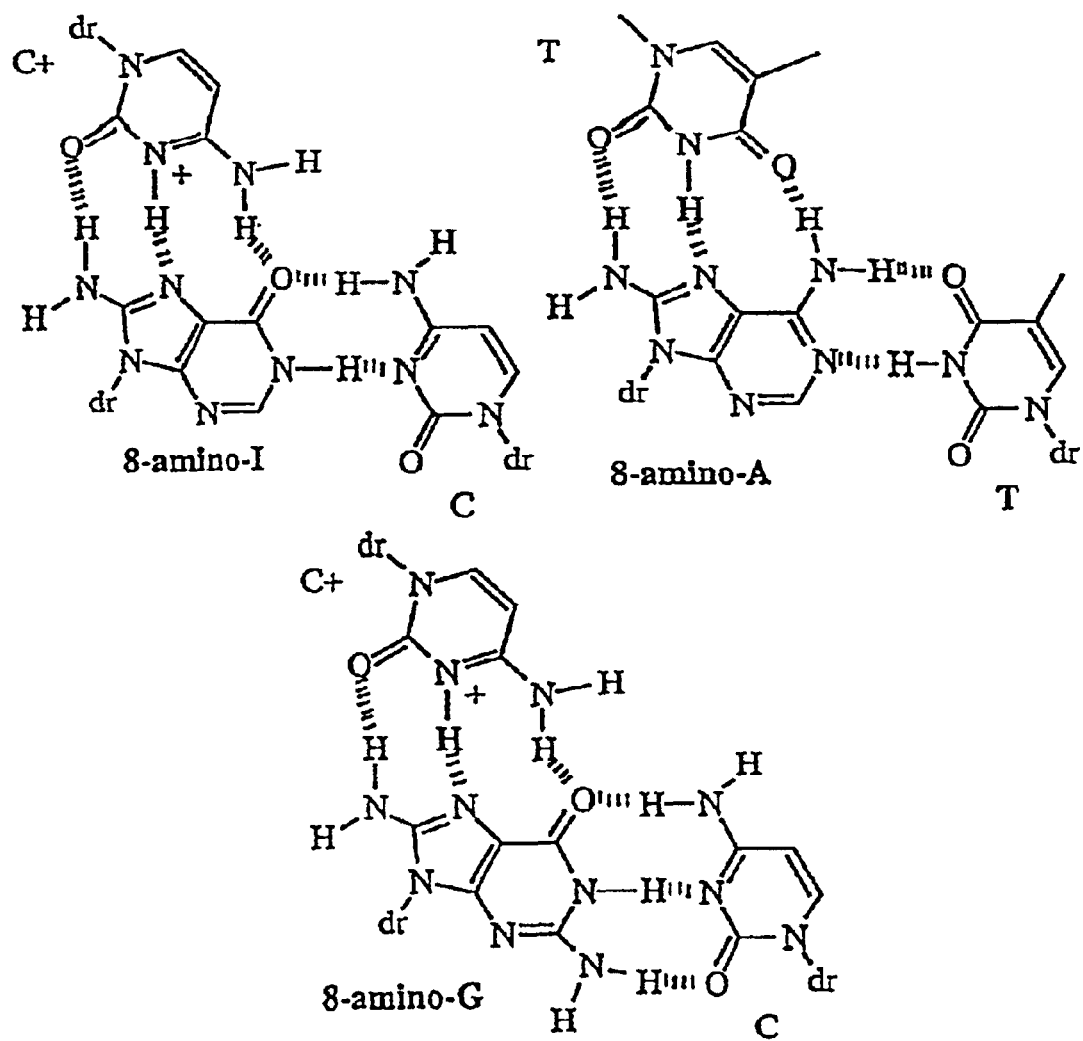
FIG. 2 is a drawing of the base-pairing of triads containing 8-aminopurines.
Figure 5:
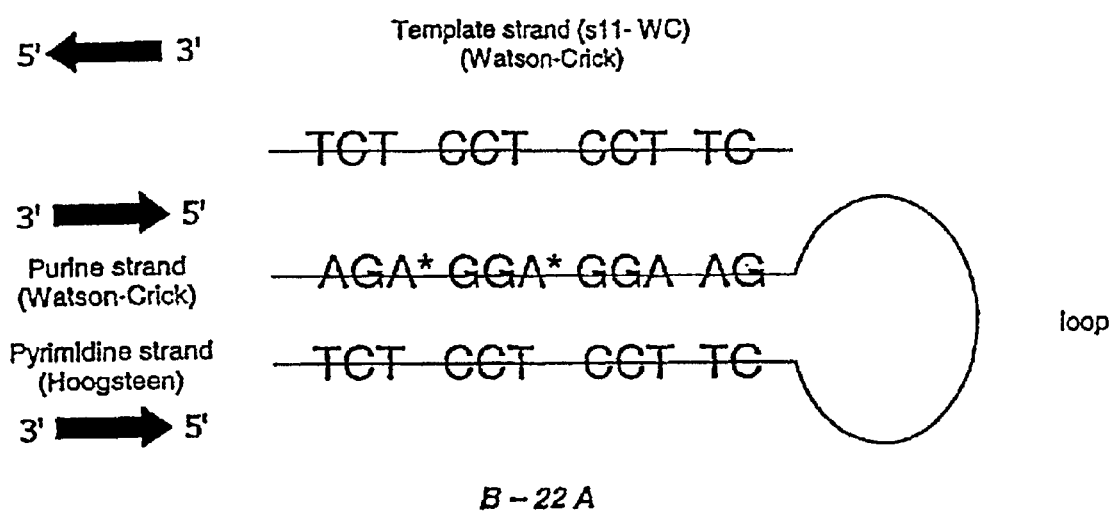
FIG. 5 is a drawing of the triplex of SEQ ID NO:2, SEQ ID NO:3, and SEQ ID NO:2, in the order listed, formed using the oligonucleotide composition, B-22A.

The transition observed without the presence of WC-11mer indicates that R22 derivatives have a parallel double-stranded structure. This structure is more stable at acidic pH and in the presence of 8-aminopurines (see Table 4). Because one of the structures observed in parallel-stranded DNA is a Hoogsteen base pair and this type of base pair will be stabilize by the presence of 8-aminopurines, it is theorized, though not wishing to be bound by any particular theory, that this type of base pair is the responsible of the stability of the parallel structure observed in R22 derivatives, in particular B-22A, (FIG. 5). Because this structure is very similar to the structure in the triple helix (see FIG. 2) the hairpin derivatives comprised in this invention have a preformed structure that will facilitate the formation of triple helices.

Figure 6:
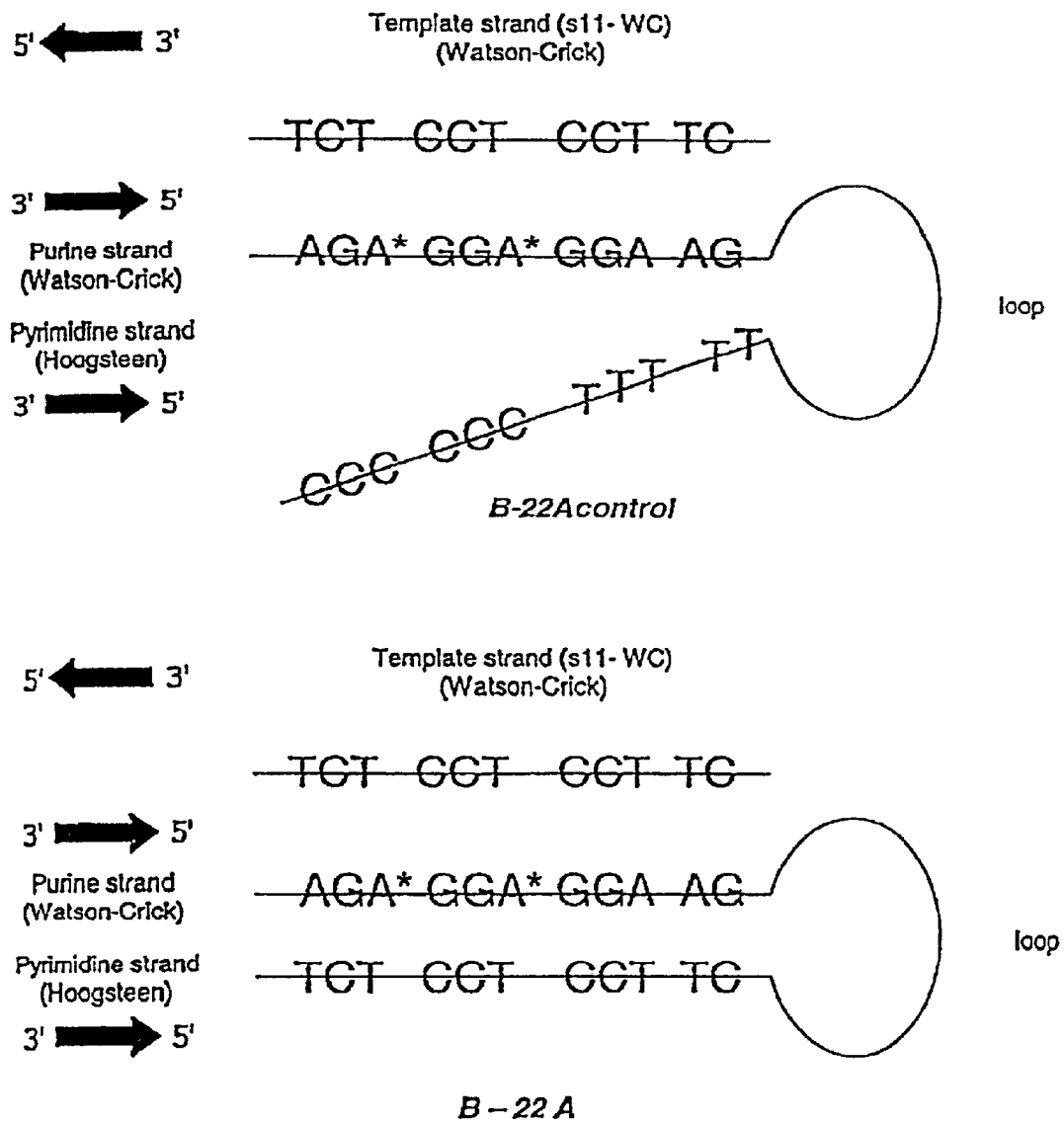
FIG. 6 is a drawing of the triplex of SEQ ID NO:2, SEQ ID NO:3, and SEQ ID NO:2, in the order listed, formed using the oligonucleotide composition, B-22A, compared to a lack of triplex formation between SEQ ID NO:2, SEQ ID NO:3, and SEQ ID NO:7 when the oligonucleotide composition B-22A control is used, where no Hoogstein bonding can occur.

The role of the Hoogsteen strand was further investigated. A hairpin probe of the same purine sequence was prepared, but with two 8-aminoadenine substitutions, and with a non-complementary pyrimidine strand. This oligonucleotide (named B-22Acontrol) can only form Watson-Crick base pair with the target sequence (WC-11mer); but no Hoogsteen bond can be formed (FIG. 6). As mentioned above, hyperchromicity is the amount by which the UV absorbance of a nucleic acid sample increases when going, for example, from a double stranded structure to a single strand structure as it melts in response to increasing temperature. A 10–15% increase is considered to correspond to the (melting) transition from a duplex to a single-stranded structure, in one step. A 15–25% increase is considered to correspond to the (melting) transition from a triplex to a single-stranded structure, in one step.

TABLE 5

Effect of the Hoogsteen strand.

| Hairpin | Target | pH 5.5, 1 M NaCl | | pH 6.0, 1 M NaCl | |
|---|---|---|---|---|---|
| | | Tm (° C.) | Hyperchromicity | Tm (° C.) | Hyperchromicity |
| B-22Acontrol | WC-11mer | 41.3 | + 12% (du to ss) | 40.0 | + 11% (du to ss) |
| B-22Acontrol | none | No transition | | No transition | |
| B-22A | WC-11mer | 57.0 | + 22% (tri to ss) | 51.0 | + 20% (tri to ss) |
| B-22A | none | 47.0 | + 12% (du to ss) | 38.0 | + 11% (du to ss) |

When the Hoogsteen strand is replaced by a non-complementary sequence, the structure of parallel duplex is not observed anymore, as indicated by the disappearance of the transition observed when the melting curve is performed without the target WC-11mer.

The transitions observed with the duplexes formed by B22-Acontrol: WC-11mer have lower Tm and lower hyperchromicity.

The hyperchromicity associated with the transition of duplex formed by B-22Acontrol : WC-11mer is around 11%, which indicates a transition of duplex to single-stranded.

The transitions observed with the complex formed by B22A : WC-11mer have a 22% hyperchromicity typical of a is transition from triplex to single-stranded. The difference between the Tm of B-22Acontrol duplex and B-22A triplex is the gain obtained by the addition of a complementary Hoogsteen strand. At pH 6.0, this difference is 11° C. (1.0 degree per base) and, at pH 5.5, is 16° C. (1.4 degree per base).

The effect of the salts at pH 6.0 were studied. The triplex formed by hairpin having two 8-aminoadenines ($A^N$) and WC-11mer were used as well as the triplex formed by the hairpin having two 8-aminoguanines ($G^N$) and WC-11mer. The effect of the concentration of NaCl, $MgCl_2$, and spermine on the stability of the triplex was studied. Previous reports on triplexes showed an increased stabilization of triplexes by the addition of magnesium and spermine. See reference 2. The effect of these salts on a triplex is shown in the following tables. In the case of NaCl, the buffer used was 0.1 M sodium phosphate-citric acid pH 6.0. In the cases of $MgCl_2$ and spermine, the buffer used was 0.1 M sodium phosphate pH 6.0.

TABLE 6

Effect of the NaCl.

| hairpin | target | [NaCl] | Tm (° C.) |
|---|---|---|---|
| B-22A | WC-11mer | 0 | 48.9 |
| B-22A | WC-11mer | 0.1 M | 50 |
| B-22A | WC-11mer | 1 M | 51 |

0.1 M sodium phosphate-citric acid pH 6.0

TABLE 7

Effect of the $MgCl_2$

| hairpin | target | [$MgCl_2$] | Tm (° C.) |
|---|---|---|---|
| B-22A | WC-11mer | 0 | 53.2 |
| B-22A | WC-11mer | 10 mM | 58.5 |
| B-22A | WC-11mer | 50 mM | 58.4 |
| B-22G | WC-11mer | 0 | 57.6 |
| B-22G | WC-11mer | 10 mM | 62.8 |
| B-22G | WC-11mer | 50 mM | 63.4 |

0.1 M sodium phosphate pH 6.0

TABLE 8

Effect of spermine

| hairpin | target | [spermine] | Tm (° C.) |
|---|---|---|---|
| B-22G | WC-11mer | 0 | 57.6 |
| B-22G | WC-11mer | 1 mM | 60.3 |
| B-22G | WC-11mer | 5 mM | 59.6 |

0.1 M sodium phosphate pH 6.0

Sodium chloride had a small stabilization effect (from 48.9° C. (no NaCl) to 51° C. (1M NaCl)). Low concentrations of magnesium chloride stabilized the triplex, for example the melting temperature of triplex B-22G: WC-11mer and B-22A: WC-11mer increases 5 degrees from no $MgCl_2$ to 10 mM $MgCl_2$. Going from 10 mM to 50 mM $MgCl_2$ the increase on the melting temperature was none or less than one degree. At pH 6 adding more magnesium than 50 mM resulted in precipitation of magnesium oxide during the heating. In conclusion, the presence of the magnesium is beneficial for the stability of triplex, with 10 mM the optimal concentration. Spermine had a small stabilizing effect on the stability of the triplexes.

Next, the stabilization properties of 8-aminoadenine and 8-aminoguanine were studied to see if the effects were additive. A hairpin with two 8-aminoadenines and two 8-aminoguanines substitutions was prepared. Melting curves were performed with the following hairpins and the target WC-11mer at pH 6.0, 0.1 M sodium phosphate, 1 M NaCl.

| | | |
|---|---|---|
| B-22 | 3'AGAGGAGGAAG5'-(EG)6-5'CTTCCTCCTCT3' | Tm = 45.0° C. |
| | SEQ ID NO:1      SEQ ID NO:2 | |
| B-22A | 3'AGA^NGGA^NGGAAG5'-(EG)6-5'CTTCCTCCTCT3' | Tm = 51° C. |
| | SEQ ID NO:3      SEQ ID NO:2 | |
| B-22G | 3'AGAG^NGAG^NGAAG5'-(EG)6-5'CTTCCTCCTCT3' | Tm = 59° C. |
| | SEQ ID NO:4      SEQ ID NO:2 | |
| B-22AG | 3'AGA^NG^NGA^NG^NGAAG5'-(EG)6-5'CTTCCTCCTCT3' | Tm = 65.4° C. |
| | SEQ ID NO:6      SEQ ID NO:2 | |

The stabilization properties of the 8-aminopurines were additive. The addition of the two 8-aminoguanines and two 8-aminoadenines increased the melting temperature by 20° C., while the increase on the melting temperature induced by two 8-aminoadenine was 6° C., and the increase induced by two 8-aminoguanines was 14° C.

Next, the effect of an interruption on the polypyriridine target was measured. To this end two polypyrimidine targets with a purine (A or G) in the middle of the sequence were prepared ($s_{11}$-MM: 5'TCTCCTGCTTC3' (SEQ ID NO: 16) and $s_{11}$-MMT: 5'TCTCCTACTTC3' (SEQ ID NO:23)). Next, hairpins carrying two 8-aminoadenines were designed (see below). Five hairpins have a C opposite to the G of $s_{11}$-MM and one of the four natural bases or propanediol on the Hoogsteen strand opposite to the C:G interruption. Another five hairpins have a T opposite to the A of $s_{11}$-MMT and one of the four natural bases or propanediol on the Hoogsteen strand opposite to the T:A interruption. Melting curves were performed at pH 6.0, 0.1 M sodium phosphate, 1 M NaCl.

| Hairpins | |
|---|---|
| B-22A: | 3'AGA^NGGA^NGGAAG5'-(EG)6-5'CTTCCTCCTCT3' |
| | SEQ ID NO:3      SEQ ID NO:2 |
| B-22AMMC: | 3'AGA^NGGA^NCGAAG5'-(EG)6-5'CTTCCTCCTCT3' |
| | SEQ ID NO:8      SEQ ID NO:2 |
| B-22AMMT: | 3'AGA^NGGA^NCGAAG5'-(EG)6-5'CTTCTTCCTCT3' |
| | SEQ ID NO:8      SEQ ID NO:9 |
| B-22AMMG: | 3'AGA^NGGA^NCGAAG5'-(EG)6-5'CTTCGTCCTCT3' |
| | SEQ ID NO:8      SEQ ID NO:20 |
| B-22AMMA: | 3'AGA^NGGA^NCGAAG5'-(EG)6-5'CTTCATCCTCT3' |
| | SEQ ID NO:8      SEQ ID NO:21 |
| B-22AMMpd: | 3'AGA^NGGA^NCGAAG5'-(EG)6-5'CTTCpdTCCTCT3' |
| | SEQ ID NO:8      SEQ ID NO:22 |

Target oligonucleotide
Target 1: WC-11 5'TCTCCTCCTTC3' (SEQIDNO:15)
Target 2: $s_{11}$-MM 5'TCTCCTGCTTC3' (SEQ ID NO:16)

| hairpin | Target 1 Triad 1 | WC-11 Tm (° C.) | Target 2 Triad 2 | s11-MM Tm (° C.) |
|---|---|---|---|---|
| B-22A | C.G-C | 51 | G.G-C | 43 |
| B-22AMMC | C.C-C | 33 | G.C-C | 47 |
| B-22AMMT | C.C-T | 30 | G.C-T | 45 |
| B-22AMMG | C.C-G | 34 | G.C-G | 43 |
| B-22AMMA | C.C-A | 28 | G.C-A | 41 |
| B-22AMMpd | C.C-pd | 29 | G.C-pd | 44 |

The introduction of an interruption on the polypyrimidine-polypurine track was studied. A guanine was introduced on the polypyrimidine target instead of a cytosine. An hairpin with two 8-aminopurines was designed in where a cytosine was located in the purine part opposite to the cytosine. The hairpin that had a cytosine in the Hoogsteen pyrimidine part gave the best binding. The hairpin B-22AMMC was able to bind to its target ($s_{11}$-MM) although there is a decrease of 4 degrees on the Tm (47° C. B-22AMMC: $s_{11}$-MM compared with 51° C. B-22A: WC-11mer). The binding of the new hairpin to its new target is very selective as judged by the big decrease observed on the Tm of the triplex B-22AMMC with the old target (33° C. B-22AMMC: WC-11mer versus 47° C. B-22AMMC: $s_{11}$-MM). As conclusion the oligomers described in this report are able to be redesigned to cope with the presence of interruptions on the polypurine-polypyrimidine tracks.

A similar result was observed when an adenine was introduced in the polypyrirdine target (see below).

| Hairpins | |
|---|---|
| B-22A: | 3'AGA^NGGA^NGGAAG5'-(EG)6-5'CTTCCTCCTCT3' |
| | SEQ ID NO:3      SEQ ID NO:2 |
| B-22AMMCA: | 3'AGA^NGGA^NTGAAG5'-(EG)6-5'CTTCCTCCTCT3' |
| | SEQ ID NO:19      SEQ ID NO:2 |
| B-22AMMTA: | 3'AGA^NGGA^NTGAAG5'-(EG)6-5'CTTCTTCCTCT3' |
| | SEQ ID NO19      SEQ ID NO:9 |
| B-22AMMGA: | 3'AGA^NGGA^NTGAAG5'-(EG)6-5'CTTCGTCCTCT3' |
| | SEQ ID NO:19      SEQ ID NO:20 |
| B-22AMMAA: | 3'AGA^NGGA^NTGAAG5'-(EG)6-5'CTTCATCCTCT3' |
| | SEQ ID NO:19      SEQ ID NO:21 |

Targets
Target 1: WC-11mer 5'TCTCCTCCTTC3' (SEQ ID NO:15)
Target 2: $s_{11}$-MMT 5'TCTCCTACTTC3' (SEQ ID NO:23)

| Hairpin | Target 1 Triad 1 | WC-11 Tm (° C.) | Target 2 Triad 2 | s11-MMA Tm (° C.) |
|---|---|---|---|---|
| B-22A | C.G-C | 51 | G.G-C | 43 |
| B-22AMMTC | C.T-C | 28 | A.T-C | 39 |
| B-22AMMTT | C.T-T | 31 | A.T-T | 40 |
| B-22AMMTG | C.T-G | 33 | A.T-G | 46 |
| B-22AMMTA | C.T-A | 31 | A.T-A | 40 |
| B-22AMMTp | C.T-pd | 30 | A.T-pd | 42 |

In this case the best base on the Hoogsteen position was G (Tm=46° C. B-22AMMTG: $s_{11}$-MMA compared with 51° C. B-22A: WC-11mer). As described before, the binding of the new hairpin to its new target is very selective as judged by the big decrease observed on the Tm of the triplex B-22AMMTG with the old target (33° C. B-22AMMTG: WC-11mer versus 46° C. B-22AMMTG: $s_{11}$-MMA). As described before, the oligomers described in this report are able to be redesigned to cope with the presence of interruptions on the polypurine-polypyrimidine tracks.

Finally, the role of the loop on the stability of the triplex was analysed by preparing derivatives of B-22A with different loops. In addition to the hexaethyleneglycol linker, the nucleotide loops -TTTT-(SEQ ID NO:13) and -GGAGG-(SEQ ID NO:14) were studied. See reference 41. Two tetrathymine loops were prepared: one on reversed orientation than the purine strand (B-22ALT1) and the second on the same orientation than the purine strand (B-22ALT2). The GGAGG (SEQ ID NO:14) loop was on the same orientation than the purine strand (B-22ALGA). Melting curves were performed with the following hairpins and the target WC-11mer at pH 6.0, 0.1 M sodium phosphate, 1 M NaCl.

| # | Sequence | | Tm (° C.) |
|---|---|---|---|
| B-22A | 3'AGA<sup>N</sup>GGA<sup>N</sup>GGAAG5'-(EG)<sub>6</sub>-5'CTTCCTCCTCT3' | | 51 |
| | SEQ ID NO:3 | SEQ ID NO:2 | |
| B-22-ALT1 | 3'AGA<sup>N</sup>GGA<sup>N</sup>GGAAG5'-5'TTTT-CTTCCTCCTCT3' | | 57 |
| | SEQ ID NO:3 | SEQ ID NO:10 | |
| B-22ALT2 | 3'AGA<sup>N</sup>GGA<sup>N</sup>GGAAG-TTTT5'-5'CTTCCTCCTCT3' | | 55 |
| | SEQ ID NO:11 | SEQ ID NO:2 | |
| B-22ALTGA | 3'AGA<sup>N</sup>GGA<sup>N</sup>GGAAG-GGAGG5'-5'CTTCCTCCTCT3' | | 54 |
| | SEQ ID NO:12 | SEQ ID NO:2 | |

These embodiments of nucleotide loops created more stability of the triplex than the hexaethyleneglycol linker. Best results were obtained with the reversed TTTT (SEQ ID NO: 13) linker (hairpin B-22ALT1, an increased on Tm of 6 degrees), followed by the TTTT (SEQ ID NO:13)linker (hairpin B-22ALT2, ΔTm 4 degrees) and the GGAGG (SEQ ID NO:14) linker (hairpin B-22ALGA, ΔTm 3 degrees).

Binding of hairpins to target were also analysed by gel-shift experiments. In these experiments the target was labelled radioactively with [γ-$^{32}$P]-ATP and polynucleotide kinase and increasing amounts of the hairpins were added to a solution of the labelled target. After incubation at room temperature for 30 min-1 hr the mixtures were analysed by polyacrylamide gel electrophoresis. The formation of the triplex was followed by the appearance of a radioactive band with less mobility than the band corresponding to the target alone. One experiment used the binding of hairpin R-22G to target WC-11mer and to a double-stranded target consisting of an equimolar mixture of target WC-11mer (5'TCTCCTCCTTC3' (SEQ ID NO:15)) and its complementary purine strand (3'AGAGGAGGAAG5' (SEQ ID NO:1)) at pH 7.0. When the labelled oligonucleotide is the target pyrimidine strand (WC-11mer) the appearance of a new radioactive band with lower mobility is observed in both single and double-stranded targets indicating the formation of the triplex. On the contrary when the labelled oligonucleotide is the purine strand no new band is observed indicating that the binding of hairpins only occurred to the target pyrimidine strand.

Methods of Use of Hairpins

The present invention further comprises compositions and methods for the detection of nucleic acid sequences. These methods include automation procedures for rapid screening and diagnostic applications. One embodiment of the present invention is the use of one or more hairpin structures that hybridize to a nucleic acids to form triplex structures. The present invention also comprises hybridization of multiple hairpins that, for example, can distort the structure of the nucleic acid and allow for interactions such as intercalating agents, binding of other probes or restriction of the unbound or distorted areas.

In a preferred method, two hairpin probes are hybridized to one strand of the double-stranded DNA so that the probes flank the target sequence on both sides and form two triplex structures. These two triplex structures force the ds DNA to "breathe" open between the triplex structures and allow for binding of other nucleotide structures or probes within this region, if required by a particular method. See FIG. 21A and B, which illustrates an embodiment of the triplex formed by addition of self-annealing probes to ds DNA. Two hairpin structures are used to form two triplex regions, and one of the hairpin structures is used as a capture molecule, in which the loop portion has a peptide attached that can be bound by a specific antibody. The capture molecule is a magnetic bead attached to the loop portion of the hairpin structure and the reporter probe is detected using a monoclonal antibody that is recognized by a second antibody that is labeled using a liposome filled with a fluorophore. The entire reacted structure is detected using an antibody that is labeled using a liposome filled with a fluorophore.

A preferred embodiment comprises methods and compositions involving hybridization of at least one hairpin probe that comprises a 5' to 3' purine sequence, followed by a loop sequence, followed by a 3' to 5' pyrimidine sequence that is complementary to the purine sequence, as shown in FIG. 3. The loop sequence comprises any sequence that will not hybridize to itself. The loop may be of any sequence or include any number of nucleotides, preferably four thymidine resides, or a six-member ethylene glycol chain. The ethylene glycol chain can be derivatized to allow for attachment of different molecules. Preferably, the purine and pyrimidine sequences are approximately eleven nucleotides each. The pyrimidine sequence may be synthesized using reverse phosphoramidites.

In some embodiments, at least one of the hairpin probes is labeled with a peptide, preferably a hexapeptide, comprising a known amino acid sequence. Antibodies, that are specific for this amino acid sequence, are attached to magnetic beads. The binding of the antibody and the peptide binding partner allows for the capture of the DNA target comprising the triplex structures. In another embodiment, the loop structure of the hairpin probe is attached directly to a magnetic bead for capture. The antibodies used may be monoclonal, polyclonal or antibody fragments. Additionally, other specific binding partner pairs, such as those known in the art, can be used with the present invention.

Figure 21A:
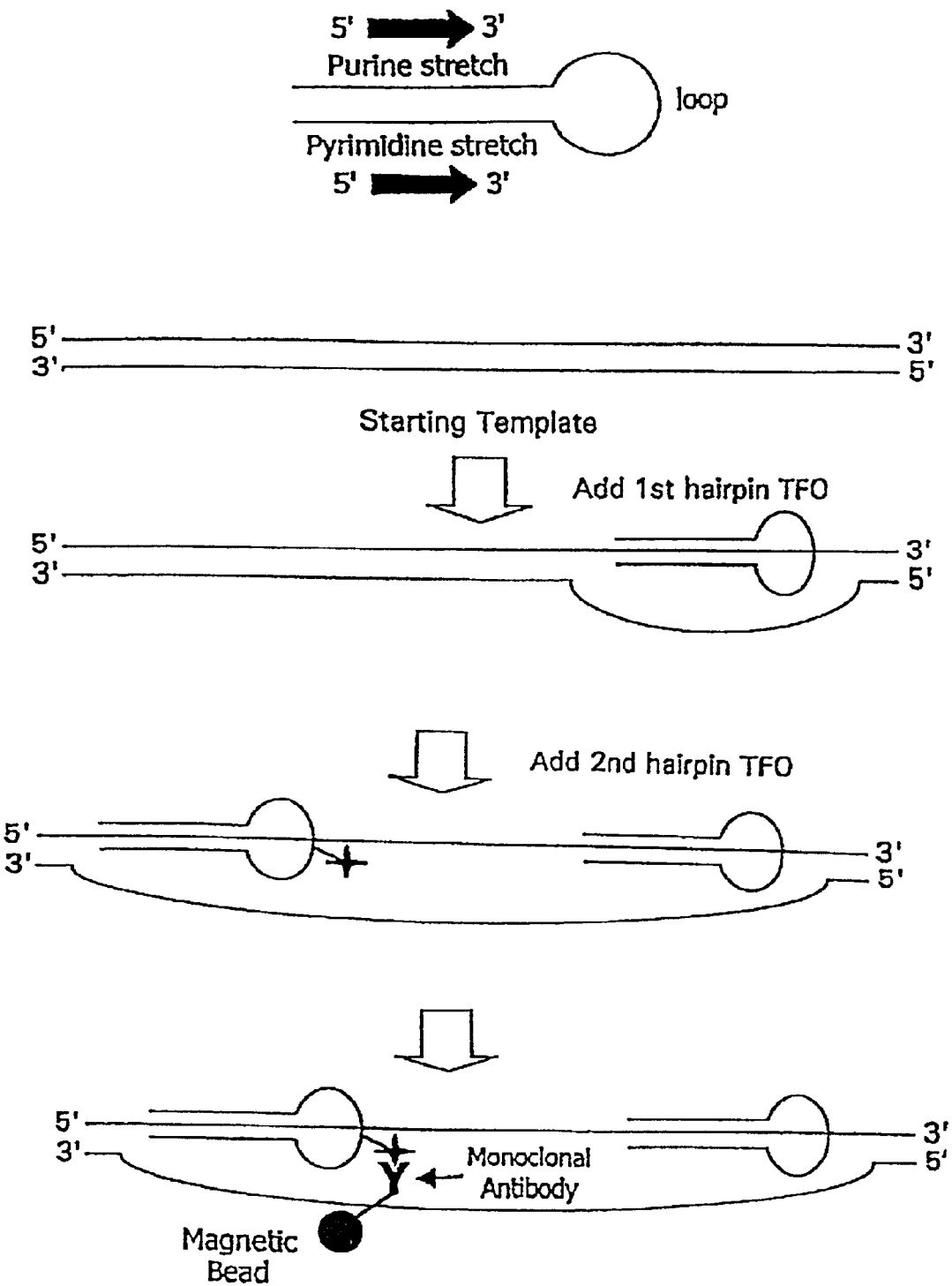
FIGS. 21A and B show embodiments of the methods of the present invention using the triplex forming oligonucleotides and detection of the structures formed.
Figure 21B:
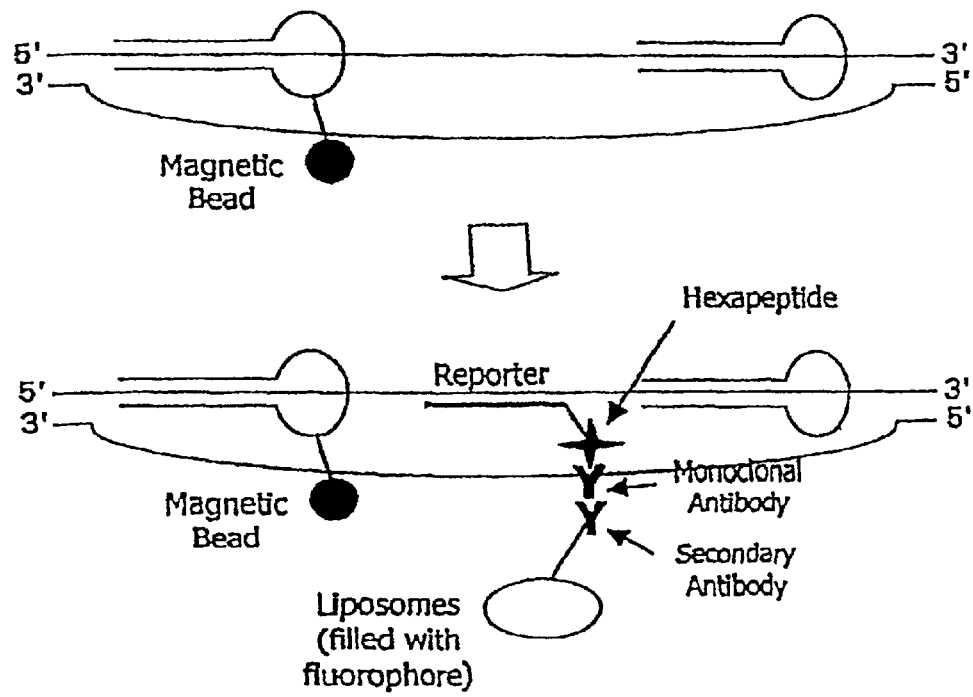
Figure 21B:
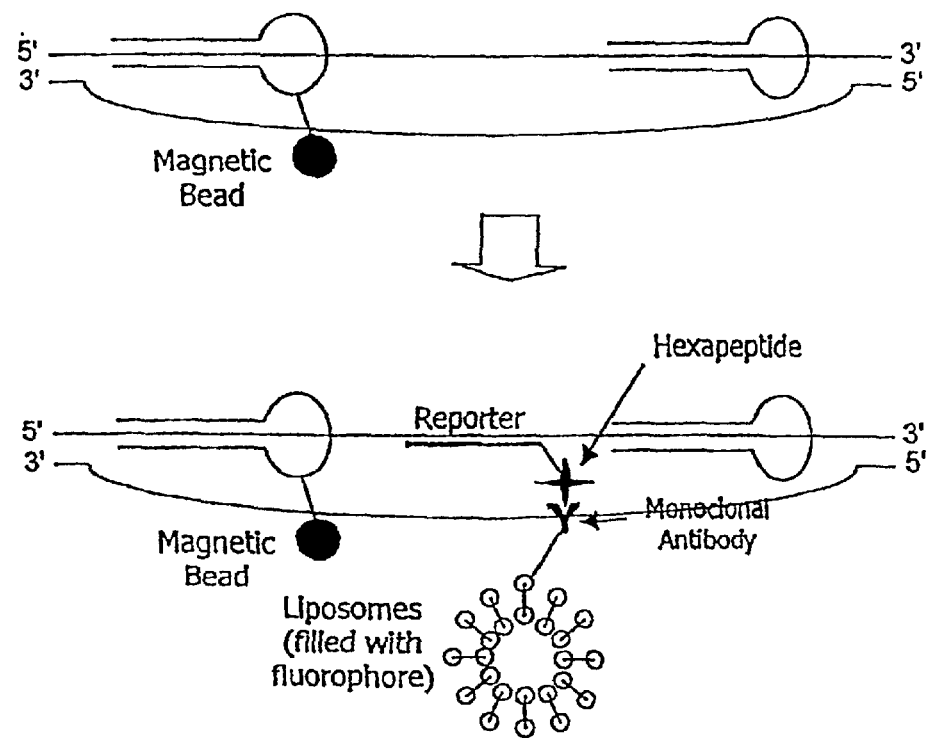
Figure 22:
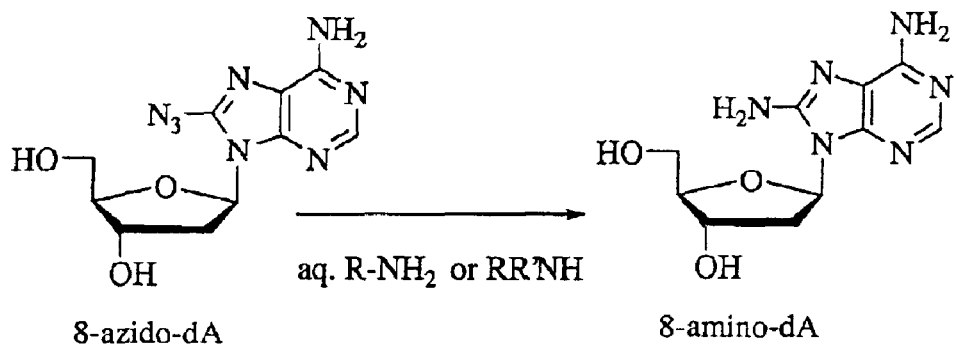
FIG. 22 is a reaction scheme to produce 8-amino-2'deoxyadenosine.
Figure 23:
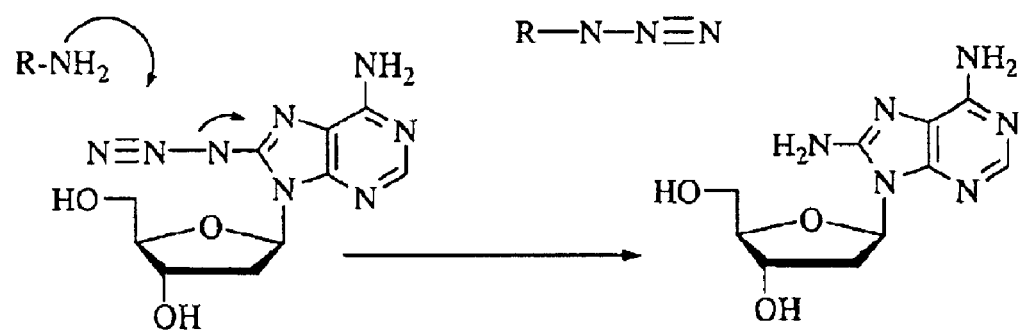
FIG. 23 is a tentative reaction scheme illustrating an attack of the amino to the azido group to yield an azido derivative and 8-amino-2-deoxyadenosine.
Figure 24:
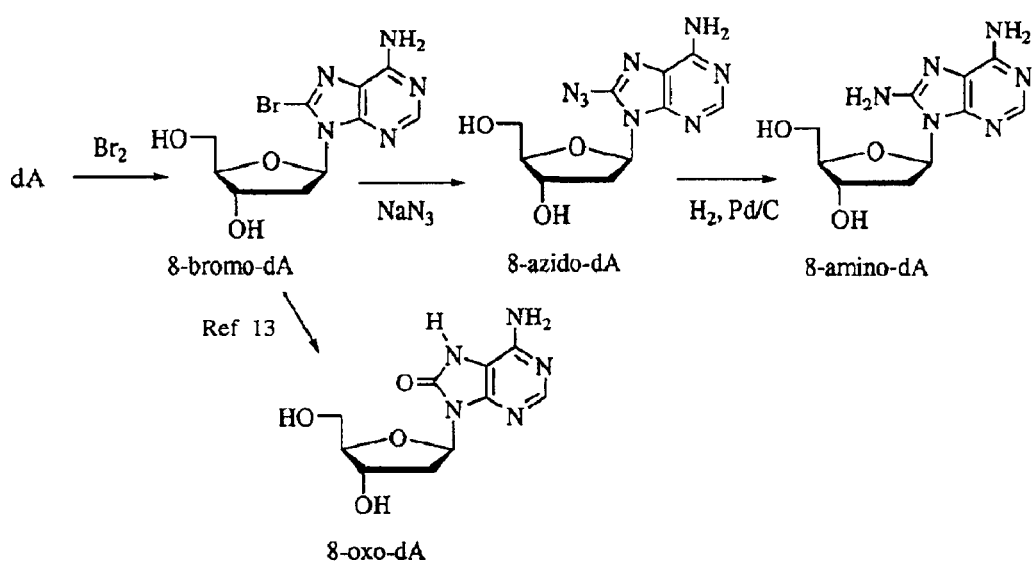
FIG. 24 is a reaction scheme to produce 8-amino-2'deoxyadenosine employing a hydrogation reaction.

Once captured, the DNA target can be detected by any of the numerous detection systems known to those skilled in the art. A novel detection system comprises use of a single-stranded reporter probe that binds between the two triplex formations, as shown in FIG. 21A and B. The reporter comprises a nucleic acid sequence that has a peptide attached to it that can be detected by a first antibody. A second antibody, specific for the first antibody, is attached to a liposome filled with a fluorophore. Upon addition of the complement cascade proteins, the liposome could be lysed and the fluorophore released and thus, detected.

In another preferred embodiment, the detection step may comprise binding of a single-stranded reporter probe having a peptide, preferably a hexapeptide, attached. The presence of the peptide is detected using an antibody to the peptide that is complexed with a liposome. The liposome is filled with a chosen fluorophore and modified at a very low and limited number of sites with the antibody specific for the peptide of the reporter probe.

The liposomes of the present invention may comprise different substrates and the outer surfaces may be modified using methods known to those skilled in the art, such as modification methods involving, but not limited to, thiol groups or amino groups. Monoclonal antibodies or polyclonal antibodies or antibody fragments could be attached to such liposomes. Preferably, four to five antibody molecules per liposome are used.

Any liposome that can be filled with a detectable agent can be used in the present invention. Depending on the nature of the substrate of the liposome, the liposome can be filled with the detectable agent using a variety of methods. One method is passive diffusion. For example, a liposome of approximately 50 nm in diameter will take up 30 to 40 molecules of carboxy-fluorescein. Larger liposomes, such as those having diameters of approximately 150 nm, can take up more detectable agent molecules. With one reporter probe, there would be a minimum of 30-fold signal amplification with 50 nm liposomes, over the use of a single detectable molecule attached to a reporter probe.

Once the capture step and all the wash steps are completed, it is not critical that the bound structures are kept intact. At that point, the liposomes could be lysed by any method to release the detectable agents. For example, mild conditions, such as those using ionic detergents could be used to open the liposome channels and release the detectable agent.

The present invention also comprises multiplexing. Such methods and compositions may be used with heterozygous samples and or SNPs by using reporter probes of different sequence specificity and attached to different peptides. Each peptide/probe would be detected by a different antibody attached to a liposome carrying a detectable agent that is not carried by any other liposome. It is preferred that the detectable agents do not interfere with one another.

Hybridization Properties of 8amino-2'-deoxyinosine

In the recent years, interest has focused on base analogues which may form base pairs with the four natural bases. 2'-deoxyinosine is one of the most successfully used. See references 44–49. Due to the structural similarity of 8-amino-2'-deoxyinosine to 2'-deoxyinosine, the hybridisation properties of 8-amino-2'-deoxyinosine were measured spectrophotometrically. Pentadecanucleotide duplexes carrying at the central position all possible base pairs between 8-aminohypoxanthine ($I^N$) or hypoxanthine (I) with the four natural bases were prepared. The melting temperatures of the transition duplex to coil of duplexes containing 8-amino-2'-deoxyinosine or 2'-deoxyinosine opposite the four natural bases are shown in Table 9.

TABLE 9

Melting temperatures (° C.) of duplexes carrying 8-amino-hypoxanthine ($I^N$) and hypoxanthine (I) measured at 0.15 M NaCl, 50 mM Tris-HCl buffer pH 7.5.

5' TAGAGGXTCCATTGC 3' (SEQ ID NO:17)

3' ATCTCCYAGGTAACG 5' (SEQ ID NO:18)

|  | X = $I^N$ | X = I |
|---|---|---|
| Y = C | 56 | 58 |
| Y = A | 53 | 55 |
| Y = G | 54 | 53 |
| Y = T | 53 | 52 |

Melting temperatures of duplexes carrying 8-aminohypoxanthine were between 53–56° C. (3 degrees of difference) while duplexes carrying hypoxanthine were between 52–58° C. (6 to degrees of difference) indicating that 8-amino-2'-deoxyinosine is a good alternative to 2"deoxyinosine as universal base at ambiguous positions in DNA primers and probes.

Figure 7A:
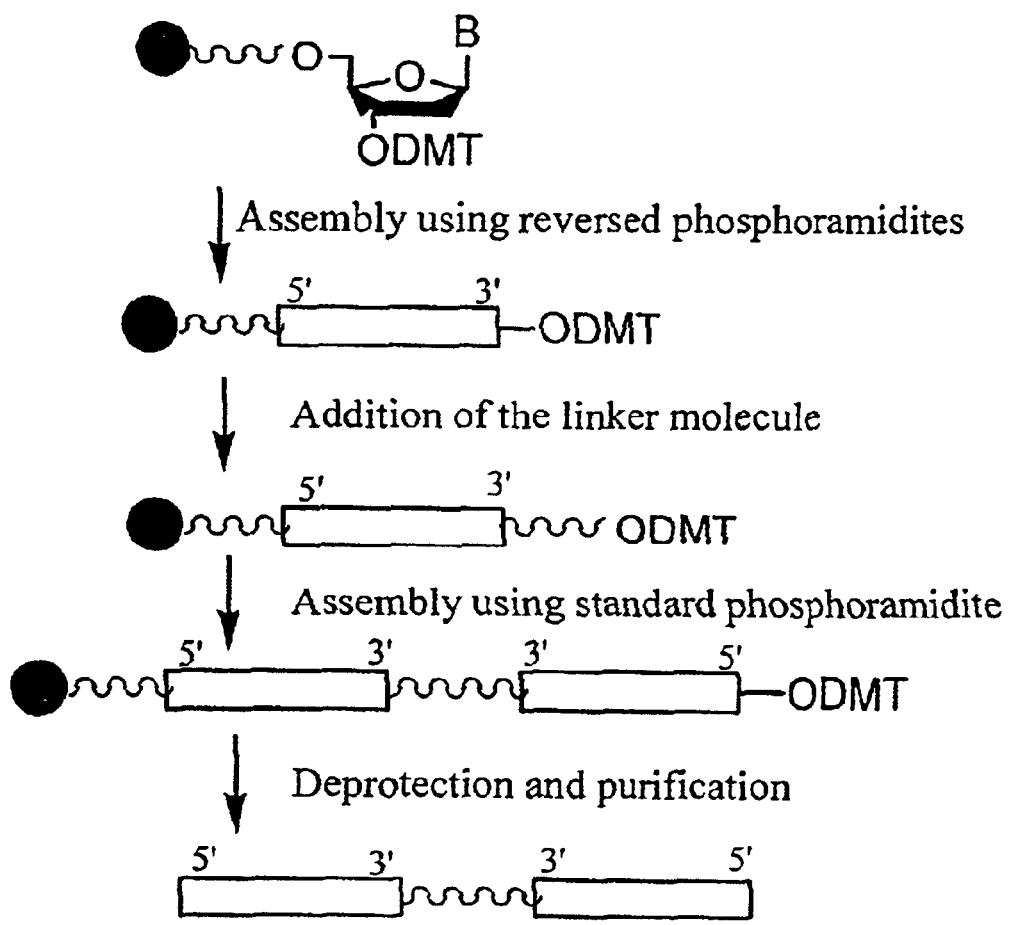
FIGS. 7A and B are drawings of procedures to produce 3'-3' (a) or 5'-5' (b) linker attached oligonucleotides.
Figure 7B:
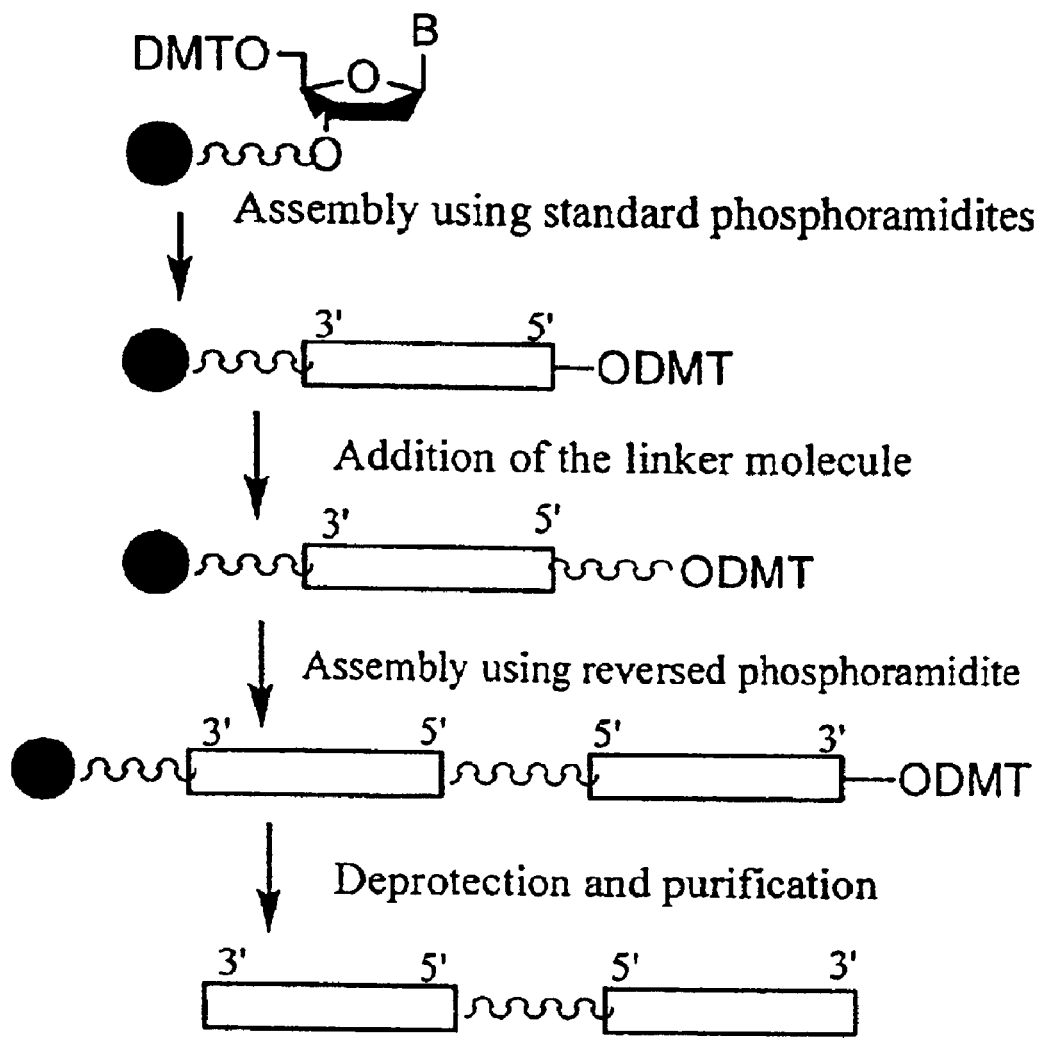

The present invention also comprises compositions and methods of making parallel stranded oligonucleotides. Such methods comprise use of spacer arms and oligonucleotides that may comprise any number of bases. The synthesis of 3'-3' or 5'-5' attached oligonucleotides is described herein. The oligonucleotides may have the same or different sequences of nucleotides. Oligonucleotide synthesis is usually carried out from the 3' to the 5' terminus. However, in some cases it is necessary to synthesize oligonucleotides in the opposite sense (5' to 3'). Modifing the terminal linkages from the natural 3'-5' to 3'-3' and/or 5'-5' results in an increased resistance in those oligonucleotides against exonuclease activity, especially 3'-exonuclease activity. A general scheme for making the linkers is shown in FIG. 7. Synthesis of the Spacer Arm: 1.3 bis (dimethoxytrityl) propane-1,2,3-triol.

Glycerol was used as starting material for the preparation of this spacer arm, but any compound with the structure shown below can be used with good results.
Structure of Starting Material for Spacer Arms

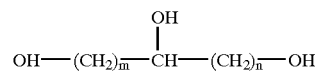

Figure 8:
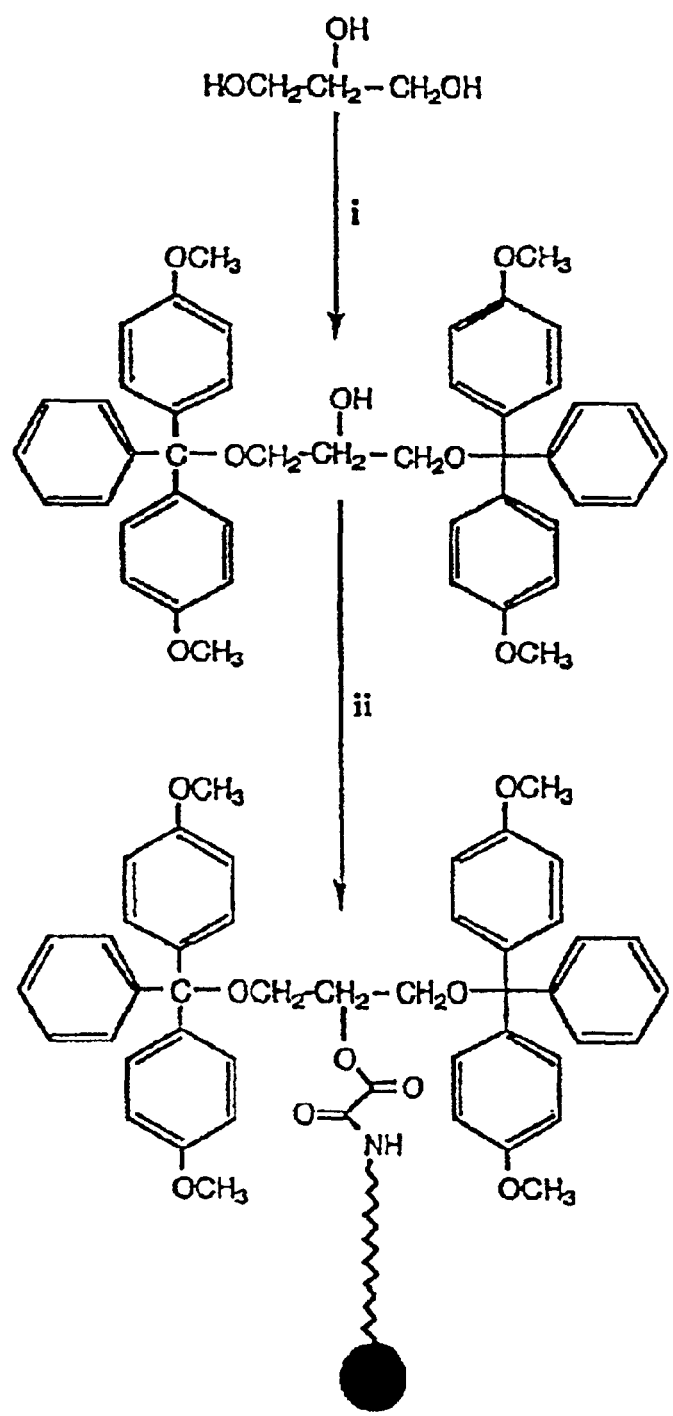
FIG. 8 is a drawing of the synthesis steps of the glycerol-spacer arm (S).

The procedure to prepare the glycerol-spacer arm (S)* is shown in FIG. 8. (S*-symmetrical). The glycerol spacer arm was attached to the LCAA-CPG using the oxalyl linker. The oxalyl can be replaced by succinyl or sarcosyl spacer arms. As shown in FIG. 8, i) is the reaction of dimethoxytrityl chloride in pyridine, ii) are the reactions a) oxalyl chloride and 1,2,4-triazole in acetonitrile, b) LCAA-CPG (long chain alkylamino-controlled pore glass); c) dimethylaminopyridine (DMAP), acetic anhydride, TMF (tetaahydrofuran).

The first step of the synthesis consisted of the selective protection of the primary hydroxyl function. The protected product was dissolved in acetonitrile/pyridine (2:1) and then added to a previously prepared mixture of oxalyl chloride and 1,2,4-triazole in anhydrous acetonitrile. After 1 hour the solution was transferred to a gastight syringe containing the LCAA-CPG and the reaction was allowed to proceed for 30 minutes. The liquid was ejected from the syringe and the solid support washed successively with acetonitrile, anhydrous methanol (to cap residual oxalyl triazolide groups) and acetonitrile.

To acetylate underivatized amino groups from further reaction the solid support was treated with an equivolume mixture of tetrahydrofuran (THF) solutions of DMPA and acetic anhydride for 30 minutes. At the end, the support was washed with pyridine, acetonitrile and diethyl ether, air dried and then dried in vacuo.

Synthesis of the 3'-3' and 5'-5' Attached Oliponucleotides with Identical Sequences.

Figure 9A:
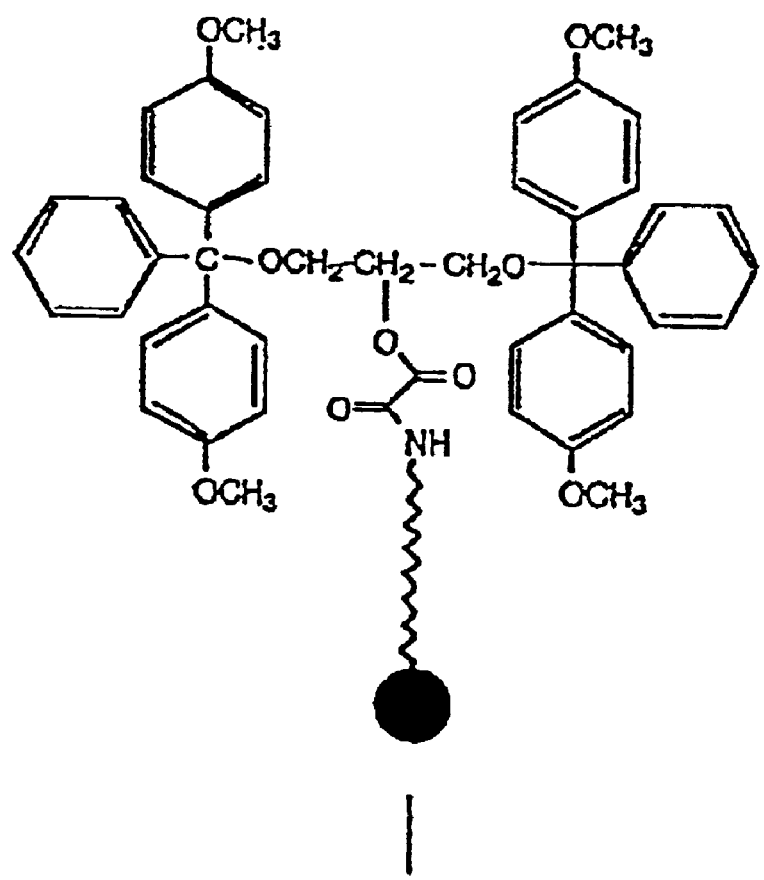
FIGS. 9A and B is a drawing of the synthesis of the 5'-5' and 3'-3' attached oligonucleotides.
Figure 9B:
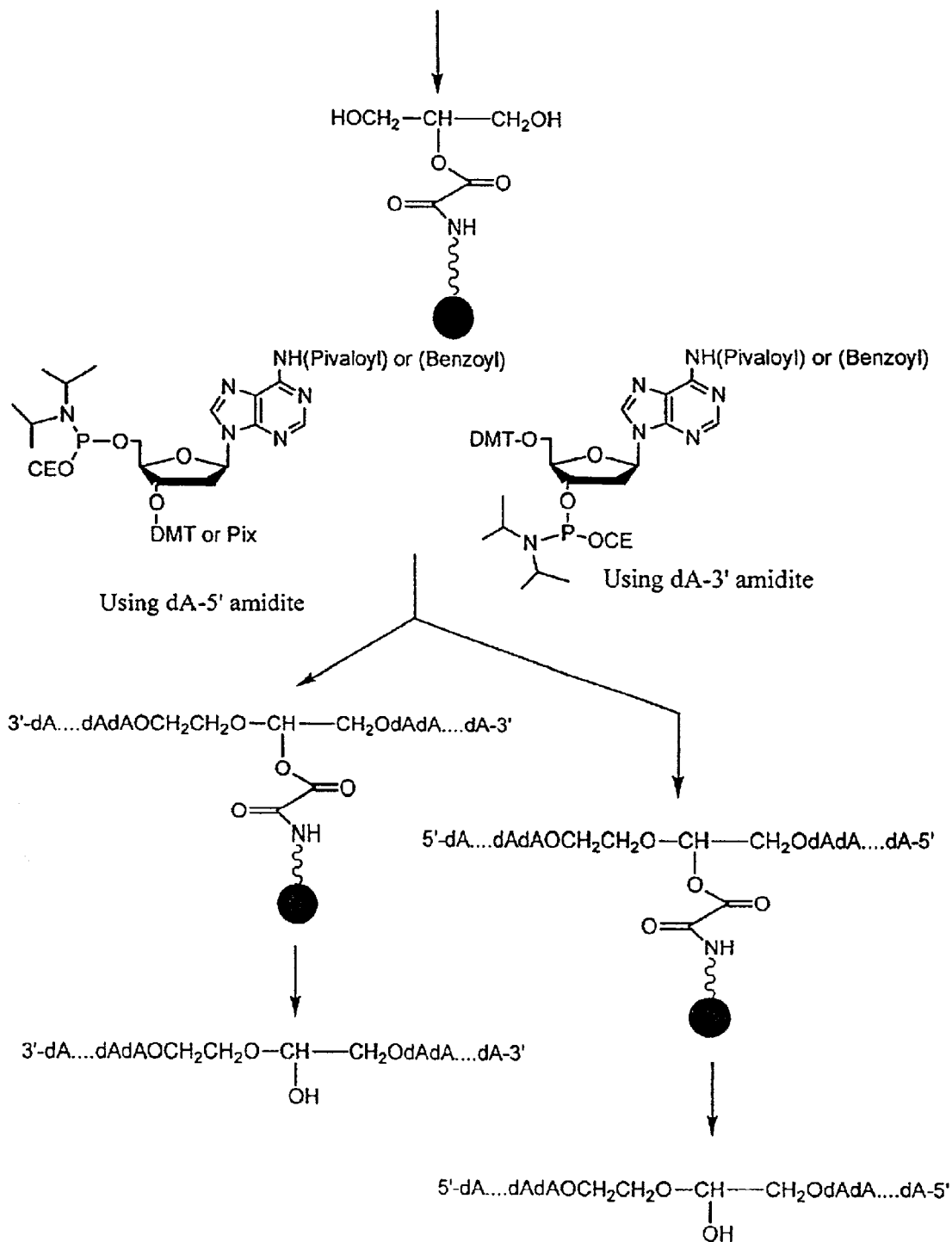

3'-3' and 5'-5' attached oligonucleotides with identical sequences were prepared on an automatic DNA synthesizer using the glycerol spacer arm (S)-LCAA-CPG and standard or reversed 2-cyanocthyl phosphoramidite chemistry (FIGS. 9A & B). Oligonucleotides were synthesized with the last DMT group on to help reverse-phase HPLC-purification. After the assembly of the sequences, the oligonucleotides were cleaved from the support by a treatment of 32% aqueous ammonia at 55° C. for 16 hours. Ammonia solutions were then concentrated to dryness and the products purified using the standard protocols for reverse-phase HPLC.

Synthesis of 3'-3' or 5'-5' Attached Oligonucleotides with Different Sequences

Synthesis of the Spacer Arm: 1-Dimethoxytrityl-3-laeyulinyl pronane-1,2,3-triol.

In this case, glycerol was also used as starting material for the preparation of the spacer arm. Any compound with the structure shown above can be used with good results.

Figure 10:
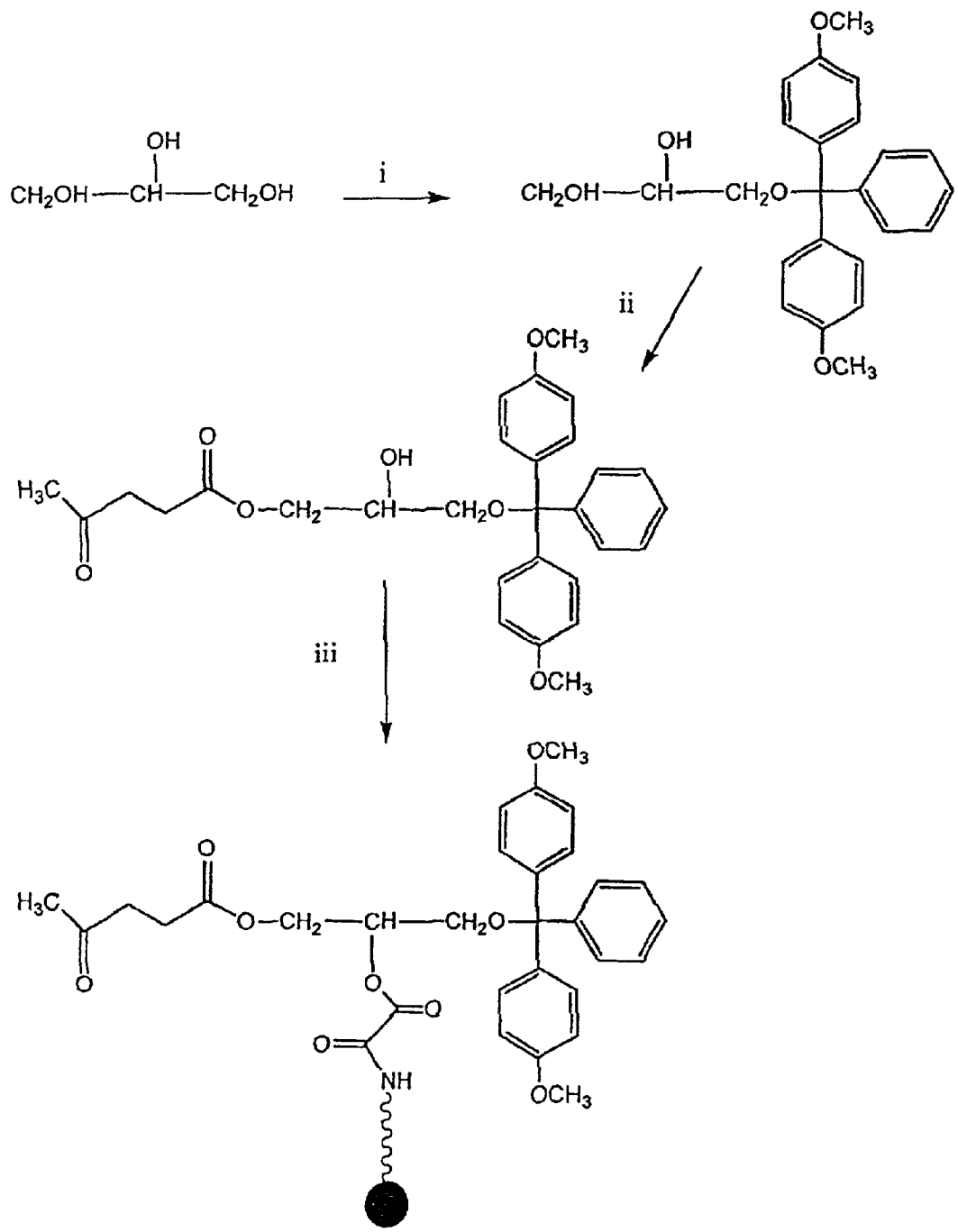
FIG. 10 shows the synthesis of the glycerol-spacer arm (AS) and attachment to LCAA-CPG using a linker.

The procedures to prepare the glycerol spacer arm (As)* is shown in FIG. 10. (AS*-Asymmetrical.) The synthesis of the glycerol-spacer arm (AS) was attached to the oxalyl linker, though the oxalyl can be replaced by succinyl or sarcosyl spacer arms. The reaction steps shown in FIG. 10 comprise reactions of i) dimethoxytrityl chloride in pyridine; ii) laevulinic anhydride and dimethylaminopyridine in dichloromethane; iii) oxalylchlroide and 1,2,4-triazol in acetonitrile, b) LCAA-CPG, c) DMAP, acetic anhydride, THF.

The first step of the synthesis consisted of the selective protection of one of the primary hydroxyl functions. The reaction was carried out in pyridine using an excess of glycerol.

The monoprotected product was dissolved in anhydrous dichloromethane. 4-Dimethylaminopyridine, triethylamine and laevulinic anhydride were added to the stirred solution with exclusion of moisture, and the reaction mixture was left at room temperature overnight. After the work-up, the desired compounds were purified by column chromatography on silica gel.

The 1,3-protected glycerol was dissolved in acetonitrile-pyridine (2:1) and then added to a previously prepared mixture of oxalyl chloride and 1,2,4-triazole in anhydrous acetonitrile. After 1 hour the solution was transferred to a gas-tight syringe containing the LCAA-CPG and the reaction is allowed to proceed for 30 minutes. The liquid was ejected from the syringe and the solid support washed successively with acetonitrile, anhydrous methanol (to cap residual oxalyl triazolide groups) and acetonitrile.

To acetylate underivatized amino groups from further reaction, the solid support was treated with an equivolume mixture of tetrahydrofuran (THF) solutions of DMAP and acetic anhydride for 30 minutes.

At the end, the support was washed with pyridine, acetonitrile, and diethyl ether, air dried and then dried in vacuo.

Synthesis of the 3'-3' and 5'-5' Attached Oligonucleotides with Different Sequences.

Figure 11A:
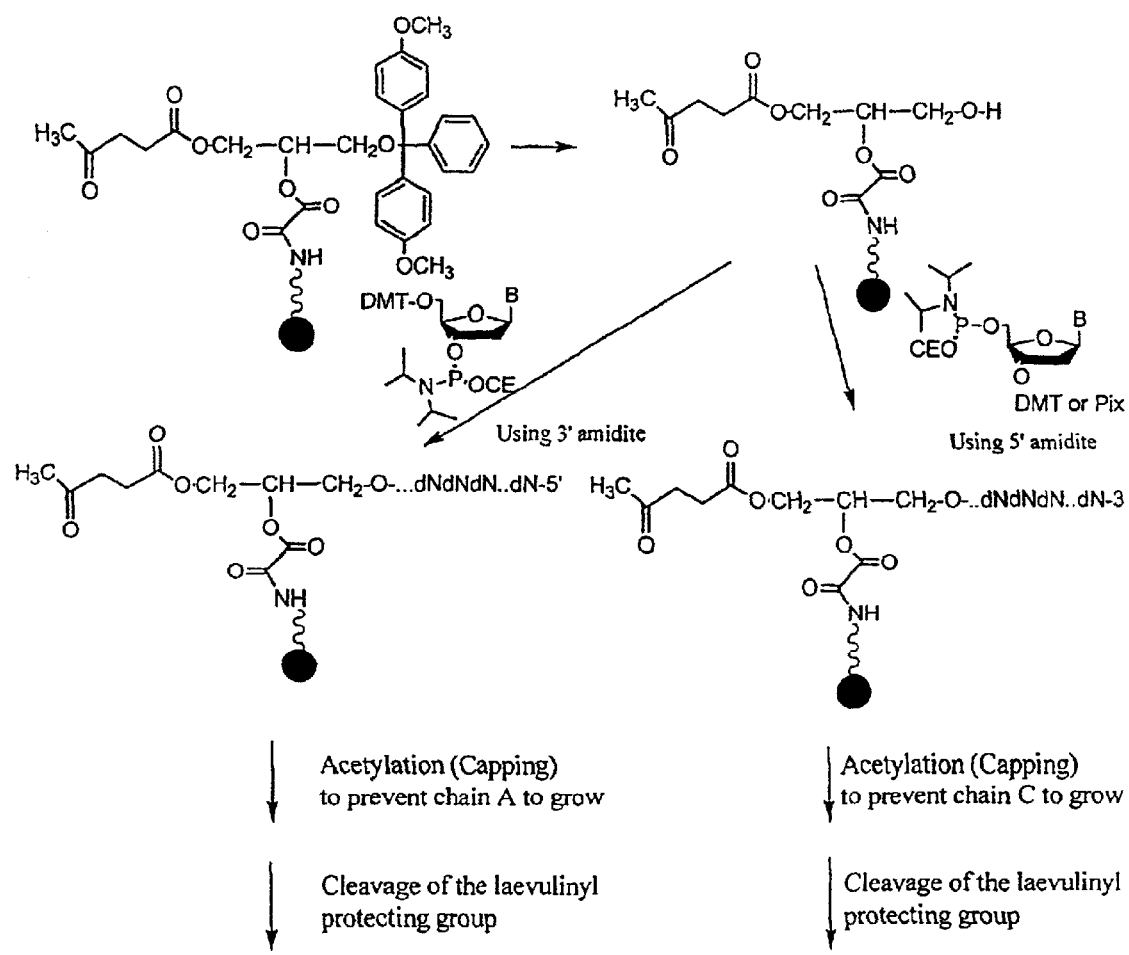
FIGS. 11A and B show the synthesis of 5'-5' and 3'-3' attached oligonucleotides with different sequences using the AS-glycerol spacer arm.
Figure 11B:
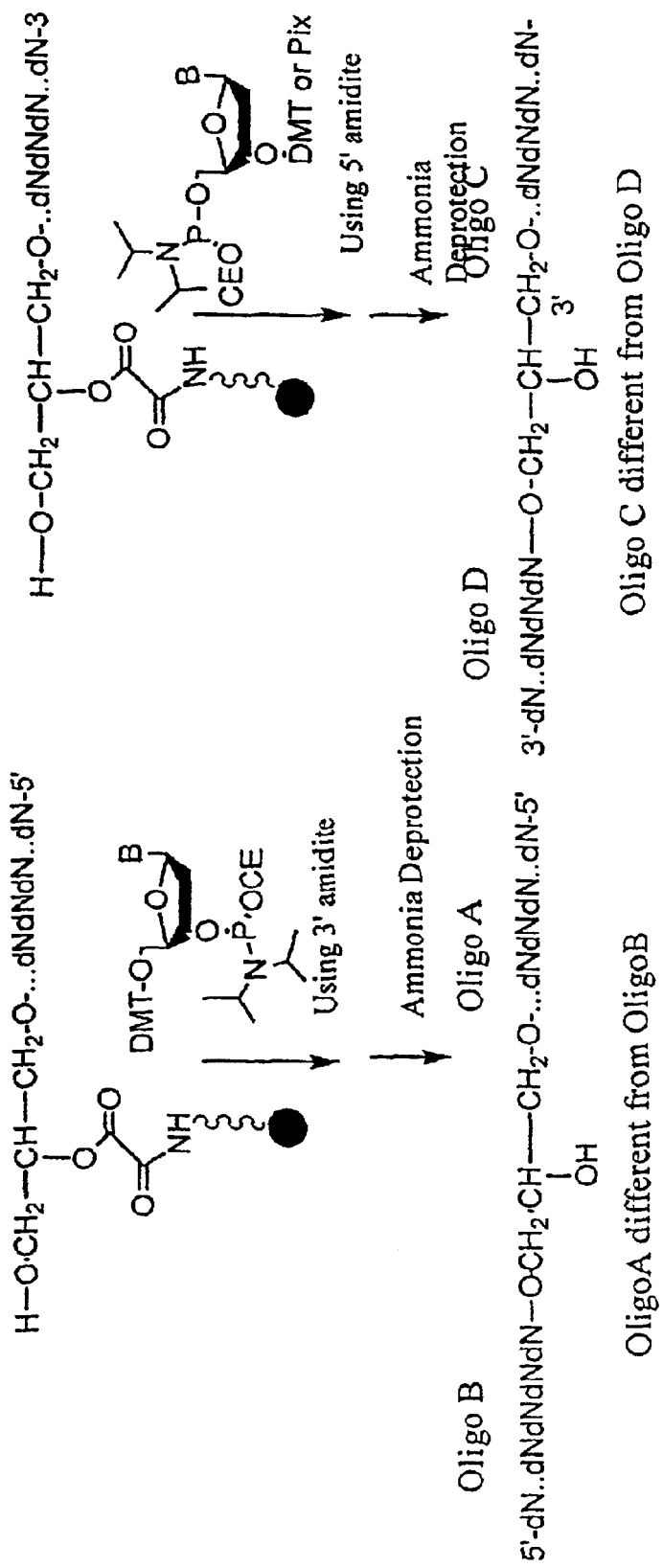

3'-3' and 5'-5' attached oligonucleotides with different sequences can be synthesized on an automatic DNA synthesizer using the glycerol spacer arm (As)-LCAA-CPG and standard or reversed 2-cyanoethyl phosphoramidite chemistry (FIGS. 11A and B).

At the beginning of the synthesis, the dimethoxytrityl-protecting group from the spacer arm was removed, allowing chain extension is that direction to complete the desired sequence. Then, the dimethoxytrityl protecting group of the last monomer added was removed and the resultant hydroxyl group was capped by acetylation to prevent further chain extension from this part. In order to be able to chain extend from the other hydroxyl group of the glycerol-spacer arm (As), the laevulinyl group was cleaved with hydrazine hydrate in pyridine acetic acid. Chain extension to give the desired 3'-3' or 5'-5' attached oligonucleotides was continued with the same type of phosphoramidites used for assembling the first chain. In this case, the dimethoxytrityl group of the last monomer added has to be left on the help reverse-phase HPLC-purification.

After the assembly of the sequence, the oligonucleotides were cleaved from the support by a treatment of 32% aqueous ammonia at 55° C. for 16 hours. Ammonia solutions were then concentrated to dryness and the products purified using the standard protocols for reverse-phase HPLC.

Hairpin sequences have been made starting from the middle of the loop as described above. However, an asymmetric phosphoramidite containing a Fmoc group instead of the laevulinyl group described above was employed. Further, the asymmetric linker employed was a glycerol derivative having the following general structure:

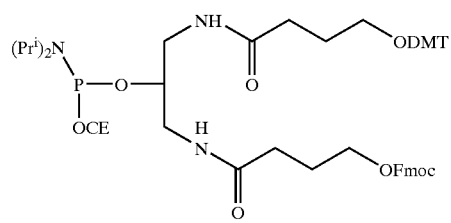

Using this strategy the following sequences were prepared. Sequence AR-22 is a control sequence without modified 8-aminopurines. Sequence AR22A-RNA is a sequence that contains two modified 8-aminoadenines, and the Hoogsteen strand is formed with 2'-O-methyl-RNA derivatives. Triplexes containing RNA molecules may form more stable triple helices. Also, RNA strands are easily degraded by nucleases. The AR22AA-RNA sequences have been designed to study the effect of the RNA in triple helix, and the use of 2-O-methyl-RNA derivatives is to avoid degradation of oligonucleotides by nucleases. Finally, a third strand was prepared to study the effect of the presence of 5-methyl-cytosine in the hairpin (AR22AmeC). This modified base has been described to stabilize triple helix when this base is in the Hoogsteen position. All sequences carry two extra thymidine residues at the 3'-end to have a flexible loop at the central position of the hairpin. The following structures represent the above-described sequences AR-22, AR22A-RNA and AR22AmeC:

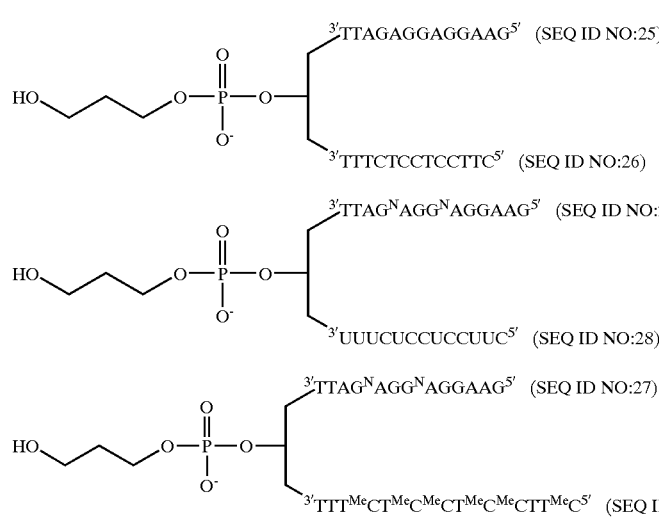

AR-22
3′TTAGAGGAGGAAG5′ (SEQ ID NO:25)
3′TTTCTCCTCCTTC5′ (SEQ ID NO:26)

AR22A-RNA
3′TTAG$^N$AGG$^N$AGGAAG5′ (SEQ ID NO:27)
3′UUUCUCCUCCUUC5′ (SEQ ID NO:28)

AR22AmeC
3′TTAG$^N$AGG$^N$AGGAAG5′ (SEQ ID NO:27)
3′TTT$^{Me}$CT$^{Me}$C$^{Me}$CT$^{Me}$C$^{Me}$CTT$^{Me}$C5′ (SEQ ID NO:29)

Binding Properties

Thermal stability of these hairpins was measured alone and with the target sequence. Triplex formed by the control hairpin AR-22 and target sequence WC-11mer was examined at pH 6.0. It was found a decrease of 7° C. on the Tm of the triplex compared with the triplex formed by R-22 and WC-11mer. The difference on the loops may be responsible of the decrease melting temperature.

Melting experiments with the RNA-DNA hairpin (AR22A-RNA) were performed with two different targets, S11WC and S11RNA. This last target was prepared in order to study the effect of the introduction of a RNA sequence as a target in the triplex binding stabilization.

WC-11mer: 5′TCTCCTCCTTC3′ (SEQIDNO:15)
S11RNA 5′UCUCCUCCUUC3′ (SEQ ID NO:30)

TABLE 10

Melting temperatures(° C.) of triplex at pH 6.0, 0.1 M sodium phosphate and citric acid, 1 M NaCl

| Hairpin | Target S11WC | target S11RNA | No target |
|---|---|---|---|
| B22 | 45 | 38 | 25 |
| R22A | 56 | 55. | 43 |
| B22A | 51 | 52 | 38 |
| B22G | 59 | 60 | 44 |
| AR22A-RNA | 66 | 71 | 58 |

Thermal denaturation studies of AR22A-RNA demonstrates that this hairpin hybridizes (Tm 66° C.) better than the corresponding R22A (Tm 56° C.). This tendency is also observed when the target is a RNA (Tm 71° C.) or DNA (Tm 66° C.), that means that RNA strand stabilizes WC base pairing. Moreover, Hoogsteen binding is also favoured as the melting point of AR22A-RNA alone is 15° C. greater than the corresponding R22A. Finally, hairpins carrying 8-aminopurines and 2-O-methyl-RNA formed more stable triplex with RNA targets, so they are better probes for capturing RNA.

Finally, melting experiments of the triplexes carrying 5-methyl-2′-deoxycytidine were performed with two different targets, WC-11mer and S11MeC. This last target was prepared in order to study the effect of the introduction of 5-methyl-C in the target site.

WC-11mer: 5′TCTCCTCCTTC3′ (SEQ ID NO:15)
S11MeC: 5′T$^{Me}$CT$^{Me}$C$^{Me}$C$^{TM}$C$^{Me}$CTTC3′ (SEQ ID NO:24)

TABLE 11

Melting temperatures in ° C. of triplex buffer 0.1 M sodium phosphate and citric acid, 1 M NaCl

| | Target S11WC pH6 | Target S11MeC pH6 | Target S11WC pH7 |
|---|---|---|---|
| B22 | 45 | 55 | 20 |
| B22A | 51 | 62 | 34 |
| AR22AMeC | 51 | 63 | 32 |
| B22G | 59 | 66 | 40 |

Melting temperatures of triplexes formed with asymmetric hairpins (i.e. AR22 +S11WC) are lower compared with hairpins with nucleotide or hexaethylene loop (i.e.B22A). Without being limited by theory, this is probably due to the asymmetric hairpin structure. The asymmetric hairpin with MeC, AR22AmeC, has the same Tm as B22A, so it may be concluded that the introduction of 5-methyl-C enhances triplex stability. Nevertheless, this effect is moderate.

Modified Nucleosides.

The present invention further comprises compositions and methods for the preparation of nucleosides with one or more linkers. For example, pyrimidine nucleosides with linker arms at $N^4$ of 2′-deoxycytidine using the 1,2-bis (aminoethoxy)ethane linker arm are disclosed herein, but any compound with structure shown below can be successfully used.

Structures for Preparing Pyrimidine Nucleosides with Linker Arms

1. $H_2N-(CH_2)n-NH_2$

2. $H_2N\diagdown\diagup O\diagdown\diagup O\diagdown NH_2$

3. $H_3C\diagdown NH\diagdown\diagup O\diagdown\diagup O\diagdown NH\diagup CH_3$ The compounds 1 or 2 can be purchased from commercially available sources. The spacer 3 is synthesized by the reaction of 1,2-bis(2-chloroethoxy)ethane with a 40% water solution of methylamine in a pressure vessel at 160° C. for 7 days.

Basic Approaches for Attaching Alkyl Linkers to $N^4$.

The three basic approaches for attaching alkyl linkers to $N^4$ have been:

1. Introductions of a leaving group such as triazolyl or nitrophenyl at $O_4$ of the 2'-deoxyuridine or deoxythymidine followed by a reaction with a diaminoalkane. See references 28–30.
2. Bisulphate catalyzed transamination of 2'-deoxycytidene with a diaminoalkane. See reference 31.
3. Displacement of sulphur from 4-thiopyrmidines with a diaminoalkane. See reference 32.

Figure 12:
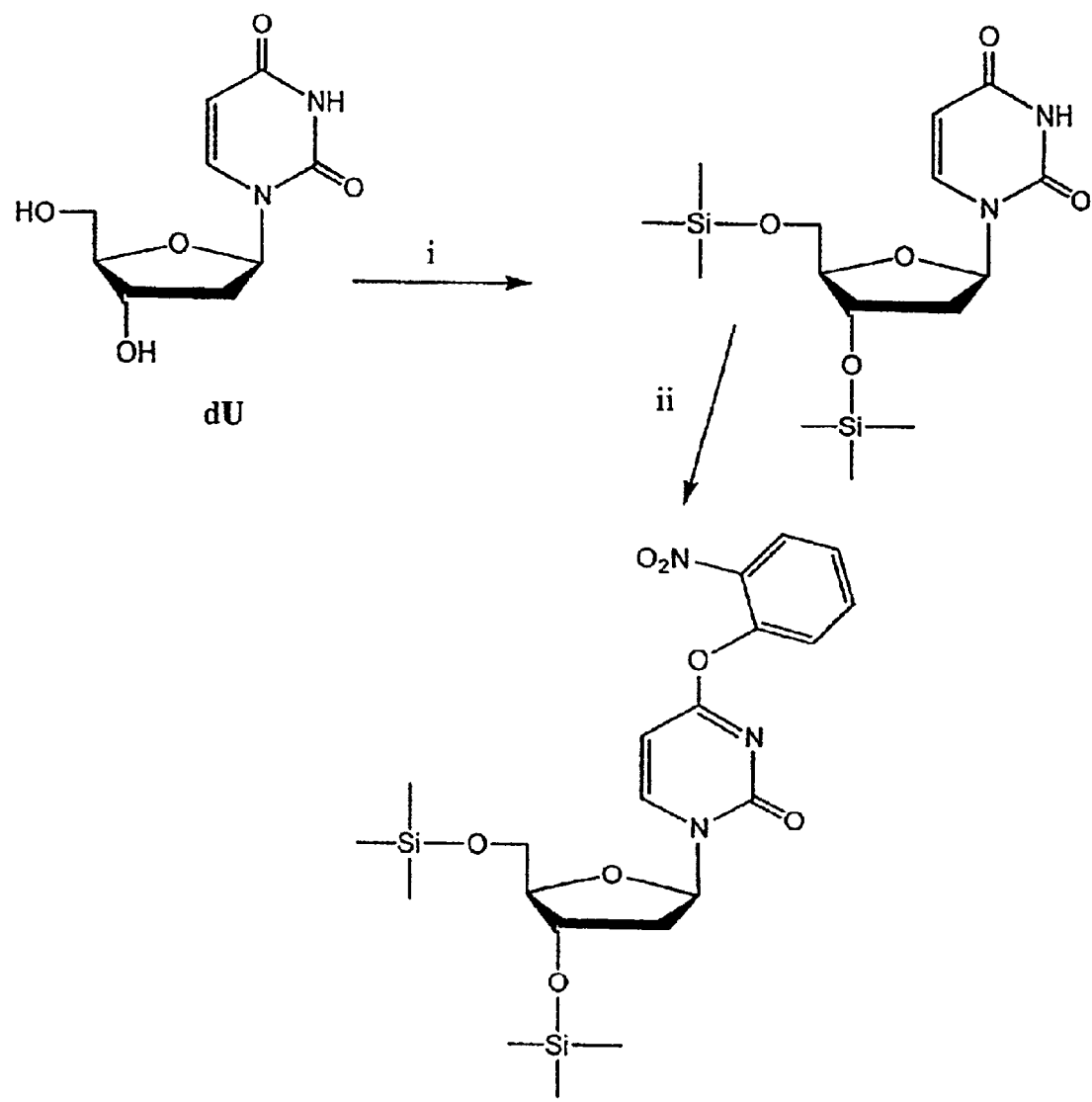
FIG. 12 shows the synthesis of the 2-nitrophenyl intermediate.

In the synthesis methods, the first approach was to synthesize the intermediates needed (see FIG. 12). The first intermediate synthesized was 3', 5'-O-bis(trimethylsilyl)-2'-deoxy-$O^4$-(2-nitrophenyl)uridine. Following the steps of FIG. 12, the first reaction is i), 1,1,1,3,3,3,-hexamethyldisilazane in DMF; ii) a) 0 triethylamine, 2-mesitylenesulphonyl chloride and 4-dimethylaminopyridine in dichloromethane, b) 1,4-diazabicyclo(2.2.2) octane and 2-nitrophenol in dichloromethane. It is contemplated by the present invention that other methods may be used to obtain the intermediates.

Attachment of Protected Fluorescein to the Spacer Arm.

Figure 13:
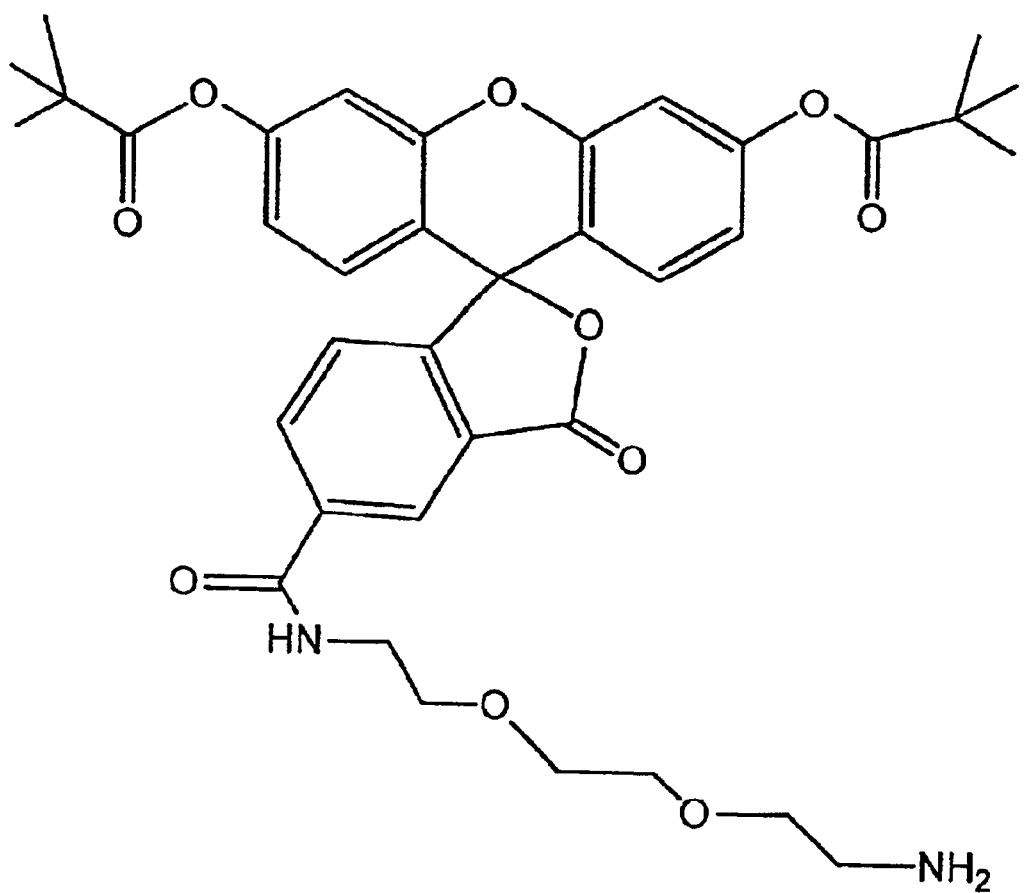
FIG. 13 illustrates a protected fluorescein attached to the 1,2-bis(aminoethoxy)ethane linker arm.

A preferred method of the present invention is the use of protected fluorescein isothiocyanate (supplied by Molecular Probes) in order to avoid modifications of the fluorophore during the oligonucleotide synthesis. The compound is designed to produce, on deprotection and isolation of the derived oligonucleotide, the same fluorescein isothiocyanate. See reference 26. The reactions of fluorescein isothiocyanate with primary amines are well described in the literature. The structure of the protected fluorescein attached to the spacer arm is shown in FIG. 13.

Synthesis of the 2'-Deoxy-5'-O-dimethoxytrityl-$N^4$-[8-amino-$N^8$-(3',6'-dipivaloylfluoresceinyl)-3,6-dioxaoctyl]cytidine-3'-O-(2-cyanoethyl-N,N-diisopropyl phosphoramidite).

Figure 14A:
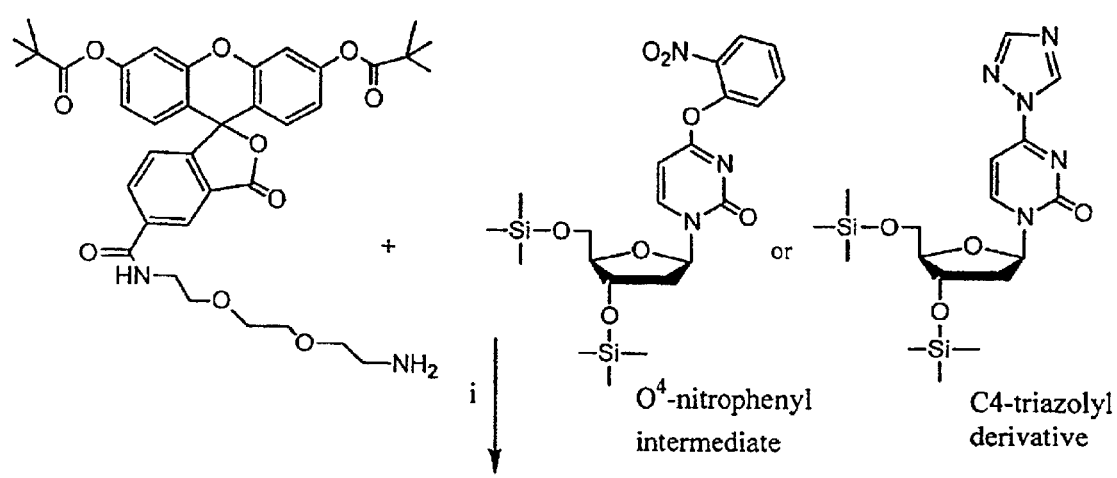
FIGS. 14A and B diagram the synthesis of the $N^4$-spacer arm-fluorescein labelled-2'-deoxycytidine phosphoramridite.
Figure 14B:
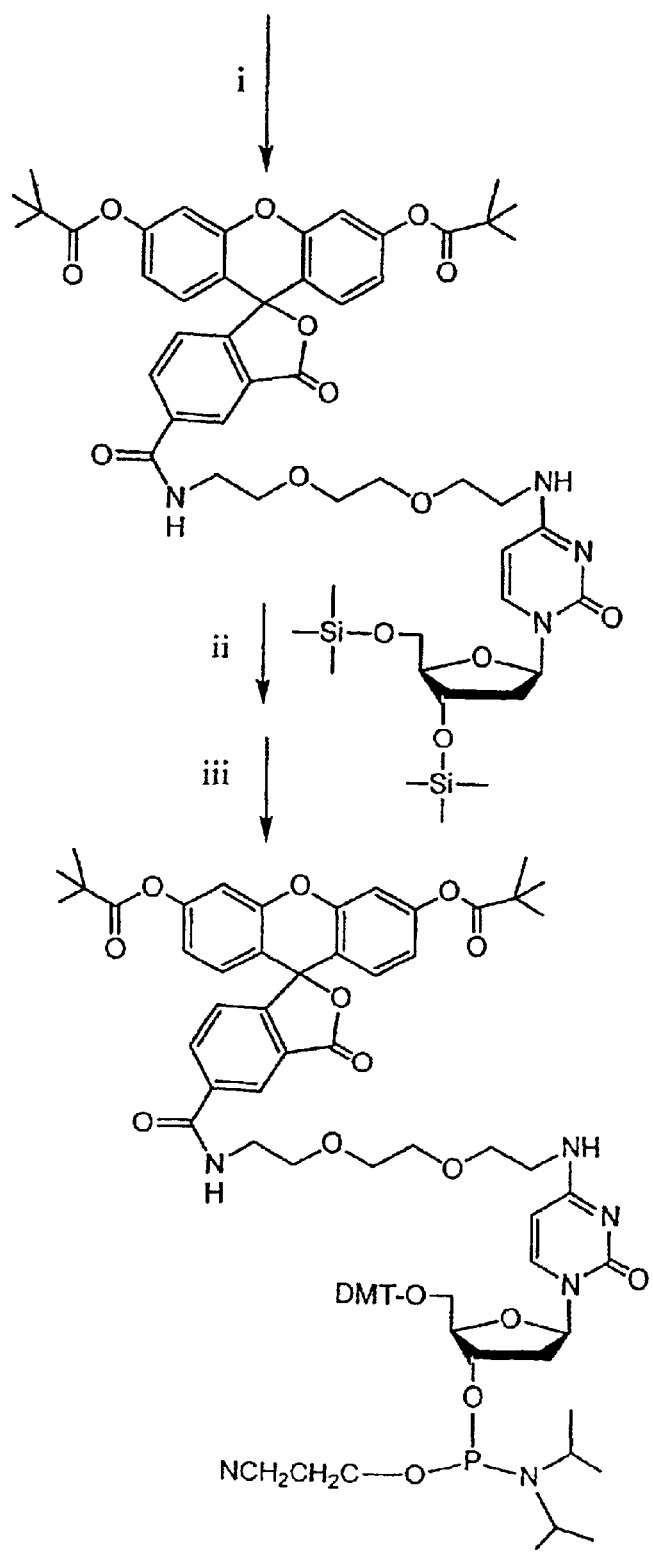

The attachment of the spacer arm bearing the protected fluorescein to the intermediate nucleotide and the synthesis of the final phosphoramidite are shown in the FIGS. 14A & B. The synthesis of the $N^4$-spacer arm-fluorescein labelled-2'-deoxycytidine phosphoramidite included the reactions of i) ethyldiisopropylaminer, dimethylformamide, overnight at room temperature; ii) dimethoxytrityl chloride in pyridine; iii) 2-cynoethoxy-N,N-diisopropylaminochloro phosphine and diisopropylethylamine in dichloromethane. The displacement reaction on the 4 position proceeded rather slowly, generally overnight, but with very good yields. The next steps were the established protocols for the protection of the 5'-hydroxyl function followed by the phosphitylation reaction with chloro-(2-cyanoethoxy)diisopropylaminophosphine.

Attachment of 5-bromouracil (Cleavage Agent) to the Spacer Arm.

Figure 15:
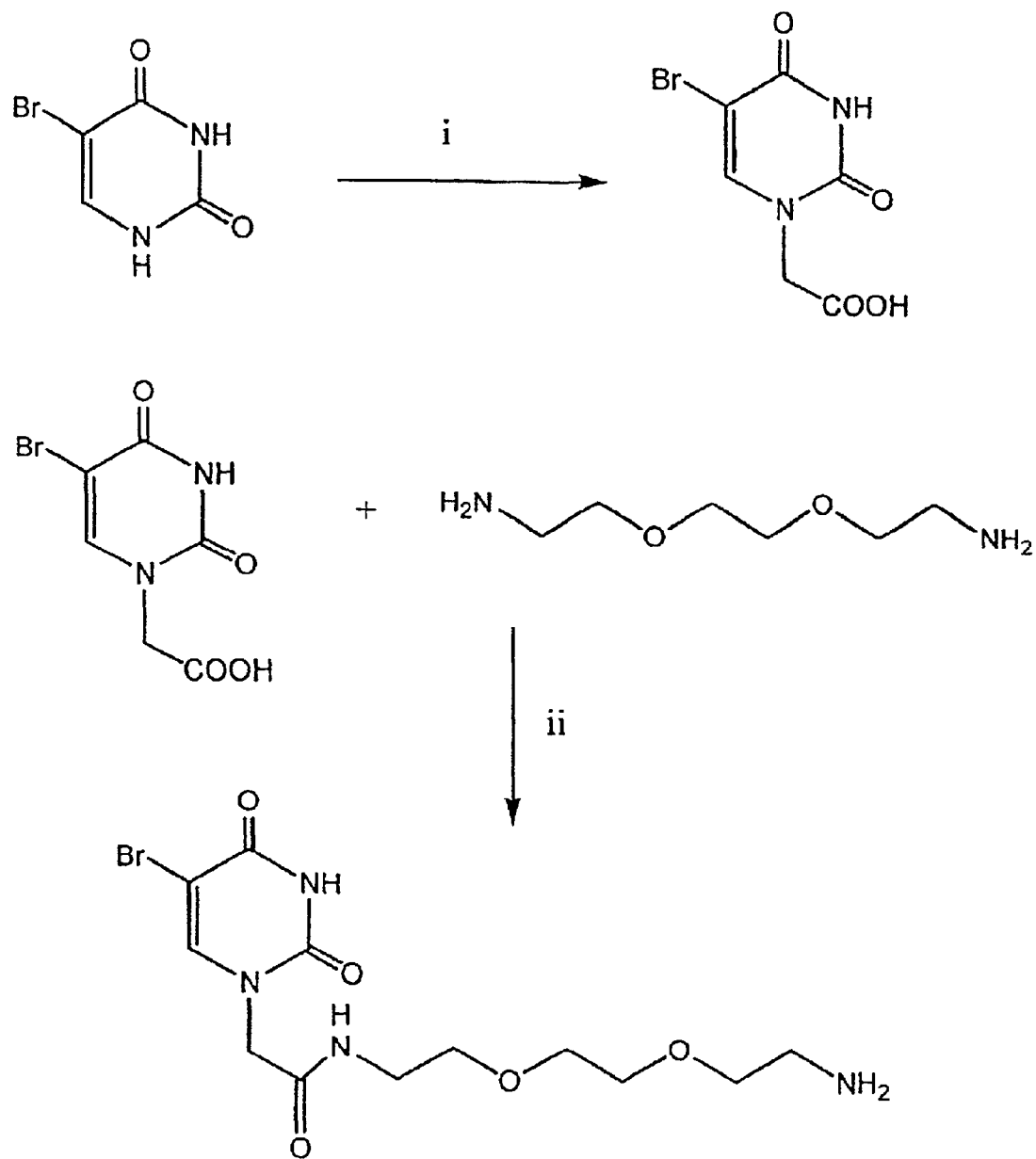
FIG. 15 shows a method for attachment of the 5-bromouracil to the 1,2-bis(aminoethoxy)ethane linker arm.

The attachment of 5-bromouracil to the spacer arm is a two step procedure (see FIG. 15). The attachment of the 5-bromouracil to the 1,2-bis(aminoethoxy)ethane linker arm comprised the reactions of i) bromoacetic acid, KOH, and water; and ii) 3,4-dihydro-3-hydroxy-4-oxo-1,2,3-benzotriazine (HOOBt), N,N'-diisopropylcarbodiimide (DIPC), and N-etilmorfoline (NEM) in DMF.

The first reaction was done to produce 1-carboxymethyl-5-bromouracil. Due to the structural similarity of 5-bromouracil with thymine, a procedure similar to the one that has been developed to prepare the 1-carboxymethyl-thymine was used. See reference 33. The second step was the attachment of the 1-carboxymethyl-5-bromouracil to the 1,2-bis(aminoethoxy)ethane linker arm.

Synthesis of the 2'Deoxy-5'-O-dimethoxytrityl-$N^4$-{8-amino-$N^8$-[[(5-bromo)uracil-1-yl]acetyl]-3,6-dioxaoctyl}cytidine-3'-O-(2-cyanoethy1-N,N-diisopropyl phosphoramidite).

Figure 16A:
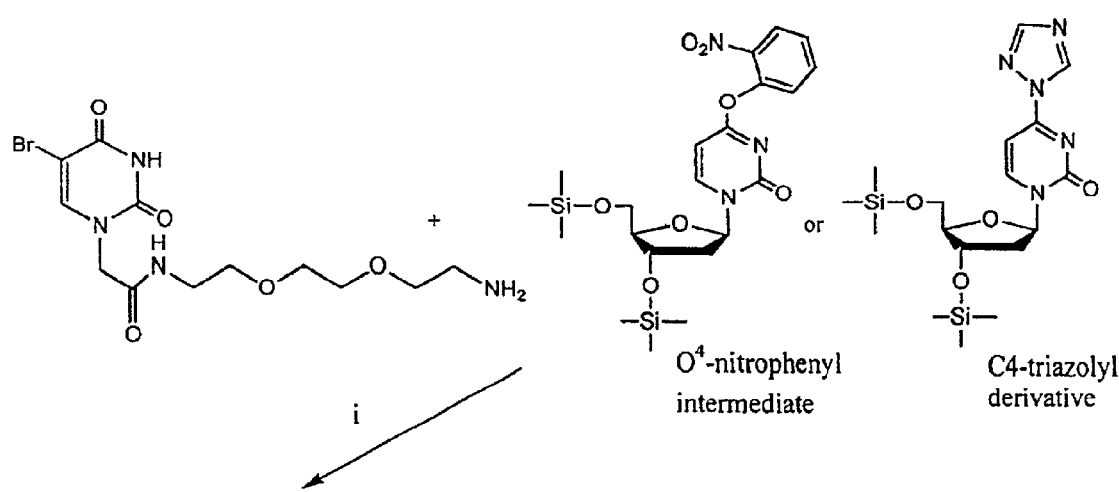
FIGS. 16A and B details the synthesis of the $N^4$-spacer arm-5-bromouracil-2'deoxycytidine phosphoramidite.
Figure 16B:
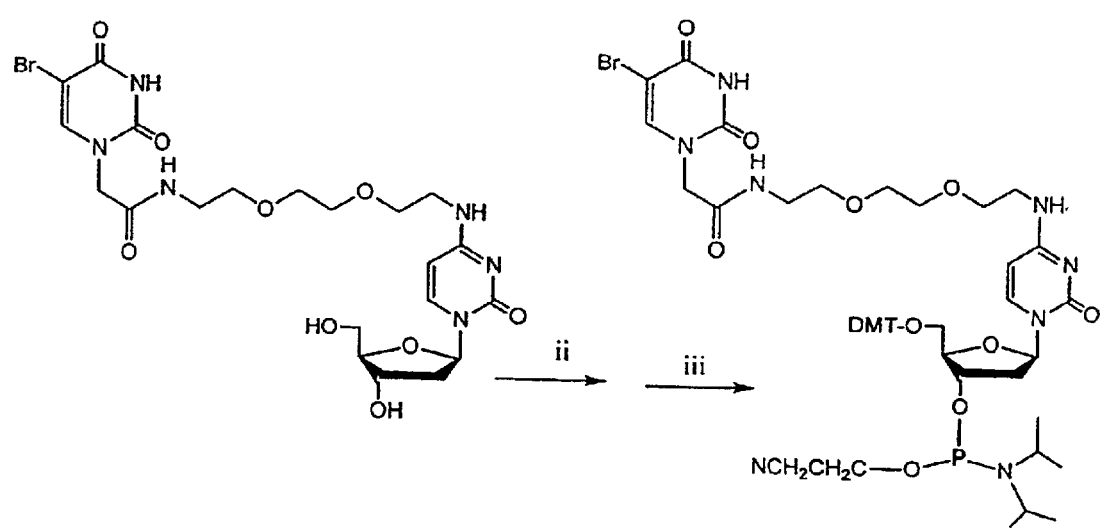

The attachment of the spacer arm bearing the 5-bromouracil to the intermediate nucleotide and the synthesis of the final phosphoramidite were carried out in the same way as for the fluorescein analogue (FIG. 16A & B). Synthesis of the $N^4$-spacer arm-5-bromouracil-2'-deoxycytidine phosphoramidite included the reactions of i) ethyldiisopropylamine, dimethylformamamide, overnight at room temperature; ii) dimethoxytrityl chloride in pyridine, iii) 2-cyanoethoxy-N,N-diisopropylaminochloro phosphine and diisopropylethylamine in dichloromethane.

The displacement reaction on the 4 position proceeded rather slowly (overnight) but with very good yields. The next steps were the established protocols for the protection of the 5'-hydroxyl function, followed by the phosphitylation reaction the chloro-(2-cyanoethoxy)diisopropylaminophosphine.

The present invention also comprises compositions and methods of synthesis and use of modified nucleosides. Particularly, the synthesis of reversed phosphoramidites of 5-methyl-2'-deoxycytidine, 8-amino-2'deoxyadenosine, 8-amino-2'-deoxyguanosine and 8-amino-2'-deoxyhyphoxanthine (8-amino-2'-deoxyinosine). These compounds can be used for the incorporation of triplex stabilizing nucleotides for assembling oligonucleotides in the 5' to 3' sense. The use of a pixyl moiety as a protecting group for the 3' hydroxyl improved the yield of the product. Synthesis of the 8-amino-2'-deoxy-N6, N8-bis(dimethylamino-methyliden)-3'-O-(9-phenylxanthen-9-yl)adenosine 5'-O-(2cyanoethyl-N,N-diisoproplyphosphoramidite).

Figure 17A:
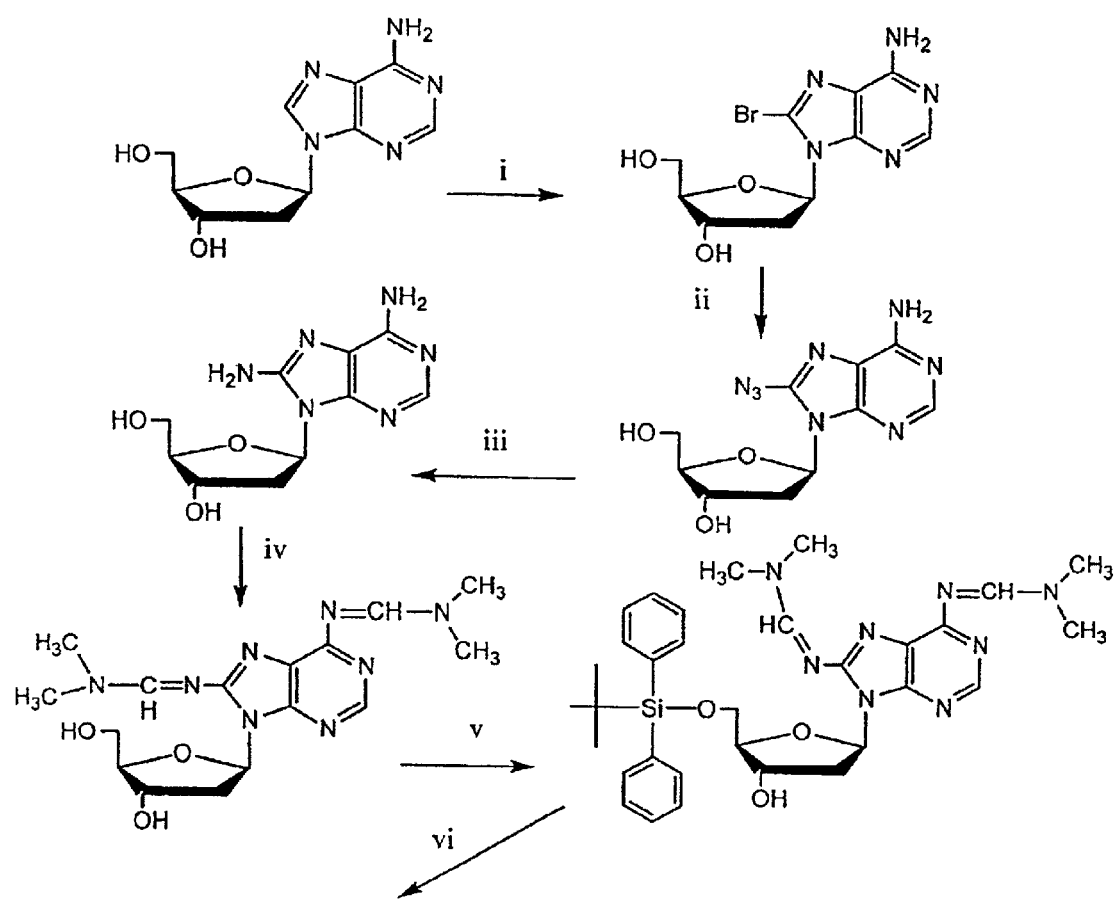
FIGS. 17A, B and C show the synthesis of the 8-amino-2'-deoxyadenosine monomer.
Figure 17B:
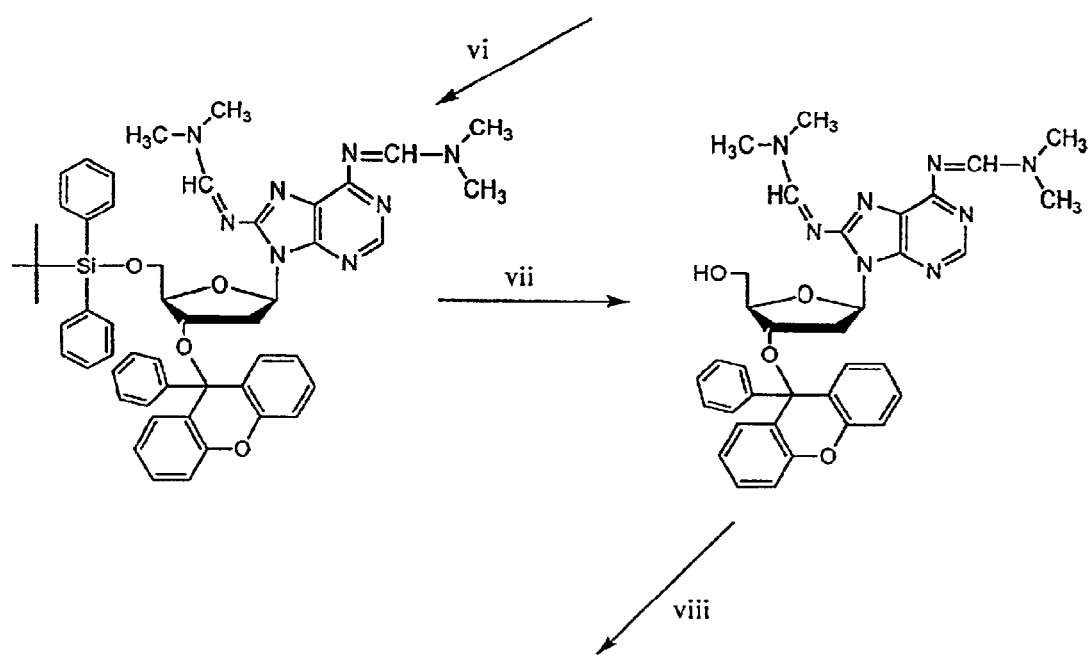
Figure 17C:
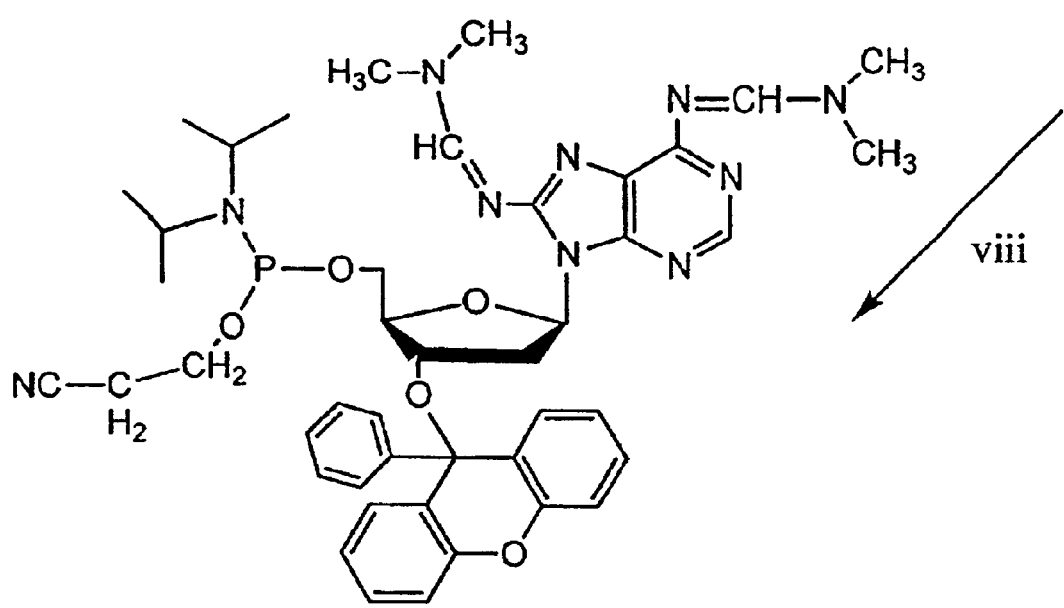

The synthesis of the 8-amino-2'-deoxyadenosine reversed monomer is illustrated in FIGS. 17A, B & C. Synthesis of the 8-amino-2'-deoxyadenosine reversed monomer, comprised the following: i) Bromine solution in 1M sodium acetate (pH 5.4), ii) sodium azide in DMF, 75° C., overnight, iii) Pd/C, $H_2$ in water-ethanol (6:4), iv) N, N-dimethylformamide dimethyl acetal in DMF, v) tert-butyldiphenylchlorosilane and imidazole in DMF, vi) 9-phenylxanthen-9-yl (Pixyl) chloride in pyridine, vii) tetrabutylammonium flouride (TBAF) in THF, viii) 2-cyanoethoxy-N,N-diisopropylaminochloro phosphine and diisopropylethylamine in dichloromethane. The 8-amino-2'-deoxy-$N^6$,$N^8$-bis-(dimethyl-aminomethyliden)adenosine was prepared as previously described. See references 4,33 and 36. In order to introduce the acid labile 9-phenylxanthen-9-yl (Pixyl) group on the 3'-hydroxy moiety it was necessary first to selectively protect the 5'-hydroxy function. See reference 37. The bulky lipophilic tert-butyldiphenylsilyl group carried out this protection. Overnight reaction of the free 3'-hydroxyl group with pixyl chloride pyridine produced the 3'-pixyl protected nucleoside. This protection can be alternatively done by using dimethoxytrityl chloride, which produced poorer yields. Removal of the tert-butyldiphenylsilyl protecting group with tetrabutylammonium fluoride (TBAF) allowed the isolation of the 3'-pixyl compound. Finally, 5'-hydroxy group phosphilylation with chloro-(2-cyanoethoxy)diisopropylaminophosphine afforded the desired monomer.

Synthesis of the 8-amino-2'-deoxy-N², N⁸-bis(dimethyl-aminomethyliden)-3'-O-(9-phenlxanthen-9-yl)guanosine-5'-O-(2-cyanoethyl-N,N-diisopropylphosphoramidite).

Figure 18A:
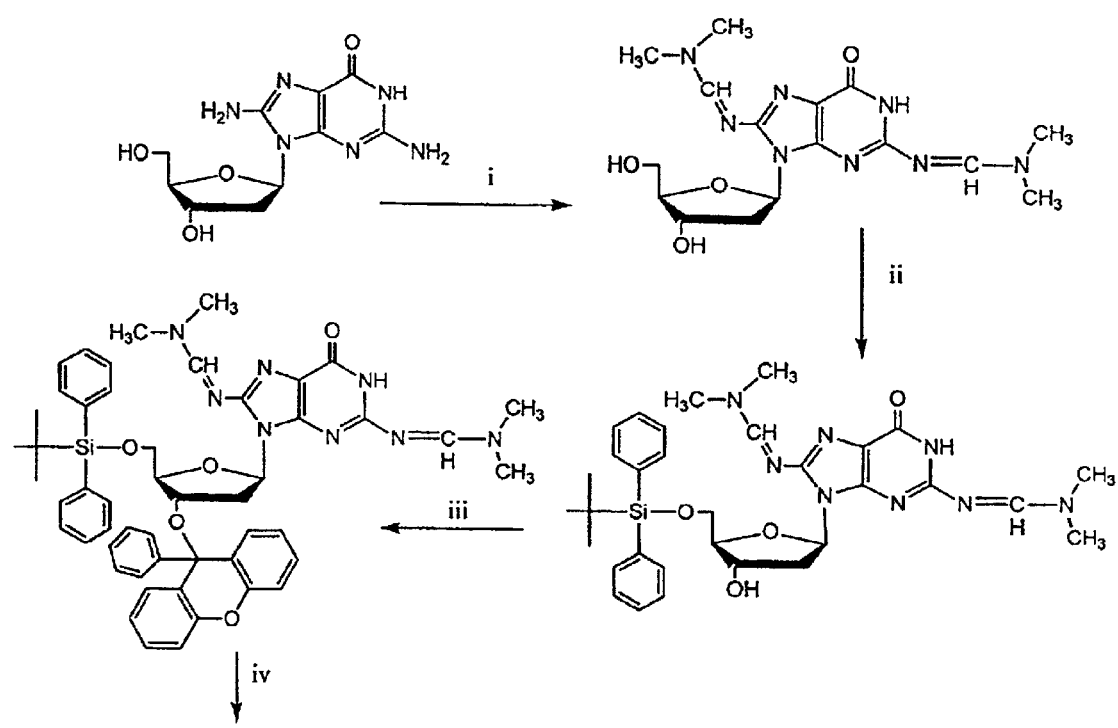
FIGS. 18A and B diagrams the synthesis of the 8-amino-2'-deoxyguanosine reversed monomer.
Figure 18B:
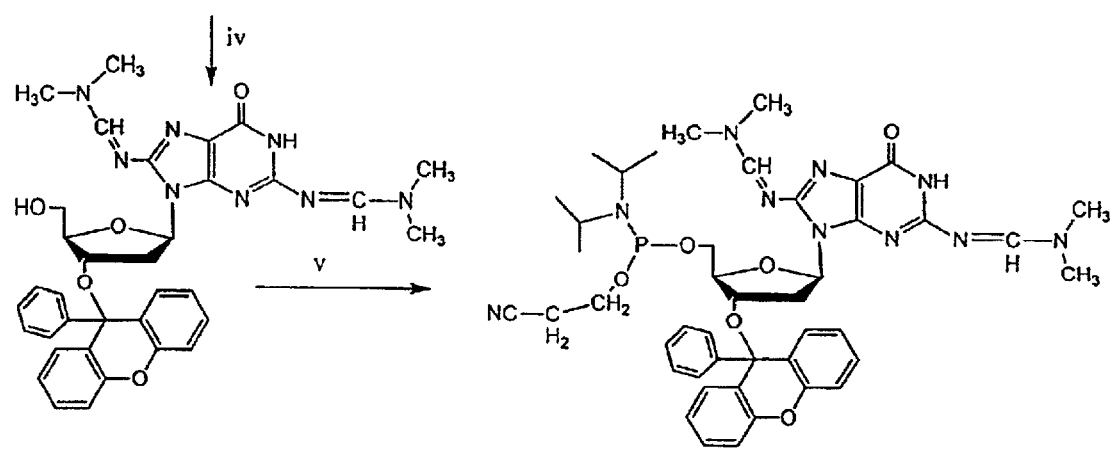

The synthesis of the 8-amino-2'-deoxyguanosine reversed monomer is illustrated in FIGS. 18A & B. Synthesis of the 8-amino-2'-deoxyguanosine reversed monomer comprised the following steps: i) N,N-dimethylformamide dimethyl acetal in DMF, ii) tert-butyldiphenylchlorosilane and imidazole in DMF, iii) 9-phenylxanthen-9-yl (Pixyl) chloride in pyridine, iv) tetrabutylammonium fluoride (TBAF) in THF, v) 2-cyanoethoxy-N,N-diisopropylaminochloro phosphine and diisopropylethylamine in dichloromethane. The 8-amino-2'-deoxy-N⁶,N⁸-bis(dimethyl-aminomethyliden) guanosine was prepared as previously described. See reference 12. In order to introduce the acid labile 9-phenylxanthen-9-yl (Pixyl) group on the 3'-hydroxy moiety it is necessary first to selectively protect the 5'-hydroxy function. The bulky lipophilic tert-butyldiphenylsilyl group carried out this protection. Overnight reaction of the free 3'-hydroxyl group with pixyl chloride pyridine produced the 3'-pixyl protected nucleoside. This protection can be done alternatively by using dimethoxytrityl chloride, which produces poorer yields. Removal of the tert-butyldiphenylsilyl protecting group with tetrabutylammonium fluoride (TBAF) allowed the isolation of the 3'-pixyl compound. Finally, the 5'-hydroxy group phosphitylation with chloro-(2-cyanoethoxy)diisopropylaminophosphine afforded the desired monomer.

Synthesis of the 8-amino-2'-deoxy-N⁸-isobutyryl-3'-O-(9-phenylxanthen-9-yl)inosine-5'-O-(2-cyanoethyl-N,N-diisopropyl-phosphorainidite).

Figure 19A:
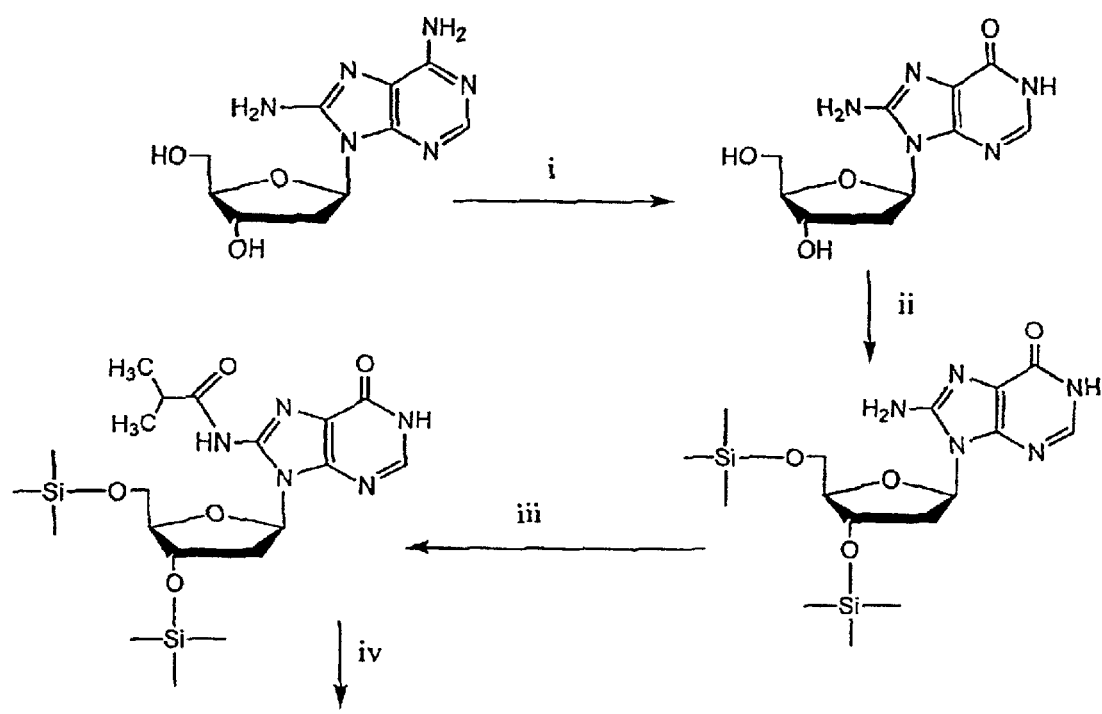
FIGS. 19A and B illustrates the synthesis of the 8-amino-2'-deoxyinosine reversed monomer.
Figure 19B:
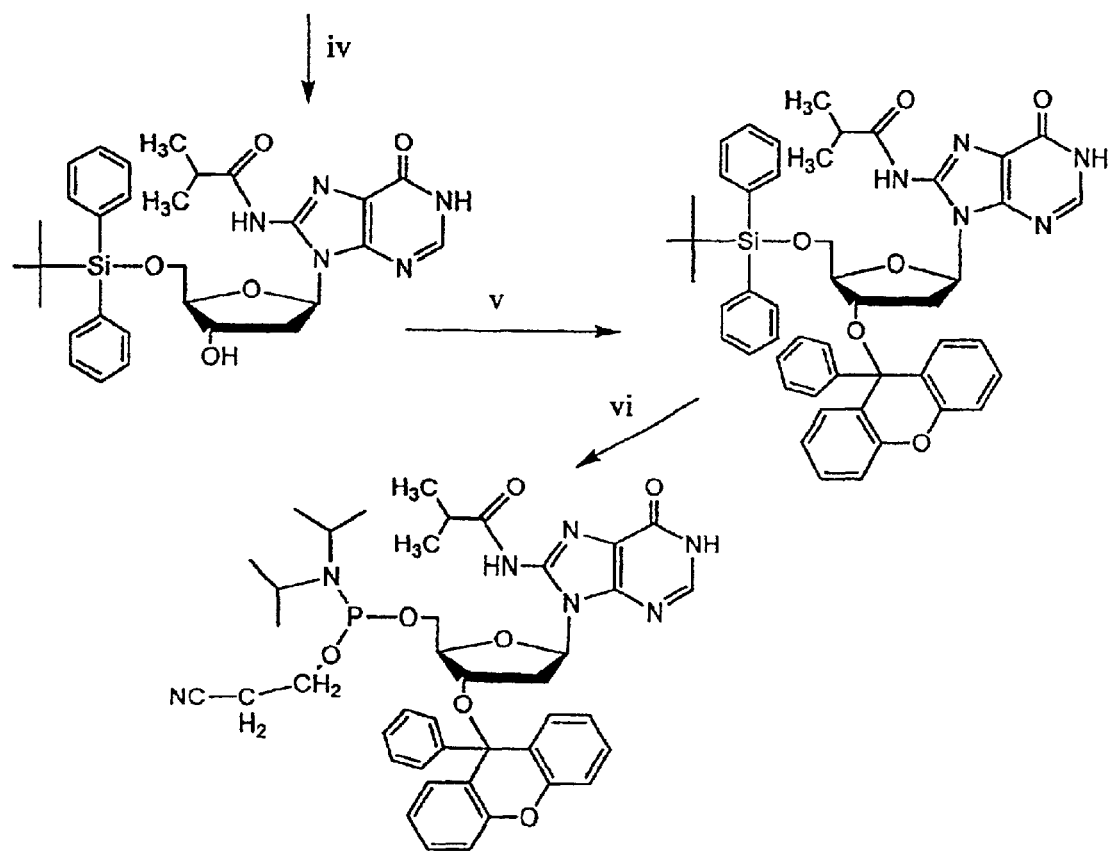

In summary, the synthesis comprised reactions comprising the following steps, i) Adenosine deaminase in a mixture of dimethylsuphoxide and 0.1M aqueous sodium phosphate (1:3), ii) 1,1,1,3,3,3-Hexamethyldisilazane in DMF, iii) Isobutyryl chloride in pyridine, iv) a) Dioxane/Methanol/25% aqueous ammonia (1:1:2), b) tert-butyldiphenylchlorosilane and imidazole in DMF, v) 9-phenylxanthen-9-yl (Pixyl) chloride in pyridine, vi) a) tetrabutylammonium fluoride (TBAF) in THF, b) 2-cyanoethoxy-N,N-diisopropylaminochloro phosphine and diisopropylethylamine in dichloromethane. The 8-amino-2'-deoxyinosine was obtained from the treatment of 8-amino-2'deoxyadenosine with adenosine deaminase at 37° C. for 72 hours. The exocyclic amino protection was then introduced via transient protection procedure to give the N⁸-isobutyryl compound. In order to introduce the acid labile 9-phenylxanthen-9-yl (Pixyl) group on the 3'-hydroxy moiety it was necessary first to selectively protect the 5'-hydroxy function. The bulky lipophilic tert-butyldiphenylsilyl group carried out the protection. Overnight reaction of the free 3'-hydroxyl group with pixyl chloride pyridine produced the 3'-pixyl protected nucleoside. This protection can be done alternatively by using dimethoxytrityl chloride, which produces poorer yields. Removal of the tert-butyldiphenylsilyl protecting group with tetrabutylammonium fluoride (TBAF) allowed the isolation of the 3'-pixyl compound. Finally, 5'-hydroxy group phosphitylation with chloro-(2-cyanothoxy) diisopropylaminophosphine afforded the desired monomer. The synthesis of the 8-amino-2'deoxyinosine reversed monomer is illustrated in FIGS. 19A & B.

Synthesis of 2'-deoxy-N⁴-isobutyryl-5-methyl 3'-O-(9-phenylxanthen-9-yl)cytidine-5'-O-(2-cyanoethyl-N,N-diisopropylphosphoramidite).

Figure 20A:
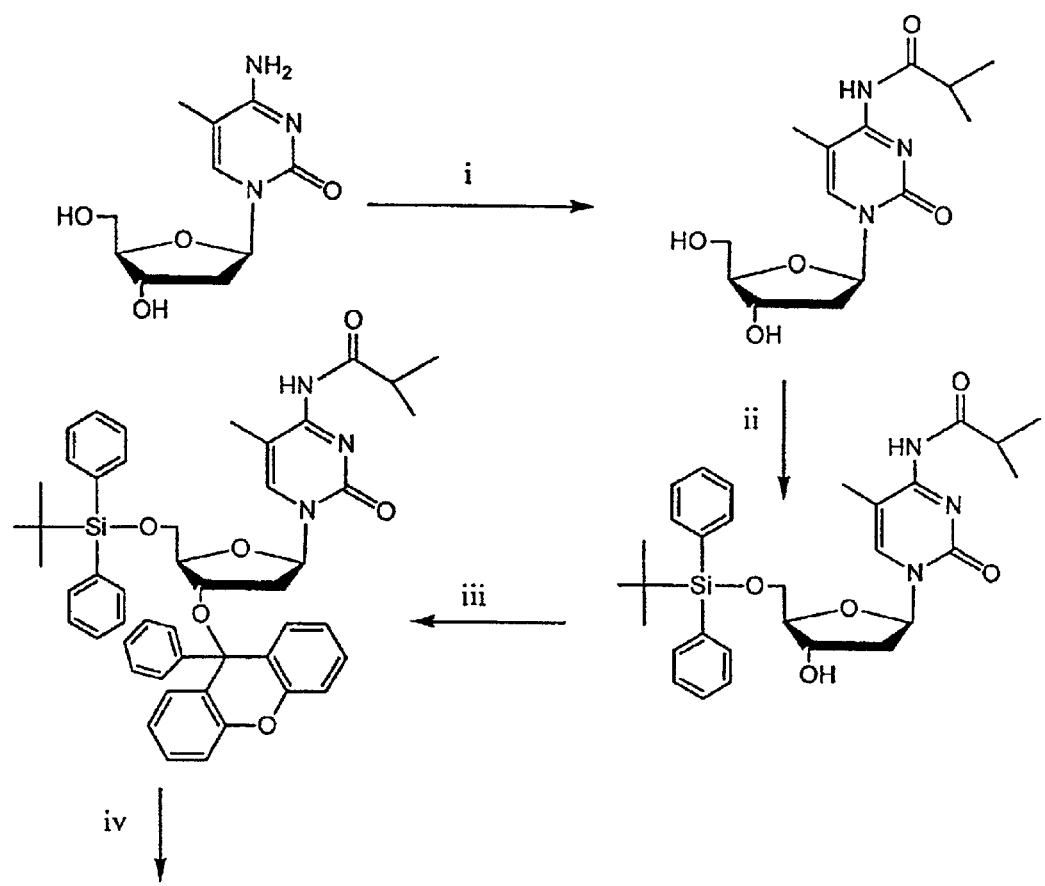
FIGS. 20A and B show the synthesis of the 5-methyl-2'-deoxycytidine reversed monomer.
Figure 20B:
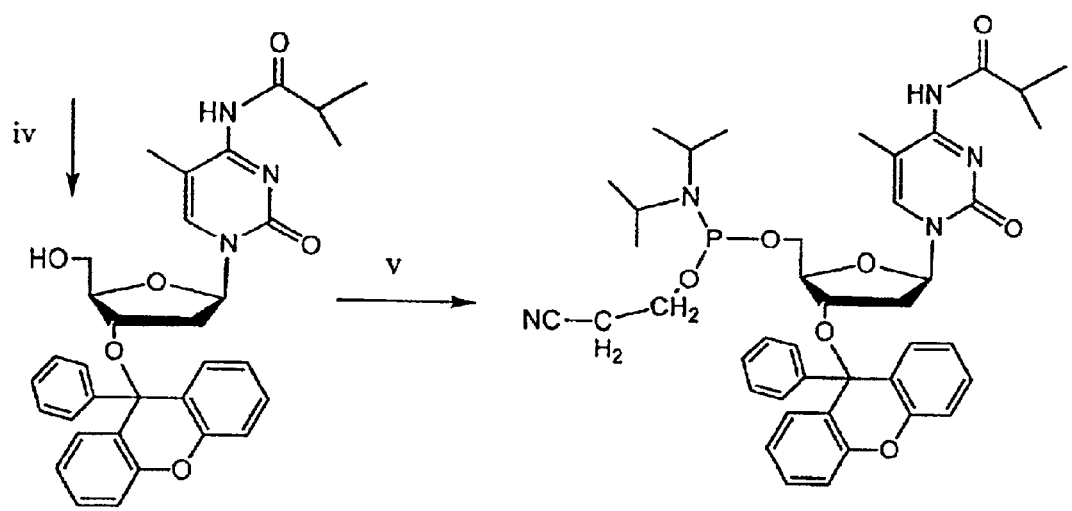

The reactions comprise the following steps i) a) 1,1,1,3,3,3-Hexamethyldisilazane in DMF, b) Isobutyryl chloride in pyridine, c) Dioxane/Methanol/25% aqueous ammonia (1:1:2), ii) tert-butyldiphenylchlorosilane and imidazole in DMF, iii) 9-phenylxanthen-9-yl (Pixyl) chloride in pyridine, iv) tetrabutylammonium fluoride (TBAF) in THF, v) 2-cyanoethoxy-N,N-diisopropylaminochloro phosphine and diisopropylethylamine in dichloromethane. The procedures to synthesize 5-methyl-2'deoxycytidine are well established. See references 28–30 and 38. The exocyclic amino protection was then introduced via transient protection procedure to give the N⁴-isobutyryl compound. In order to introduce the acid labile 9-phenylxanthen-9-yl (Pixyl) group on the 3'-hydroxy moiety it was necessary to selectively protect the 5'-hydroxy function. The bulky lipophilic tert-butyldiphenylsilyl group carried out the protection. Overnight reaction of the free 3'-hydroxyl group with pixyl chloride pyridine produced the 3'-pixyl protected nucleoside. This protection can be done alternatively by using dimethoxytrityl chloride, which produces poorer yields. Removal of the tert-butyldiphenylsilyl protecting group with tetrabutylammonium fluoride (TBAF) allowed the isolation of the 3'-pixyl compound. Finally, 5'-hydroxy group phosphitylation with chloro-(2-cyanothoxy)diisopropylaminophosphine afforded the desired monomer. The synthesis of the 5-methyl-2'-deoxycytidine reversed monomer is illustrated in FIGS. 20A & B.

In another aspect of the present invention, hairpin sequences carrying the peptide sequence c-myc have been prepared. The preparation of oligonucleotide-peptide conjugates presents an interesting challenge because the standard protection schemes used in peptide and oligonucleotide synthesis are not compatible. For example, amide-type protecting groups are used for the protection of nucleobases. These protecting groups are removed by ammonia under conditions that could hydrolize nucleopeptide bonds or provoke unwanted side reactions such as racemization or aspartamide formation. In contrast, all standard protection schemes in solid-phase peptide synthesis utilize acid treatments, which could provoke partial depurination of DNA. In order to overcome these problems, a stepwise solid-phase approach is employed. For example, the oligonucleotide-peptide conjugate is prepared on a single support using special protecting groups and modified protocols that minimize unwanted side reactions.

Preparation of an oligonucleotide containing 8-amino derivatives attached to a short peptide c-myc can be accomplished by employing using two different synthetic routes. In one aspect of the present invention, the stepwise solid-phase synthesis is described. Alternatively, in another aspect of the present invention, the use of an asymmetric doubler for the preparation of conjugates is described.

Stepwise Solid-Phase Approach

Figure 25:
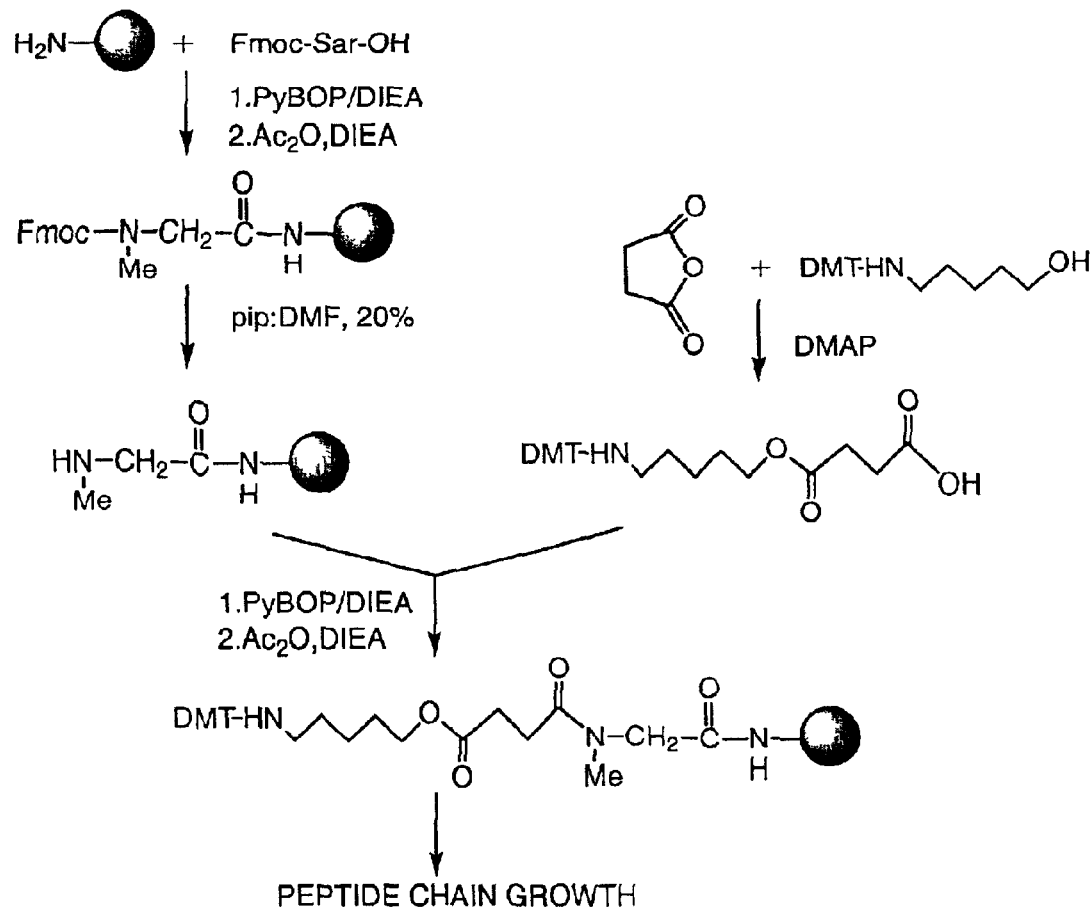
FIG. 25 illustrates solid support preparation.
Figure 26:
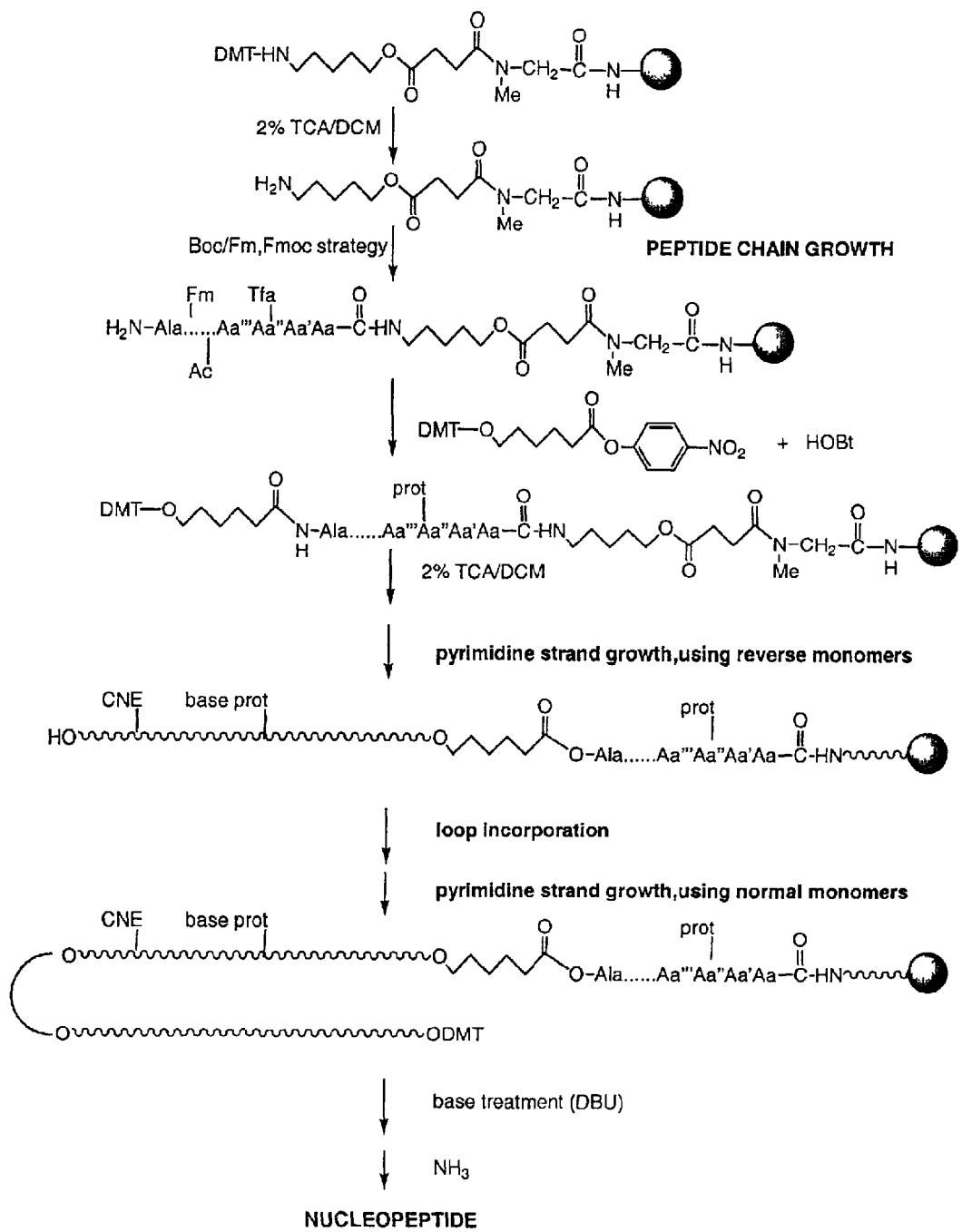
FIG. 26 illustrates a preparation of oligonucleotide peptide conjugates employing a stepwise solid-phase approach.

The route to the synthesis of the oligonucleotide-peptide conjugate is illustrated in FIGS. 25 and 26. Using a base-labile linker attached to a PEG-PS support, the peptide is first assembled. Boc-amino acids protected with the base labile Fmoc and Fm groups are used as coupling units. The repetitive acid treatments used for the removal the Boc group were performed without the presence of the oligonucleotide.

Another important feature of the synthesis of a conjugate is the choice of the solid support. Polystyrene supports are used in peptide synthesis, and CPG supports are incorporated for oligonucleotide synthesis. Coupling reactions on Teflon, PS and PEG-PS are less dependent on the activation method used during peptide synthesis than on CPG, but are less efficient in oligonucleotide synthesis. The low efficiency of these supports is compensated by increasing the coupling time and changing the solvent to dissolve the phosphoramidites. Any of these supports may be employed with the present invention.

The peptide sequence was synthesized via the solid phase on a 0.19 mmol scale using a homemade manual synthesizer and amino-PEG-PS (0.19 mmol/g) as the solid support. The handle, 6-DMT-aminohex-1-yl hemisuccinate, was anchored to the resin as described elsewhere. The loading of the support was measured by the absorbance of the DMT cation and was 0.1 mmol/g. The elongation of the peptide was carried out in DMF using a 5-fold excess of Boc-amino acid, 10-fold excess of DIEA, and 5-fold excess of PyBOP for 1 hour. In order to remove the Boc group, the support was treated with TFA-DCM (3:7) for 30 minutes and neutralized with DIEA-DCM (1:19).

After the addition of the last amino acid, the 6-hydroxypentanoate linker (5-fold excess in DMF for 1 hour) was added to connect the peptide fragment to the oligonucleotide by converting the last amino group of the peptide to a dimethoxytrityl-protected hydroxyl function. The oligonucleotide component is assembled using the standard phosphoramidites on a DNA-Synthesizer on a 1 $\mu$mol scale. The phosphoramidites were disolved in dry DCM, giving 0.1 M solutions (using reverse phosphoramidites for the pyrimidine chain growth and normal phosphoramidites and 8-amino derivatives for the purine chain elongation). The coupling time was increased to 5 minutes, capping and oxidation times were increased to 1 minute, and the detritylation step to 2 minutes. The last DMT protecting group was not removed. The supports were washed with ACN and dried. Following linear assembly, some of the protecting groups (Fmoc, Fm, CNE) are removed with DBU. The conjugate is liberated from the solid support by concentrated ammonia (with drops of dioxane) in an overnight treatment at 55° C., with concomitant removal of the nucleobase protecting groups.

After filtration of the solid support, the solution was evaporated to dryness, the residue was disolved in water, and the conjugate purified using standard two-step HPLC purification. In the first separation, truncated sequences were separated from the DMT-containing product, and in the second seperation, the conjugate was isolated after removal of the DMT group with 80% aqueous acetic acid for 30 minutes. Characterization was performed via mass spectrometry analysis after 6 N HCl hydrolysis.

Asymmetric Doubler Approach

Figure 27:
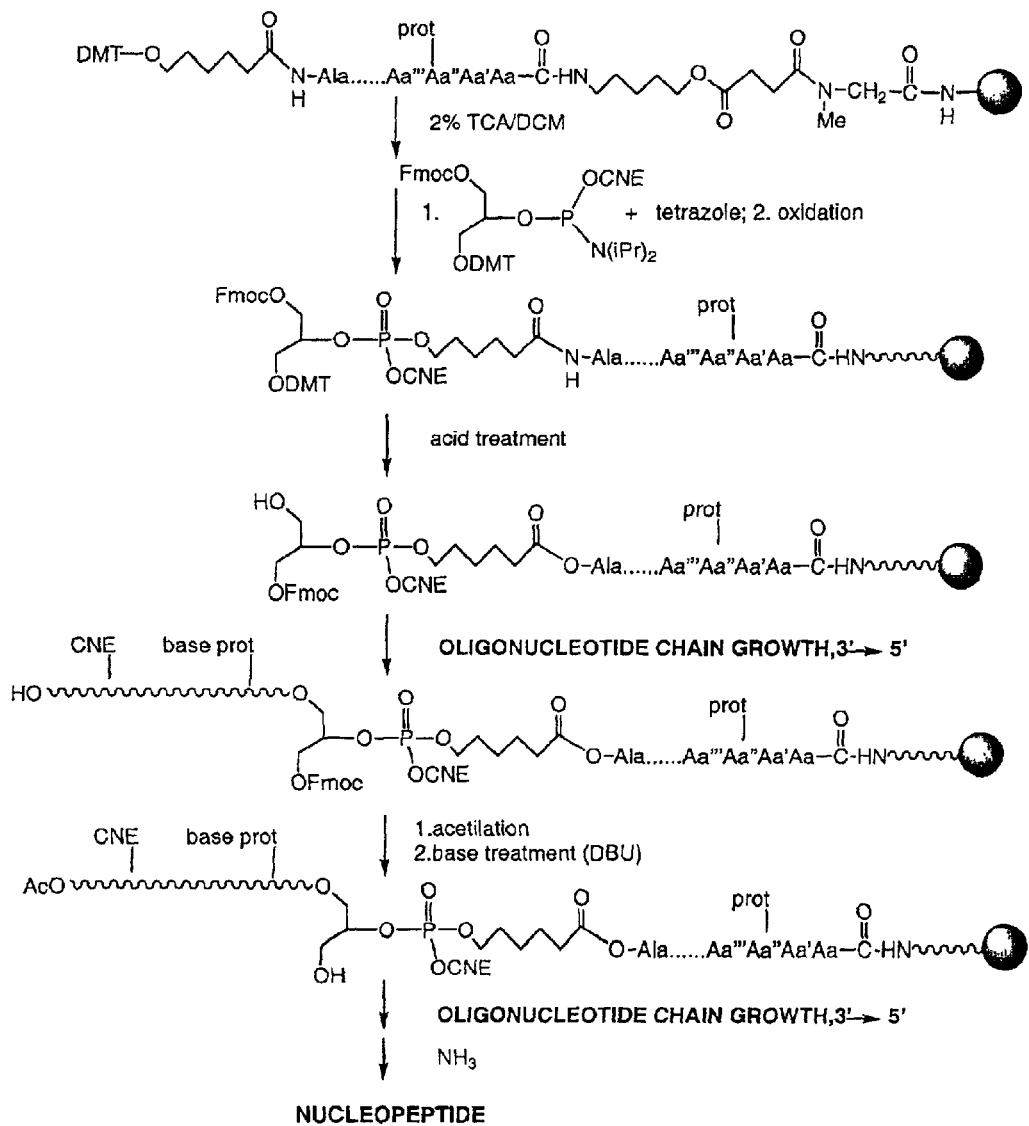
FIG. 27 illustrates a preparation of oligonucleotide peptide conjugates employing an assymetrical doubler approach.

Now, referring to FIG. 27, the peptidyl support was prepared as described above for the stepwise solid-phase approach. After the addition of the last amino acid, the 6-hydroxypentanoate linker (5-fold excess in DMF for 1 hour) was also added to connect the peptide fragment to the oligonucleotide by converting the last amino group of the peptide to a dimethoxytrityl-protected hydroxyl function.

Before the oligonucleotide assembly, an asymmetric doubler was incorporated to the peptidyl support. One arm has an Tfa-hydroxyl protection, while the second arm presents a DMT-alcohol protecting group. The synthesis proceeded deprotecting the DMT and elongating the purine strand using normal phosphoramidites. Just after that, an acetilation treatment took place before the base deprotection of the second arm. The pyrimidine chain was assembled with standard monomers.

The phosphoramidites were disolved in dry DCM, giving 0.1 M solutions. The coupling time was increased to 5 minutes, capping and oxidation times were increased to 1 minute, and the detritylation step to 2 minutes. The last DMT protecting group was not removed. The supports were washed with ACN and dried. Following linear assembly, some of the protecting groups (Fmoc, Fm, CNE) were removed with DBU. The conjugate was liberated from the solid support by concentrated ammonia (with drops of dioxane) in an overnight treatment at 55° C., with concomitant removal of the nucleobase protecting groups.

After filtration of the solid support, the solution was evaporated to dryness, the residue was disolved in water, and the conjugate purified using standard two-step HPLC purification. In the first seperation, truncated sequences were separated from the DMT-containing product, and in the second seperation the conjugate was isolated after removal of the DMT group with 80% aqueous acetic acid for 30 minutes.

In accordance with the present invention, the asymmetric approach avoids the use of reverse monomers. Reverse monomers are quite expensive, and the results are marginal. In contrast, the stepwise solid-phase approach of the present invention provides improved results and yields.

REFERENCES

1. Thuong, N. T., Hélène, C., *Angew.Chem. Int. Ed. Engl.*, 1993, 32, 666.
2. Soyfer, V. N., Potaman, V. N., *Triple helical Nucleic Acids*, 1996, Springer-Verlag, New York.
3. Malvy, C., et at., *Triple helix forming oligonucleotides* 1999, Kluwer Academic Pub. Dordrecht, the Netherlands.
4. Güimil García, R., et al., *Nucleic Acids Res.* 1999, 27, 1991.
5. Kawai, K., et al., *Tetrahedron Lett.* 1998, 3898, 5221.
6. Kumar, R. K., et al., *Biochem. Biophys. Res. Comm.*, 1994, 204, 788.
7. Shields, G. C., et al., *J. Am. Chem. Soc.*, 1997, 119, 7463.
8. Hattori, M., et al., *Biochemistry*, 1975, 14, 5033.
9. Hattori, M., et al., *Biopolymers*, 1976, 15, 523.
10. Güimil García, R., et al., *M. Bioorg. Med. Chem. Lett.* 1998, 8,3011.
11. Güimil García, R., Eritja, R., Orozco, M., mans. in prep.
12. Rao, T. S., et al.,*J. Heterocyclic Chem.*, 1994, 31, 935.
13. Ricger, R. A., et al., *Nucleosides Nucleotides*, 1999, 18, 89.
14. Bannwarth, W., *Chimia*, 1987, 41, 302.
15. Letsinger, R. L., et al., *J. Am. Chem. Soc.*, 1975 97, 3278.
16. Duran, M., et al., *Biochemistry*, 1992, 31, 9197.
17. Ortigao, J. F. R., et al., *Antisense Res. & Dev.*, 1992, 2, 129.
18. Sproat, B., et al., *J. Chem. Soc. Perkin Trans.*, 1994, 1, 419.
19. Alul, R. H., et al., *Nucl. Acids Res.*, 1991, 19, 1527.
20. Murasugi, A., Wallace, R. B., *DNA*, 1984, 3, 269.
21. Trainor, G. L., Jensen, M. A., *Nucleic Acids Res.*, 1988, 16, 11846.
22. Viscidi, R. P., et al,*J. Clin. Microbiol.*, 1986, 23, 311.
23. Foster, A. C., et al., *Nucleic Acids Res.*, 1985, 13,745.
24. Sanford, D. G., Krugh, T. R, *Nucleic Acids Res.*, 1985, 13, 5907.

25. Lebacq, P., et al., M., *J. Biochem. Biophys. Methods*, 1988, 255.
26. Ruth, J. L., *Oligonucleotides and Analogues. A practical approach*, 1991, Oxford, IRL Press.
27. Thuong, N. T., Asseline, U., *Oligonucleotides and Analogues. A practical approach.* 1991, Oxford.IRL Press.
28. Urdea, M. S., et al., *Nucleic Acids Res.*, 1988, 16, 4937.
29. Horn, T., Urdea, M. S., *Nucleic Acids Res.*, 1989, 17, 6959.
30. Sproat, B. S., et al., *Nucleic Acids Res.*, 1989, 17, 3373.
31. Telser, J., et al., *J. Am. Chem. Soc.*, 1989, 111, 6966.
32. Roget, A., et al., *Nucleic Acids Res.*, 1989, 17, 7643.
33. Kosynkina, L., et al., *Tetrahedron Lett.*, 1994, 35, 5173.
34. van de Sande, J. H., et al., *Science*, 1988, 241, 551.
35. Holmes, R. E., et al., *J. Am. Chem. Soc.*, 1965, 87, 1772.
36. Long, R. A., et al., *J. Org. Chem.*, 1967, 32, 2751.
37. Chattopadhyaya, J. B., Reese, C. B., *J. Chem. Soc., Chem. Commun.*, 1978, 639.
38. Nyilas, A., Chattopadhyaya, J., *Acda Chem. Scand*, 1986, B40, 826.
39. Horne, D. A., and Dervan, P. B., *J. Am Chem Soc* (1990) 112:2435–2437.
40. Froehler, B. C., et al., *Biochemistry* (1992) 31:1603–1609).
41. Kandimalla, E. R. and Agrawal, S., *Biochemistry* (1996) 35:15332–15339
42. Rippe, K. and Jovin, T. M., *Methods in Enzymology* (1992) 211:199–220).
43. Suggs, S. V. et al, *Proc. Natl. Acad. Sci. USA* (1984) 78: 6613–6617).
44. Nichols, R. et al., *Nature* (1994) 369:492–493.
45. Loakes D. and Brown, D. M., *Nucleic Acids Res.* (1994), 22:4039–4043.
46. Loakes D. et al., *Nucleic Acids Res.* (1995) 23:2361–2366).
47. Martin et al, *Nucleic Acids Res.* (1985) 13: 8927–8938.
48. Ohtsuka, E. et al., *J. Biol. Chem.* (1985) 280: 2605–2608.
49. Takahashi, Y. et al., *Proc. Natl. Acad. Sci. USA* (1985) 82: 1931–1935.
50. Schulhof, J et al., *Nucleic Acids Res.* (1987), 15, 397–416).
51. Caruthers, M. H. et al., *Methods in Enzymology* (1987) 154:287–313).

This invention is illustrated by the included examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the included claims.

EXAMPLES

Example 1

Oligonucleotide Synthesis

Oligonucleotides were prepared on an automatic DNA synthesizer using standard and reversed 2-cyanoethyl phosphoramidites and the modified phosphoramidites of the 8-aminopurines prepared as described. See references 4, 5, 10–13. The phosphoramidite of the hexaethyleneglycol linker was also obtained from commercial sources. Complementary oligonucleotides containing natural bases were also prepared using commercially available chemicals and following standard protocols. After the assembly of the sequences, oligonucleotide-supports were treated with 32% aqueous ammonia at 55° C. for 16 hours. Ammonia solutions were concentrated to dryness and the products were purified by reverse-phase HPLC. Oligonucleotides were synthesized on 0.2 $\mu$mol scale and with the last DMT group at the 5' end (DMT on protocol) to help reverse-phase purification. All purified products presented a major peak which was collected and analyzed by snake venom phosphodiesterase and alkaline phosphatase digestion followed by HPLC analysis of the nucleosides (HPLC conditions B). Yield (OD units at 260 nm after HPLC purification, 0.2 $\mu$mol) were between 6–10 OD.

HPLC Conditions

HPLC solutions were as follows. Solvent A: 5% ACN in 100 mM triethylammonium acetate (pH 6.5) and solvent B: 70% ACN in 100 mM triethylammonium acetate pH 6.5. For analytical runs the following conditions were used. Column: Nucleosil 1210$C_{18}$, 250×4 mm, flow rate: 1 ml/min. Conditions A) a 40 min linear gradient from 0 to 75%B. Conditions B) a 20 min linear gradient from 0 to 20% B. For preparative runs the following conditions were used: Columns: PRP-1 (Hamilton), 250×10 mm. Flow rate: 3 ml/min. A 30 min linear gradient from 10–80% B (DMT on), or a 30 min linear gradient from 0–50% B (DMT off).

Melting Experiment

Melting experiments with triple helix were performed as follows: Solutions of equimolar amounts of the modified oligonucleotide (22-mer) and the target Watson-Crick pyrimidine strand (11-mer) were mixed in the appropriate buffer. The solutions were heated to 90° C., allowed to cool slowly to room temperature and then samples were kept in the refrigerator overnight. UV absorption spectra and melting experiments (absorbance vs. temperature) were recorded in 1 cm path-length cells using a spectrophotometer, which has a temperature controller with a programmed temperature increase of 0.5° C./min. Melts were run on duplex concentration of 4 $\mu$M at 260 nm.

Example 2

Synthesis of 8-amino-2'deoxyadenosine.

In a screw-cap tube 4.62 g of 8-azido-2'-deoxyadenosine (Long et al. *J. Org. Chem.* (1967) 32:2751–2756) were dissolved with 20 ml of 40% aqueous methylamine solution and 2 ml of dioxane. The solution was heated overnight at 55° C. Then the solution was cooled at room temperature and concentrated to dryness yielding an oil that was used in Example 3 without purification. Purity judged by HPLC (<95%).

Example 3

Synthesis of 8-amino-N,N-bis(dimethylaminomethyliden)-2'deoxyadenosine.

8-amino-2'deoxyadenosine produced in Example 2 above (approx. 17.5 mmol) was dissolved in 250 ml of N,N-dimethylformamide and treated with 12.1 ml of dimethyl acetal of the N,N-dimethylformamide. The solution was stirred overnight at room temperature and, then, evaporated to dryness. The resulting product was purified by silica gel chromatography yielding 5.4 g of the desired compound (82% yield).

Example 4
Synthesis of the phosphoramidite of 8-amino-N,N-bis (dimethylaminomethyliden)-2'-deoxyadenosine.

The 8-amino-N,N-bis(dimethylaminomethyliden)-2'deoxyadenosine produced in Example 3 above (2 g, 5.3 mmol) was dissolved into dry pyridine (20 ml), and dimethoxytrityl chloride (2.15 g, 6.4 mmol) was added to the solution. After 3 hrs of magnetic stirring at room temperature methanol (2 ml) was added and the solution was concentrated to dryness. The residue was dissolved in dichloromethane and the solution was washed with aqueous sodium bicarbonate solution and brine. The organic phase was dried over $Na_2SO_4$ and evaporated. Silica gel chromatography yielded 2.2 g (3.2 mmol, 61% yield) of the desired 5'-dimethoxytrityl-8-amino-N,N-bis(dimethylaminomethyliden)-2'-deoxyadenosine.

The product described above (0.94 g, 1.38 mmol) was dissolved in anhydrous tetrahydrofuran (35 ml) containing 0.69 ml (4.14 mmol) of diisopropylethylamine. The solution was cooled in an ice-bath and 2.04 mmol of N,N-diisopropylamino-2-cyanoethoxy chlorophosphine was added. After 1 hr of magnetic stirring at room temperature, the solution was concentrated to dryness. The residue was dissolved in dichloromethane and the organic solution was washed with 1M sodium bicarbonate and brine, dried ($Na_2SO_4$) and concentrated to dryness. The residue was purified by silica gel chromatography yielding 0.9 g of the desired compound (1.02 mmol, 74%).

Example 5
Preparation of 8-amino-2'-deoxyinosine.

In a round-bottom flask 2 g (7.5 mmol) of 8-amino-2'-deoxyadenosine (Long R. A. et al ref. 36 and Example 2) were dissolved with 150 ml of 0.1 M aqueous sodium phosphate buffer (pH 7.5). Adenosine deaminase (150 mg of crude powder from calf intestinal mucosa) was added. The resulting solution was stirred at 37° C. for 72 hrs. A precipitate was formed that was the desired product. Completion of the reaction was checked by TLC (ethanol/dichloromethane 1:4). It was observed the disappearance of the starting material to produce a more polar compound. The precipitate was filtered yielding 1.8 g (6.7 mmol, 89% yield) of 8-amino-2'-deoxyinosine.

Example 6
Preparation of 8-amino-2'-deoxy-5'-O-dimethoxytrityl-$N^8$-isobutyryl-inosine-3'-O-(2-cyanoethyl)-N,N-diisopropyl-phosphoramidite.

The nucleoside from Example 2 (1.5 g, 5.6 mmol) was dried by evaporating dry pyridine (10 ml) twice. The resulting residue was dissolved in 20 ml of dry pyridine and treated with phenoxyacetic anhydride (24 mmol, 7.2 g). After 2 hrs of stirring at room temperature water (3 ml) was added to destroy the excess of anhydride and the mixture was concentrated to dryness. A mixture of triethylamine-pyridine-water 20/20/60 was added to deprotect the 3' and 5'-hydroxy functions. After 15 min of stirring at room temperature, the solution was concentrated to dryness. The residue was treated with dichloromethane and the product was not soluble. The resulting precipitate was dissolved in 20 ml of pyridine and was treated with trimethylchlorosilane (20 mmol, 2.9 ml). After 25 min of magnetic stirring at room temperature, isobutyryl chloride (16.8 mmol, 1.8 ml) was added and the solution was stirred for 3 hr at room temperature. The mixture was cooled with an ice-bath and water (2 ml) was added followed by 2 ml of concentrated ammonia. After 15 min of magnetic stirring at room temperature, the solution was concentrated to dryness. The resulting product was purified by silica gel chromatography yielding 1.8 g of $N^8$-isobutyryl-$N^8$-phenoxyacetyl-8-amino-2'-deoxyinosine (4 mmol, 71% yield).

The product described above was dissolved into dry pyridine (20 ml) and dimethoxytrityl chloride (1.7 g, 5.2 mmol) was added to the solution. After 3 hr of magnetic stirring at room temperature, methanol (2 ml) was added and the solution was concentrated to dryness. The residue was dissolved in dichloromethane and the solution was washed with aqueous sodium bicarbonate solution and brine. The organic phase was dried over $Na_2SO_4$ and evaporated. Silica gel chromatography yielded 2.1 g (3.4 mmol, 85% yield) of 5'-dimethoxytrityl-$N^8$-isobutyryl-8-amino-2'-deoxyinosine. Unexpectedly, the phenoxyacetyl group was eliminated during the work-up due to the lability of this group.

The protected nucleoside (3.4 mmol) described above was dissolved in dry dichloromethane (15 ml) and diisopropylethylamine was added (2.4 ml, 13.7 mmol). To the solution chloro 2-cyanoethoxy diisopropylamino phosphine (1.1 ml, 5,1 mmol) was added dropwise with a syringe. After 1 hr of magnetic stirring at room temperature, methanol (2 ml) was added and the solution was concentrated to dryness. The resulting residue was dissolved in dichloromethane and washed with aqueous sodium bicarbonate solution and brine. The organic phase was dried over $Na_2SO_4$ and evaporated. Silica gel chromatography yielded 2.1 g (2.6 mmol, 76% yield) of the desired phosphoramidite.

Example 7
Preparation of Oligomers Containing 8-aminopurines.

Oligonucleotides were prepared on an automatic DNA synthesizer using standard and reversed 2-cyanoethyl phosphoramidites and the modified phosphoramidites of the 8-aminopurines. The phosphoramidite of protected 8-amino-2'-deoxyinosine was dissolved in dry dichloromethane to make a 0.1 M solution. The rest of the phosphoramidites were dissolved in dry acetonitrile (0.1 M solution). The phosphoramidite of the hexaethyleneglycol linker was obtained from commercial sources. Complementary oligonucleotides containing natural bases were also prepared using commercially available chemicals and following standard protocols. After the assembly of the sequences, oligonucleotide-supports were treated with 32% aqueous ammonia at 55° C. for 16 h except for oligonucleotides having 8-aminoguanine. In this case a 0.1 M 2-mercaptoethanol solution in 32% aqueous ammonia was used and the treatment was extended to 24 h at 55° C. Ammonia solutions were concentrated to dryness and the products were purified by reverse-phase HPLC. Oligonucleotides were synthesized on 0.2 mmol scale and with the last DMT group at the 5' end (DMT on protocol) to help reverse-phase purification. All purified products presented a major peak which was collected and analyzed by snake venom phosphodiesterase and alkaline phosphatase digestion followed by HPLC analysis of the nucleosides (HPLC conditions B). Yield (OD units at 260 nm after HPLC purification, 0.2 mmol) were between 6–10 OD. HPLC conditions: HPLC solutions are as follows. Solvent A: 5% ACN in 100 mM triethylammonium acetate (pH 6.5) and solvent B: 70% ACN in 100 mM triethylammonium acetate pH 6.5. For analytical runs the following conditions were used. Column: Nucleosil $120C_{18}$, 250×4 mm, flow rate: 1 ml/min. Conditions A) a 40 min linear gradient from 0 to 75% B. Conditions B) a 20 min linear gradient from 0 to 20% B. For preparative runs the following conditions were used: Columns: PRP-1 (Hamilton), 250×10 mm. Flow rate: 3 ml/min. A 30 min linear gradient from 10–80% B (DMT on), or a 30 min linear gradient from 0–50% B (DMT off).

Example 8

Binding of oligomers of the invention to target sequences by melting experiments.

Melting experiments with triple helix were performed as follows: Solutions of equimolar amounts of the modified oligonucleotide (22-mer) and the target Watson-Crick pyrimidine strand (11-mer) were mixed in the appropriate buffer. The solutions were heated to 90° C., allowed to cool slowly to room temperature and then samples were kept in the refrigerator overnight. UV absorption spectra and melting experiments (absorbance vs temperature) were recorded in 1 cm path-length cells using a spectrophotometer, which has a temperature controller with a programmed temperature increase of 0.5° C./min. Melts were run on duplex concentration of 4 mM at 260 nm.

Example 9

Binding of Oligomers of the Invention to Target Sequences by Gel-shift Experiments.

In addition to melting experiments the binding of oligomers of the invention to their polypyrimidine targets was analysed by gel retardation assays. The following targets were studied:

Single stranded target:

WC-11mer: $^{5'}$TCTCCTCCTTC$^{3'}$ (SEQ ID NO:15) and

Double stranded target:

WC-11mer: $^{5'}$TCTCCTCCTTC$^{3'}$ (SEQ ID NO:15)

Complementary purine strand $^{3'}$AGAGGAGGAAG$^{5'}$ (SEQ ID NO: 1)

The target was radioactively labelled at the 5' end by T4 polynucleotide kinase and [$\gamma$-$^{32}$P]-ATP. The reaction was performed with 35–50 mmol of the target oligonucleotide dissolved in 20 ml of kinase buffer. After incubation at 37° C. for 45 min, the solution was heated at 70° C. for 10 min to denature the enzyme and the solution was cooled to room temperature. To the solution 60 ml of a 50 mM potassium acetate in ethanol were added and the mixture was left at −20° C. for at least 3 hr. The mixture was centrifuged at 4° C. for 45 min (14000 rpm) and the supernatant was removed. The pellet was washed with 60 ml of 80% ethanol and centrifuge for 20 min at 4° C. The supernatant was removed and the pellet was dissolved in 0.2 ml of water.

The radiolabelled target was incubated with the hairpins of the invention in 0.1 M sodium phosphate/citric acid buffer of pH ranging from 5.5 to 7.0 at room temperature for 30–60 min. The hairpins were added increasing amounts from 2 to 200 molar equivalents. After incubation the mixtures were analysed by 10–15% polyacrylamide gel electrophoresis. The buffer used on the electrophoresis was the same buffer used during the incubation: 0.1 M sodium phosphate/citric acid buffer of pH ranging from 5.5 to 7.0. The formation of the triplex was followed by the appearance of a radioactive band with less mobility than the band corresponding to the target alone. The sequences of the hairpins are shown in Table 1.

Example 10

Hybridization Properties of Oligonucleotides Carrying 8-amino-2'-deoxyinosine.

Solutions of equimolar amounts of the pentadecamer carrying 8-amino-2'-deoxyinosine or 2'-deoxyinosine at the central position and its complementary sequences carrying each of the four natural bases opposite to the modified base were mixed in the appropriate buffer. The solutions were heated to 90° C., allowed to cool slowly to room temperature and then samples were kept in the refrigerator overnight. UV absorption spectra and melting experiments (absorbance vs temperature) were recorded in 1 cm path-length cells using a spectrophotometer, which has a temperature controller with a programmed temperature increase of 0.5° C./min. Melts were run on duplex concentration of 4 mM at 260 nm.

Example 11

A preferred method of use of the present invention comprises the following steps.

1. Mildly heat the sample DNA at 50–60° C. for approximately 10 minutes.
2. Add a first specific hairpin probe.
3. Incubate at 50° C. to allow the formation of the triplex structure.
4. Add a second hairpin probe, covalently attached to the magnetized beads via a spacer arm linked to the loop region of the hairpin.
5. Incubate at approximately 50° C. to allow a second triplex structure to form.
6. Add the magnets to concentrate the beads/sample complex.
7. Wash several time while the magnets are present to eliminate the excess unbound first and second hairpins.
8. Remove the magnets and resuspend the bead/sample complex.
9. Add a reporter probe modified with a hexapeptide.
10. Incubate at approximately 50° C. to allow the reporter probe to hybridize.
11. Add the magnets to concentrate the beads/sample complex.
12. Wash several times while the magnets are present to remove any excess, unbound hexapeptide-modified reporter probe.
13. Remove the magnets and resuspend the beads/sample complex.
14. Add the hexapeptide-specific antibody-modified fluorophore-filled liposomes.
15. Incubate at approximately 37° C. to allow the antibody-peptide complex to form.
16. Add the magnets to concentrate the beads/sample complex.
17. Wash several times while the magnets are present to remove any excess, unbound monoclonal antibody-modified fluorophore-filled liposomes.
18. Remove the magnets and resuspend the beads/sample complex.
19. Add a mild ionic detergent to open the liposome channels and release the fluorophore for detection of the fluorescence.

Example 12

Synthesis of Hairpins Carrying Peptide Sequences.

An oligonucleotide containing 8-amino derivatives attached to a short peptide c-myc was prepared using two different synthetic routes.

A. Stepwise Solid-phase Synthesis

The route to the synthesis of the oligonucleotide-peptide conjugate is illustrated in FIG. 25 and FIG. 26. Using a base-labile linker attached to a PEG-PS support, the peptide is first assembled. Boc-amino acids protected with the base labile Fmoc and Fm groups are used as coupling units. The repetitive acid treatments used for the removal the Boc group were performed without the presence of the oligonucleotide.

Another important feature of the synthesis of a conjugate is the choice of the solid support. Polystyrene supports are used in peptide synthesis, and CPG supports are incorporated for oligonucleotide synthesis. Coupling reactions on Teflon, PS and PEG-PS are less dependent on the activation method used during peptide synthesis than on CPG, but are less efficient in oligonucleotide synthesis. The low efficiency of these supports is compensated by increasing the coupling time and changing the solvent to dissolve the phosphoramidites.

The peptide sequence was synthesized via the solid phase on a 0.19 mmol scale using a homemade manual synthesizer and amino-PEG-PS (0.19 mmol) as the solid support. The handle, 6-DMT-aminohex-1-yl hemisuccinate, was anchored to the resin as described elsewhere. The loading of the support was measured by the absorbance of the DMT cation and was 0.1 mmol/g. The elongation of the peptide was carried out in DMF using a 5-fold excess of Boc-amino acid, 10-fold excess of DIEA, and 5-fold excess of PyBOP for 1 h. In order to remove the Boc group, the support was treated with TFA-DCM (3:7) for 30 min and neutralized with DIEA-DCM (1:19).

After the addition of the last amino acid, the 6-hydroxypentanoate linker (5-fold excess in DMF for 1 h) was added to connect the peptide fragment to the oligonucleotide by converting the last amino group of the peptide to a dimethoxytrityl-protected hydroxyl function.

The oligonucleotide component is assembled using the standard phosphoramidites on a DNA-Synthesizer on a 1 µmol scale. The phosphoramidites were disolved in dry DCM, giving 0.1 M solutions (using reverse phosphoramidites for the pyrimidine chain growth and normal phosphoramidites and 8-amino derivatives for the purine chain elongation). The coupling time was increased to 5 min, capping and oxidation times were increased to 1 min, and the detritylation step to 2 min. The last DMT protecting group was not removed. The supports were washed with ACN and dried. Following linear assembly, some of the protecting groups (Fmoc, Fm, CNE) are removed with DBU. The conjugate is liberated from the solid support by concentrated ammonia (with drops of dioxane) in an overnight treatment at 55° C., with concomitant removal of the nucleobase protecting groups.

After filtration of the solid support, the solution was evaporated to dryness, the residue was disolved in water, and the conjugate purified using standard two-step HPLC purification. In the first sep, truncated sequences were separated from the DMT-containing product, and in the second sep the conjugate was isolated after removal of the DMT group with 80% aqueous acetic acid for 30 min. Characterization was performed via mass spectrometry analysis after 6 N HCl hydrolysis.

The Asymmetric Doubler Approach

The peptidyl support was prepared as for the stepwise solid-phase approach as illustrated in FIG. 25. After the addition of the last amino acid, the 6-hydroxypentanoate linker (5-fold excess in DMF for 1 h) was also added to connect the peptide fragment to the oligonucleotide by converting the last amino group of the peptide to a dimethoxytrityl-protected hydroxyl function.

Referring to FIG. 27, before the oligonucleotide assembly, an asymmetric doubler was incorporated to the peptidyl support. One arm has an Tfa-hydroxyl protection, while the second arm presents a DMT-alcohol protecting group. The synthesis proceeded deprotecting the DMT and elongating the purine strand using normal phosphoramidites. Just after that, an acetilation treatment took place before the base deprotection of the second arm. The pyrimidine chain was assembled with standard monomers.

The phosphoramidites were disolved in dry DCM, giving 0.1 M solutions. The coupling time was increased to 5 min, capping and oxidation times were increased to 1 min, and the detritylation step to 2 min. The last DMT protecting group was not removed. The supports were washed with ACN and dried. Following linear assembly, some of the protecting groups (Fmoc, Fm, CNE) were removed with DBU. The conjugate was liberated from the solid support by concentrated ammonia (with drops of dioxane) in an overnight treatment at 55° C., with concomitant removal of the nucleobase protecting groups.

After filtration of the solid support, the solution was evaporated to dryness, the residue was disolved in water, and the conjugate purified using standard two-step HPLC purification. In the first sep, truncated sequences were separated from the DMT-containing product, and in the second sep the conjugate was isolated after removal of the DMT group with 80% aqueous acetic acid for 30 mn.

The disclosures of all patents and publications cited in this application are hereby incorporated by reference in their entireties in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A method of making 8-amino-2'deoxyadenosine comprising:

treating 8-azido-2'deoxyadenosine with an aqueous amine solution to form 8-amino-2'deoxyadenosine.

2. The method of claim 1, wherein the 8-azido-2'deoxyadenosine is treated with the aqueous amine solution at a temperature of about 55° C.

3. The method of claim 1, wherein the aqueous amine solution is methylamine.

4. The method of claim 1, wherein the aqueous amine solution is dimethylamine.

5. The method of claim 1, wherein the aqueous amine solution is a 40% aqueous methylamine solution.

6. The method of claim 1, wherein the aqueous amine solution is a 30% aqueous dimethylamine solution.

7. The method of claim 5, wherein the 8-azido-2'deoxyadenosine is treated for about 5 hours.

8. The method of claim 6, wherein the 8-azido-2'deoxyadenosine is treated for about 16 hours.

* * * * *

UNITED STATES PATENT AND TRADEMARK OFFICE
CERTIFICATE OF CORRECTION

PATENT NO. : 6,831,072 B2
DATED : December 14, 2004
INVENTOR(S) : Ramon Eritja and Ramon Guimil Garcia It is certified that error appears in the above-identified patent and that said Letters Patent is hereby corrected as shown below:

Title page,
Item [56], References Cited, OTHER PUBLICATIONS, "Holmes, R.E. and Robins," reference, (first occurrence), please change "Sythesis" to -- Synthesis -- and change "Subsituted" to -- Substituted --.
Please delete the entire "Holmes R.E. and Robins, R.K." reference, (second occurrence) and insert the following:
-- Hattori, M. et al. Poly(8-aminoguanylic acid): Formation of Ordered Self-Structures and Interaction with Poly(cytidylic acid), Biochem. 1975; 14: 5033-5045. --.

Signed and Sealed this

Fourth Day of October, 2005

JON W. DUDAS
*Director of the United States Patent and Trademark Office*

SEQUENCE LISTING

<160> NUMBER OF SEQ ID NOS: 30

<210> SEQ ID NO 1
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 1
gaaggaggag a                                                          11

<210> SEQ ID NO 2
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 2
cttcctcctc t                                                                 11

<210> SEQ ID NO 3
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(9)
<223> OTHER INFORMATION: Any n = 8-aminoadenine

<400> SEQUENCE: 3
gaaggnggng a                                                                 11

<210> SEQ ID NO 4
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(8)
<223> OTHER INFORMATION: Any n = 8-aminoguanine

<400> SEQUENCE: 4
gaagnagnag a                                                                 11

<210> SEQ ID NO 5
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(8)
<223> OTHER INFORMATION: Any n = 8-aminohypoxanthine

<400> SEQUENCE: 5
gaagnagnag a                                                                 11

<210> SEQ ID NO 6
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n = 8-aminoguanine
<220> FEATURE:
<221> NAME/KEY: misc_feature
<222> LOCATION: (6)..(6)
<223> OTHER INFORMATION: n = 8-aminoadenine
<220> FEATURE:
<221> NAME/KEY: misc_feature
<222> LOCATION: (8)..(8)
<223> OTHER INFORMATION: n = 8-aminoguanine
<220> FEATURE:

-continued

<221> NAME/KEY: misc_feature
<222> LOCATION: (9)..(9)
<223> OTHER INFORMATION: n = 8-aminoadenine

<400> SEQUENCE: 6
gaagnngnng a                                                                 11

<210> SEQ ID NO 7
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 7
tttttccccc c                                                                 11

<210> SEQ ID NO 8
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(9)
<223> OTHER INFORMATION: Any n = 8-aminoadenine

<400> SEQUENCE: 8
gaagcnggng a                                                                 11

<210> SEQ ID NO 9
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Synthetic oligonucleotide

<400> SEQUENCE: 9
cttcttcctc t                                                                 11

<210> SEQ ID NO 10
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Synthetic oligonucleotide

<400> SEQUENCE: 10
ttttcttcct cctct                                                             15

<210> SEQ ID NO 11
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(13)
<223> OTHER INFORMATION: Any n = 8-aminoadenine

<400> SEQUENCE: 11

-continued

```
ttttgaaggn ggnga                                              15

<210> SEQ ID NO 12
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: Any n = 8-aminoadenine

<400> SEQUENCE: 12
ggagggaagg nggnga                                             16

<210> SEQ ID NO 13
<211> LENGTH: 4
<212> TYPE: DNA
<213> ORGANISM: Artificial Sequence
<220> FEATURE:
<223> OTHER INFORMATION: Synthetic oligonucleotide

<400> SEQUENCE: 13 tttt                                                           4

<210> SEQ ID NO 14
<211> LENGTH: 5
<212> TYPE: DNA
<213> ORGANISM: Artificial Sequence
<220> FEATURE:
<223> OTHER INFORMATION: Synthetic oligonucleotide

<400> SEQUENCE: 14 ggagg                                                          5

<210> SEQ ID NO 15
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 15
tctcctcctt c                                                  11

<210> SEQ ID NO 16
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 16
tctcctgctt c                                                  11

<210> SEQ ID NO 17
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n = either 8-aminohypoxanthine or hypoxanthine
```

```
<400> SEQUENCE: 17
tagaggntcc attgc                                                    15

<210> SEQ ID NO 18
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: n = adenine, guanine, cytosine or thymine

<400> SEQUENCE: 18
gcaatgganc ctcta                                                    15

<210> SEQ ID NO 19
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(9)
<223> OTHER INFORMATION: Any "n" = 8-aminoadenine

<400> SEQUENCE: 19
gaagtnggng a                                                        11

<210> SEQ ID NO 20
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 20
cttcgtcctc t                                                        11

<210> SEQ ID NO 21
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 21
cttcatcctc t                                                        11

<210> SEQ ID NO 22
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: "n" = propanediol

<400> SEQUENCE: 22
cttcntcctc t                                                        11

<210> SEQ ID NO 23
<211> LENGTH: 11
```

```
<212> TYPE: DNA
<213> ORGANISM: Artificial Sequence
<220> FEATURE:
<223> OTHER INFORMATION: Synthetic oligonucleotide

<400> SEQUENCE: 23
tctcctactt c                                                              11

<210> SEQ ID NO 24
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(8)
<223> OTHER INFORMATION: every "n" = methylated cytosine
<220> FEATURE:
<221> NAME/KEY: misc_feature
<222> LOCATION: (2)..(8)
<223> OTHER INFORMATION: every "n" = 5-methyl-cytosine

<400> SEQUENCE: 24 tntnntnnttt c                                                             11

<210> SEQ ID NO 25
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 25
gaaggaggag att                                                            13

<210> SEQ ID NO 26
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 26
cttcctcctc ttt                                                            13

<210> SEQ ID NO 27
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(9)
<223> OTHER INFORMATION: Any n = 8-aminoadenine

<400> SEQUENCE: 27
gaaggnggng att                                                            13

<210> SEQ ID NO 28
<211> LENGTH: 13
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(13)
```

```
<223> OTHER INFORMATION: 2'- O-methyl RNA

<400> SEQUENCE: 28
cuuccuccuc uuu                                                          13

<210> SEQ ID NO 29
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: every "n" = 5-methyl-cytosine

<400> SEQUENCE: 29
nttnntnntn ttt                                                          13

<210> SEQ ID NO 30
<211> LENGTH: 11
<212> TYPE: RNA
<213> ORGANISM: Artificial Sequence
<220> FEATURE:
<223> OTHER INFORMATION: Synthetic oligonucleotide

<400> SEQUENCE: 30
ucuccuccuu c                                                            11
```